(12) United States Patent
Aronhalt et al.

(10) Patent No.: US 9,113,883 B2
(45) Date of Patent: Aug. 25, 2015

(54) COLLAPSIBLE ANVIL PLATE ASSEMBLIES FOR CIRCULAR SURGICAL STAPLING DEVICES

(75) Inventors: Taylor W. Aronhalt, Loveland, OH (US); Frederick E. Shelton, IV, Hillsboro, OH (US); Kreena R. Modi, Akron, OH (US); Christopher J. Schall, Cincinnati, OH (US); Joseph E. Young, Loveland, OH (US); Barry C. Worrell, Centerville, OH (US); Jerome R. Morgan, Cincinnati, OH (US); William B. Weisenburgh, II, Maineville, OH (US); Christopher J. Hess, Cincinnati, OH (US); Emily A. Heeb, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 800 days.

(21) Appl. No.: 13/181,768

(22) Filed: Jul. 13, 2011

(65) Prior Publication Data

US 2012/0234890 A1    Sep. 20, 2012

Related U.S. Application Data

(60) Provisional application No. 61/452,432, filed on Mar. 14, 2011.

(51) Int. Cl.
*A61B 17/068* (2006.01)
*A61B 17/115* (2006.01)
(Continued)

(52) U.S. Cl.
CPC ....... *A61B 17/1155* (2013.01); *A61B 17/00234* (2013.01); *A61B 17/3417* (2013.01); *A61B 2017/00287* (2013.01); *A61B 2017/00477* (2013.01); *A61B 2017/07257* (2013.01)

(58) Field of Classification Search
CPC .............................. A61B 17/068; A61B 17/072
USPC ...................... 227/175.1, 176.1, 179.1, 180.1; 606/151, 153, 142, 219
See application file for complete search history.

(56) References Cited

U.S. PATENT DOCUMENTS

| 2,224,882 A | 12/1940 | Peck |
| 3,166,072 A | 1/1965 | Sullivan, Jr. |

(Continued)

FOREIGN PATENT DOCUMENTS

| AU | 2012200178 B2 | 7/2013 |
| CA | 2458946 A1 | 3/2003 |

(Continued)

OTHER PUBLICATIONS

International Search Report for PCT/US2012/028886, dated Nov. 23, 2012 (6 pages).

(Continued)

*Primary Examiner* — Nathaniel Chukwurah

(57) ABSTRACT

Circular stapling instruments and anvil assemblies. The anvil assemblies may have collapsible anvil support members that may be inserted through an opening in a patient and then expanded to be attached to an anvil plate assembly that has a staple-forming surface thereon. The anvil support member is attachable to the anvil plate assembly in such a way that when the anvil assembly is coupled to the stapling head of a circular stapler, the staple-forming surface is in substantial registry with the staples supported in the stapling head. A variety of different anvil support members and anvil plate assemblies are disclosed.

22 Claims, 38 Drawing Sheets

(51) Int. Cl.
  *A61B 17/34* (2006.01)
  *A61B 17/00* (2006.01)
  *A61B 17/072* (2006.01)

(56) References Cited

U.S. PATENT DOCUMENTS

| | | | |
|---|---|---|---|
| 3,266,494 A | 8/1966 | Brownrigg et al. | |
| 3,746,002 A | 7/1973 | Haller | |
| 3,863,639 A | 2/1975 | Kleaveland | |
| 4,190,042 A | 2/1980 | Sinnreich | |
| 4,274,398 A | 6/1981 | Scott, Jr. | |
| 4,505,272 A | 3/1985 | Utyamyshev et al. | |
| 4,505,273 A | 3/1985 | Braun et al. | |
| 4,505,414 A | 3/1985 | Filipi | |
| 4,654,028 A | 3/1987 | Suma | |
| 4,655,222 A | 4/1987 | Florez et al. | |
| 4,700,703 A * | 10/1987 | Resnick et al. | 227/176.1 |
| 4,744,363 A | 5/1988 | Hasson | |
| 4,873,977 A | 10/1989 | Avant et al. | |
| 4,893,622 A | 1/1990 | Green et al. | |
| 4,903,697 A | 2/1990 | Resnick et al. | |
| 4,909,789 A | 3/1990 | Taguchi et al. | |
| 4,984,564 A | 1/1991 | Yuen | |
| 5,002,553 A | 3/1991 | Shiber | |
| 5,071,430 A | 12/1991 | de Salis et al. | |
| 5,104,025 A | 4/1992 | Main et al. | |
| 5,104,397 A | 4/1992 | Vasconcelos et al. | |
| 5,108,368 A | 4/1992 | Hammerslag et al. | |
| 5,122,156 A | 6/1992 | Granger et al. | |
| 5,139,513 A | 8/1992 | Segato | |
| 5,158,567 A | 10/1992 | Green | |
| 5,195,505 A | 3/1993 | Josefsen | |
| 5,197,649 A * | 3/1993 | Bessler et al. | 227/179.1 |
| 5,205,459 A | 4/1993 | Brinkerhoff et al. | |
| 5,211,655 A | 5/1993 | Hasson | |
| 5,222,963 A | 6/1993 | Brinkerhoff et al. | |
| 5,222,975 A | 6/1993 | Crainich | |
| 5,234,447 A | 8/1993 | Kaster et al. | |
| 5,236,440 A | 8/1993 | Hlavacek | |
| 5,258,009 A | 11/1993 | Conners | |
| 5,282,829 A | 2/1994 | Hermes | |
| 5,285,945 A | 2/1994 | Brinkerhoff et al. | |
| 5,304,204 A | 4/1994 | Bregen | |
| 5,309,927 A | 5/1994 | Welch | |
| 5,314,445 A | 5/1994 | Heidmueller née Degwitz et al. | |
| 5,330,502 A | 7/1994 | Hassler et al. | |
| 5,336,232 A | 8/1994 | Green et al. | |
| 5,342,395 A | 8/1994 | Jarrett et al. | |
| 5,342,396 A | 8/1994 | Cook | |
| 5,350,400 A | 9/1994 | Esposito et al. | |
| 5,354,250 A | 10/1994 | Christensen | |
| 5,354,303 A | 10/1994 | Spaeth et al. | |
| 5,358,506 A | 10/1994 | Green et al. | |
| 5,366,479 A | 11/1994 | McGarry et al. | |
| 5,374,277 A | 12/1994 | Hassler | |
| 5,383,888 A | 1/1995 | Zvenyatsky et al. | |
| 5,383,895 A | 1/1995 | Holmes et al. | |
| 5,391,180 A | 2/1995 | Tovey et al. | |
| 5,395,030 A | 3/1995 | Kuramoto et al. | |
| 5,395,384 A | 3/1995 | Duthoit | |
| 5,404,870 A | 4/1995 | Brinkerhoff et al. | |
| 5,405,344 A | 4/1995 | Williamson et al. | |
| 5,411,508 A | 5/1995 | Bessler et al. | |
| 5,413,573 A | 5/1995 | Koivukangas | |
| 5,425,745 A | 6/1995 | Green et al. | |
| 5,441,494 A | 8/1995 | Ortiz | |
| 5,445,644 A | 8/1995 | Pietrafitta et al. | |
| 5,474,057 A | 12/1995 | Makower et al. | |
| 5,476,479 A | 12/1995 | Green et al. | |
| 5,478,354 A | 12/1995 | Tovey et al. | |
| 5,480,409 A | 1/1996 | Riza | |
| 5,490,819 A | 2/1996 | Nicholas et al. | |
| 5,503,635 A | 4/1996 | Sauer et al. | |
| 5,514,157 A | 5/1996 | Nicholas et al. | |
| 5,520,609 A | 5/1996 | Moll et al. | |
| 5,520,678 A | 5/1996 | Heckele et al. | |
| 5,527,264 A | 6/1996 | Moll et al. | |
| 5,549,621 A | 8/1996 | Bessler et al. | |
| 5,549,637 A | 8/1996 | Crainich | |
| 5,554,169 A | 9/1996 | Green et al. | |
| 5,556,416 A | 9/1996 | Clark et al. | |
| 5,558,665 A | 9/1996 | Kieturakis | |
| 5,562,690 A | 10/1996 | Green et al. | |
| 5,562,701 A | 10/1996 | Huitema et al. | |
| 5,562,702 A | 10/1996 | Huitema et al. | |
| 5,571,285 A | 11/1996 | Chow et al. | |
| 5,575,803 A | 11/1996 | Cooper et al. | |
| 5,575,805 A | 11/1996 | Li | |
| 5,607,450 A | 3/1997 | Zvenyatsky et al. | |
| 5,613,937 A | 3/1997 | Garrison et al. | |
| 5,618,303 A | 4/1997 | Marlow et al. | |
| 5,618,307 A | 4/1997 | Donlon et al. | |
| 5,620,452 A | 4/1997 | Yoon | |
| 5,628,743 A | 5/1997 | Cimino | |
| 5,651,762 A | 7/1997 | Bridges | |
| 5,653,721 A | 8/1997 | Knodel et al. | |
| 5,667,517 A | 9/1997 | Hooven | |
| 5,667,526 A | 9/1997 | Levin | |
| 5,667,527 A | 9/1997 | Cook | |
| 5,681,341 A | 10/1997 | Lunsford et al. | |
| 5,683,349 A | 11/1997 | Makower et al. | |
| 5,695,504 A | 12/1997 | Gifford, III et al. | |
| 5,695,524 A | 12/1997 | Kelley et al. | |
| 5,697,943 A | 12/1997 | Sauer et al. | |
| 5,702,409 A | 12/1997 | Rayburn et al. | |
| 5,707,392 A | 1/1998 | Kortenbach | |
| 5,709,706 A | 1/1998 | Kienzle et al. | |
| 5,725,554 A | 3/1998 | Simon et al. | |
| 5,728,121 A | 3/1998 | Bimbo et al. | |
| 5,730,758 A | 3/1998 | Allgeyer | |
| 5,735,874 A | 4/1998 | Measamer et al. | |
| 5,738,629 A | 4/1998 | Moll et al. | |
| 5,741,271 A | 4/1998 | Nakao et al. | |
| 5,749,889 A | 5/1998 | Bacich et al. | |
| 5,749,893 A | 5/1998 | Vidal et al. | |
| 5,752,965 A | 5/1998 | Francis et al. | |
| 5,752,970 A | 5/1998 | Yoon | |
| 5,766,188 A | 6/1998 | Igaki | |
| 5,766,205 A | 6/1998 | Zvenyatsky et al. | |
| 5,769,892 A | 6/1998 | Kingwell | |
| 5,782,859 A | 7/1998 | Nicholas et al. | |
| 5,785,647 A | 7/1998 | Tompkins et al. | |
| 5,792,135 A | 8/1998 | Madhani et al. | |
| 5,797,959 A | 8/1998 | Castro et al. | |
| 5,807,376 A | 9/1998 | Viola et al. | |
| 5,807,378 A | 9/1998 | Jensen et al. | |
| 5,810,721 A | 9/1998 | Mueller et al. | |
| 5,810,855 A | 9/1998 | Rayburn et al. | |
| 5,814,055 A | 9/1998 | Knodel et al. | |
| 5,814,057 A | 9/1998 | Oi et al. | |
| 5,817,084 A | 10/1998 | Jensen | |
| 5,839,369 A | 11/1998 | Chatterjee et al. | |
| 5,839,639 A | 11/1998 | Sauer et al. | |
| 5,843,096 A | 12/1998 | Igaki et al. | |
| 5,860,581 A * | 1/1999 | Robertson et al. | 227/179.1 |
| 5,931,853 A | 8/1999 | McEwen et al. | |
| 5,947,984 A | 9/1999 | Whipple | |
| 5,964,774 A | 10/1999 | McKean et al. | |
| 5,997,528 A | 12/1999 | Bisch et al. | |
| 6,017,356 A | 1/2000 | Frederick et al. | |
| 6,024,748 A | 2/2000 | Manzo et al. | |
| RE36,720 E | 5/2000 | Green et al. | |
| 6,056,735 A | 5/2000 | Okada et al. | |
| 6,063,097 A | 5/2000 | Oi et al. | |
| 6,083,234 A | 7/2000 | Nicholas et al. | |
| 6,083,242 A | 7/2000 | Cook | |
| 6,099,551 A | 8/2000 | Gabbay | |
| 6,117,158 A | 9/2000 | Measamer et al. | |
| 6,142,933 A | 11/2000 | Longo et al. | |
| 6,159,146 A | 12/2000 | El Gazayerli | |
| 6,159,200 A | 12/2000 | Verdura et al. | |
| 6,162,208 A | 12/2000 | Hipps | |
| 6,165,188 A | 12/2000 | Saadat et al. | |
| 6,171,330 B1 | 1/2001 | Benchetrit | |

(56) References Cited

U.S. PATENT DOCUMENTS

| | | |
|---|---|---|
| 6,174,318 B1 | 1/2001 | Bates et al. |
| 6,214,028 B1 | 4/2001 | Yoon et al. |
| 6,221,007 B1 | 4/2001 | Green |
| 6,231,565 B1 | 5/2001 | Tovey et al. |
| 6,248,117 B1 | 6/2001 | Blatter |
| 6,258,107 B1 | 7/2001 | Balázs et al. |
| 6,309,403 B1 | 10/2001 | Minor et al. |
| 6,325,810 B1 | 12/2001 | Hamilton et al. |
| 6,338,737 B1 | 1/2002 | Toledano |
| 6,346,077 B1 | 2/2002 | Taylor et al. |
| 6,352,503 B1 | 3/2002 | Matsui et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| 6,402,766 B2 | 6/2002 | Bowman et al. |
| RE37,814 E | 8/2002 | Allgeyer |
| 6,436,110 B2 | 8/2002 | Bowman et al. |
| 6,436,122 B1 | 8/2002 | Frank et al. |
| 6,440,146 B2 | 8/2002 | Nicholas et al. |
| 6,443,973 B1 | 9/2002 | Whitman |
| 6,494,885 B1 | 12/2002 | Dhindsa |
| 6,503,257 B2 | 1/2003 | Grant et al. |
| 6,503,259 B2 | 1/2003 | Huxel et al. |
| 6,517,565 B1 | 2/2003 | Whitman et al. |
| 6,517,566 B1 | 2/2003 | Hovland et al. |
| 6,551,333 B2 | 4/2003 | Kuhns et al. |
| 6,582,364 B2 | 6/2003 | Butler et al. |
| 6,592,597 B2 | 7/2003 | Grant et al. |
| 6,605,078 B2 | 8/2003 | Adams |
| 6,616,686 B2 | 9/2003 | Coleman et al. |
| 6,629,988 B2 | 10/2003 | Weadock |
| 6,638,285 B2 | 10/2003 | Gabbay |
| 6,638,297 B1 | 10/2003 | Huitema |
| 6,645,201 B1 | 11/2003 | Utley et al. |
| 6,656,193 B2 | 12/2003 | Grant et al. |
| 6,666,854 B1 | 12/2003 | Lange |
| 6,692,507 B2 | 2/2004 | Pugsley et al. |
| 6,699,235 B2 | 3/2004 | Wallace et al. |
| 6,716,232 B1 | 4/2004 | Vidal et al. |
| 6,716,233 B1 | 4/2004 | Whitman |
| 6,723,087 B2 | 4/2004 | O'Neill et al. |
| 6,726,697 B2 | 4/2004 | Nicholas et al. |
| 6,736,825 B2 | 5/2004 | Blatter et al. |
| 6,769,590 B2 | 8/2004 | Vresh et al. |
| 6,780,151 B2 | 8/2004 | Grabover et al. |
| 6,786,896 B1 | 9/2004 | Madani et al. |
| 6,793,652 B1 | 9/2004 | Whitman et al. |
| 6,821,284 B2 | 11/2004 | Sturtz et al. |
| 6,827,712 B2 | 12/2004 | Tovey et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,872,214 B2 | 3/2005 | Sonnenschein et al. |
| 6,913,608 B2 | 7/2005 | Liddicoat et al. |
| 6,913,613 B2 | 7/2005 | Schwarz et al. |
| 6,936,042 B2 | 8/2005 | Wallace et al. |
| 6,939,358 B2 | 9/2005 | Palacios et al. |
| 6,960,220 B2 | 11/2005 | Marino et al. |
| 6,981,978 B2 | 1/2006 | Gannoe |
| 7,001,408 B2 | 2/2006 | Knodel et al. |
| 7,052,454 B2 | 5/2006 | Taylor |
| 7,056,330 B2 | 6/2006 | Gayton |
| 7,063,712 B2 | 6/2006 | Vargas et al. |
| 7,066,944 B2 | 6/2006 | Laufer et al. |
| 7,077,856 B2 | 7/2006 | Whitman |
| 7,080,769 B2 * | 7/2006 | Vresh et al. ............... 227/176.1 |
| 7,087,071 B2 | 8/2006 | Nicholas et al. |
| 7,094,247 B2 | 8/2006 | Monassevitch et al. |
| 7,108,701 B2 | 9/2006 | Evens et al. |
| 7,108,709 B2 | 9/2006 | Cummins |
| 7,122,028 B2 | 10/2006 | Looper et al. |
| 7,128,748 B2 | 10/2006 | Mooradian et al. |
| 7,147,650 B2 | 12/2006 | Lee |
| 7,156,863 B2 | 1/2007 | Sonnenschein et al. |
| 7,179,267 B2 | 2/2007 | Nolan et al. |
| 7,208,005 B2 | 4/2007 | Frecker et al. |
| 7,220,272 B2 | 5/2007 | Weadock |
| 7,229,408 B2 | 6/2007 | Douglas et al. |
| 7,238,195 B2 | 7/2007 | Viola |
| 7,241,288 B2 | 7/2007 | Braun |
| 7,252,660 B2 | 8/2007 | Kunz |
| 7,267,679 B2 | 9/2007 | McGuckin, Jr. et al. |
| 7,300,450 B2 | 11/2007 | Vleugels et al. |
| 7,328,828 B2 | 2/2008 | Ortiz et al. |
| 7,338,505 B2 | 3/2008 | Belson |
| 7,338,513 B2 | 3/2008 | Lee et al. |
| 7,354,447 B2 | 4/2008 | Shelton, IV et al. |
| 7,377,928 B2 | 5/2008 | Zubik et al. |
| 7,404,822 B2 | 7/2008 | Viart et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,682 B2 | 11/2008 | Viola |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,473,221 B2 | 1/2009 | Ewers et al. |
| 7,481,824 B2 | 1/2009 | Boudreaux et al. |
| 7,490,749 B2 | 2/2009 | Schall et al. |
| 7,491,232 B2 | 2/2009 | Bolduc et al. |
| 7,494,499 B2 | 2/2009 | Nagase et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,517,356 B2 | 4/2009 | Heinrich |
| 7,547,312 B2 | 6/2009 | Bauman et al. |
| 7,549,564 B2 | 6/2009 | Boudreaux |
| 7,549,998 B2 | 6/2009 | Braun |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,648,519 B2 | 1/2010 | Lee et al. |
| 7,658,311 B2 | 2/2010 | Boudreaux |
| 7,662,161 B2 | 2/2010 | Briganti et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,686,201 B2 | 3/2010 | Csiky |
| 7,686,826 B2 | 3/2010 | Lee et al. |
| 7,691,098 B2 | 4/2010 | Wallace et al. |
| 7,699,844 B2 | 4/2010 | Utley et al. |
| 7,699,859 B2 | 4/2010 | Bombard et al. |
| 7,708,181 B2 | 5/2010 | Cole et al. |
| 7,708,758 B2 | 5/2010 | Lee et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,731,072 B2 | 6/2010 | Timm et al. |
| 7,735,703 B2 | 6/2010 | Morgan et al. |
| 7,736,306 B2 | 6/2010 | Brustad et al. |
| 7,738,971 B2 | 6/2010 | Swayze et al. |
| 7,740,159 B2 | 6/2010 | Shelton, IV et al. |
| 7,744,624 B2 | 6/2010 | Bettuchi |
| 7,744,628 B2 | 6/2010 | Viola |

(56) References Cited

U.S. PATENT DOCUMENTS

| | | |
|---|---|---|
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,776,060 B2 | 8/2010 | Mooradian et al. |
| 7,780,685 B2 | 8/2010 | Hunt et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,426 B2 | 11/2010 | Racenet et al. |
| 7,828,808 B2 | 11/2010 | Hinman et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,842,028 B2 | 11/2010 | Lee |
| 7,845,537 B2 | 12/2010 | Shelton, IV et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,871,418 B2 | 1/2011 | Thompson et al. |
| 7,879,070 B2 | 2/2011 | Ortiz et al. |
| 7,883,461 B2 | 2/2011 | Albrecht et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,914,543 B2 | 3/2011 | Roth et al. |
| 7,918,377 B2 | 4/2011 | Measamer et al. |
| 7,922,061 B2 | 4/2011 | Shelton, IV et al. |
| 7,922,743 B2 | 4/2011 | Heinrich et al. |
| 7,934,630 B2 | 5/2011 | Shelton, IV et al. |
| 7,942,890 B2 | 5/2011 | D'Agostino et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,955,253 B2 | 6/2011 | Ewers et al. |
| 7,955,257 B2 | 6/2011 | Frasier et al. |
| 7,959,051 B2 | 6/2011 | Smith et al. |
| 7,966,799 B2 | 6/2011 | Morgan et al. |
| 7,980,443 B2 | 7/2011 | Scheib et al. |
| 7,981,132 B2 | 7/2011 | Dubrul et al. |
| 8,002,696 B2 | 8/2011 | Suzuki |
| 8,002,795 B2 | 8/2011 | Beetel |
| 8,016,855 B2 | 9/2011 | Whitman et al. |
| 8,016,858 B2 | 9/2011 | Whitman |
| 8,020,743 B2 | 9/2011 | Shelton, IV |
| 8,034,077 B2 | 10/2011 | Smith et al. |
| 8,043,328 B2 | 10/2011 | Hahnen et al. |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,097,017 B2 | 1/2012 | Viola |
| 8,105,350 B2 | 1/2012 | Lee et al. |
| 8,113,410 B2 | 2/2012 | Hall et al. |
| 8,114,100 B2 | 2/2012 | Smith et al. |
| 8,123,767 B2 | 2/2012 | Bauman et al. |
| 8,128,645 B2 | 3/2012 | Sonnenschein et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,211,125 B2 | 7/2012 | Spivey |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,226,553 B2 | 7/2012 | Shelton, IV et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,267,300 B2 | 9/2012 | Boudreaux |
| 8,287,561 B2 | 10/2012 | Nunez et al. |
| 8,292,155 B2 | 10/2012 | Shelton, IV et al. |
| 8,308,040 B2 | 11/2012 | Huang et al. |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,348,129 B2 | 1/2013 | Bedi et al. |
| 8,348,131 B2 | 1/2013 | Omaits et al. |
| 8,348,837 B2 | 1/2013 | Wenchell |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,365,976 B2 | 2/2013 | Hess et al. |
| 8,371,491 B2 | 2/2013 | Huitema et al. |
| 8,372,094 B2 | 2/2013 | Bettuchi et al. |
| 8,393,514 B2 | 3/2013 | Shelton, IV et al. |
| 8,397,971 B2 | 3/2013 | Yates et al. |
| 8,398,669 B2 | 3/2013 | Kim |
| 8,408,439 B2 | 4/2013 | Huang et al. |
| 8,409,079 B2 | 4/2013 | Okamoto et al. |
| 8,414,577 B2 | 4/2013 | Boudreaux et al. |
| 8,424,740 B2 | 4/2013 | Shelton, IV et al. |
| 8,444,036 B2 | 5/2013 | Shelton, IV |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,923 B2 | 6/2013 | Shelton, IV |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,937 B2 | 11/2013 | Gresham |
| 8,584,919 B2 | 11/2013 | Hueil et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |

(56) References Cited

U.S. PATENT DOCUMENTS

| | | | |
|---|---|---|---|
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 2002/0095175 A1 | 7/2002 | Brock et al. |
| 2003/0220660 A1 | 11/2003 | Kortenbach et al. |
| 2004/0006372 A1 | 1/2004 | Racenet et al. |
| 2004/0097987 A1 | 5/2004 | Pugsley et al. |
| 2004/0098040 A1 | 5/2004 | Taniguchi et al. |
| 2004/0111081 A1 | 6/2004 | Whitman et al. |
| 2004/0147909 A1 | 7/2004 | Johnston et al. |
| 2004/0167572 A1 | 8/2004 | Roth et al. |
| 2004/0193177 A1 | 9/2004 | Houghton et al. |
| 2004/0193189 A1 | 9/2004 | Kortenbach et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0033357 A1 | 2/2005 | Braun |
| 2005/0059997 A1 | 3/2005 | Bauman et al. |
| 2005/0070929 A1 | 3/2005 | Dalessandro et al. |
| 2005/0085693 A1 | 4/2005 | Belson et al. |
| 2005/0107824 A1 | 5/2005 | Hillstead et al. |
| 2005/0131390 A1 | 6/2005 | Heinrich et al. |
| 2005/0131457 A1 | 6/2005 | Douglas et al. |
| 2005/0177181 A1 | 8/2005 | Kagan et al. |
| 2005/0182298 A1 | 8/2005 | Ikeda et al. |
| 2005/0187576 A1 | 8/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0240222 A1 | 10/2005 | Shipp |
| 2005/0256452 A1 | 11/2005 | DeMarchi et al. |
| 2006/0020258 A1 | 1/2006 | Strauss et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047303 A1 | 3/2006 | Ortiz et al. |
| 2006/0047307 A1 | 3/2006 | Ortiz et al. |
| 2006/0052825 A1 | 3/2006 | Ransick et al. |
| 2006/0085033 A1 | 4/2006 | Criscuolo et al. |
| 2006/0161185 A1 | 7/2006 | Saadat et al. |
| 2006/0173470 A1 | 8/2006 | Oray et al. |
| 2006/0201989 A1* | 9/2006 | Ojeda ........................ 227/175.1 |
| 2006/0212069 A1 | 9/2006 | Shelton, IV |
| 2006/0235368 A1 | 10/2006 | Oz |
| 2006/0235469 A1 | 10/2006 | Viola |
| 2006/0241692 A1 | 10/2006 | McGuckin, Jr. et al. |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0271102 A1 | 11/2006 | Bosshard et al. |
| 2007/0027468 A1 | 2/2007 | Wales et al. |
| 2007/0027469 A1 | 2/2007 | Smith et al. |
| 2007/0043387 A1 | 2/2007 | Vargas et al. |
| 2007/0055219 A1 | 3/2007 | Whitman et al. |
| 2007/0066981 A1 | 3/2007 | Meagher |
| 2007/0073341 A1 | 3/2007 | Smith et al. |
| 2007/0078484 A1 | 4/2007 | Talarico et al. |
| 2007/0093869 A1 | 4/2007 | Bloom et al. |
| 2007/0102472 A1 | 5/2007 | Shelton, IV |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0170225 A1 | 7/2007 | Shelton, IV et al. |
| 2007/0173687 A1 | 7/2007 | Shima et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0219571 A1 | 9/2007 | Balbierz et al. |
| 2007/0225562 A1 | 9/2007 | Spivey et al. |
| 2007/0239028 A1 | 10/2007 | Houser et al. |
| 2007/0244471 A1 | 10/2007 | Malackowski |
| 2007/0270784 A1 | 11/2007 | Smith et al. |
| 2007/0276189 A1 | 11/2007 | Abel et al. |
| 2007/0299427 A1 | 12/2007 | Yeung et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0140115 A1 | 6/2008 | Stopek |
| 2008/0154299 A1 | 6/2008 | Livneh |
| 2008/0167522 A1 | 7/2008 | Giordano et al. |
| 2008/0169328 A1 | 7/2008 | Shelton |
| 2008/0169329 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0242939 A1 | 10/2008 | Johnston |
| 2008/0255413 A1 | 10/2008 | Zemlok et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0149871 A9 | 6/2009 | Kagan et al. |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2009/0292176 A1 | 11/2009 | Bonadio et al. |
| 2010/0069942 A1 | 3/2010 | Shelton, IV |
| 2010/0076475 A1 | 3/2010 | Yates et al. |
| 2010/0087840 A1 | 4/2010 | Ebersole et al. |
| 2010/0133317 A1 | 6/2010 | Shelton, IV et al. |
| 2010/0179382 A1 | 7/2010 | Shelton, IV et al. |
| 2010/0193566 A1 | 8/2010 | Scheib et al. |
| 2010/0222901 A1 | 9/2010 | Swayze et al. |
| 2010/0228091 A1 | 9/2010 | Widenhouse et al. |
| 2010/0243709 A1 | 9/2010 | Hess et al. |
| 2010/0249519 A1 | 9/2010 | Park et al. |
| 2010/0292540 A1 | 11/2010 | Hess et al. |
| 2010/0294829 A1 | 11/2010 | Giordano et al. |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0060363 A1 | 3/2011 | Hess et al. |

(56) References Cited

U.S. PATENT DOCUMENTS

| | | |
|---|---|---|
| 2011/0068148 A1 | 3/2011 | Hall et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0114700 A1 | 5/2011 | Baxter, III et al. |
| 2011/0125176 A1 | 5/2011 | Yates et al. |
| 2011/0125177 A1 | 5/2011 | Yates et al. |
| 2011/0132964 A1 | 6/2011 | Weisenburgh, II et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0174861 A1 | 7/2011 | Shelton, IV et al. |
| 2011/0174862 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV et al. |
| 2012/0199632 A1 | 8/2012 | Spivey et al. |
| 2012/0203247 A1 | 8/2012 | Shelton, IV et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0283707 A1 | 11/2012 | Giordano et al. |
| 2012/0283748 A1 | 11/2012 | Ortiz et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2012/0298722 A1 | 11/2012 | Hess et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0012931 A1 | 1/2013 | Spivey et al. |
| 2013/0012957 A1 | 1/2013 | Shelton, IV et al. |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0105551 A1 | 5/2013 | Zingman |
| 2013/0116668 A1 | 5/2013 | Shelton, IV et al. |
| 2013/0116669 A1 | 5/2013 | Shelton, IV et al. |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153636 A1 | 6/2013 | Shelton, IV et al. |
| 2013/0153641 A1 | 6/2013 | Shelton, IV et al. |
| 2013/0161375 A1 | 6/2013 | Huitema et al. |

(56) References Cited

U.S. PATENT DOCUMENTS

| | | |
|---|---|---|
| 2013/0168435 A1 | 7/2013 | Huang et al. |
| 2013/0172929 A1 | 7/2013 | Hess et al. |
| 2013/0175317 A1 | 7/2013 | Yates et al. |
| 2013/0175321 A1 | 7/2013 | Shelton, IV et al. |
| 2013/0175322 A1 | 7/2013 | Yates et al. |
| 2013/0181030 A1 | 7/2013 | Hess et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0200132 A1 | 8/2013 | Moore et al. |
| 2013/0206814 A1 | 8/2013 | Morgan et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0248577 A1 | 9/2013 | Leimbach et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0000411 A1 | 1/2014 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005661 A1 | 1/2014 | Shelton, IV et al. |
| 2014/0005662 A1 | 1/2014 | Shelton, IV |
| 2014/0005676 A1 | 1/2014 | Shelton, IV et al. |
| 2014/0005677 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005680 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |

FOREIGN PATENT DOCUMENTS

| | | |
|---|---|---|
| CA | 2512960 A1 | 1/2006 |
| CA | 2514274 A1 | 1/2006 |
| CN | 2488482 Y | 5/2002 |
| CN | 1523725 A | 8/2004 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| CN | 101023879 B | 3/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0879742 A1 | 11/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |

(56) References Cited

FOREIGN PATENT DOCUMENTS

| | | | |
|---|---|---|---|
| EP | 0711611 | A2 | 5/1996 |
| EP | 0484677 | B2 | 6/1996 |
| EP | 0541987 | B1 | 7/1996 |
| EP | 0667119 | B1 | 7/1996 |
| EP | 0748614 | A1 | 12/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0603472 | B1 | 11/1998 |
| EP | 0605351 | B1 | 11/1998 |
| EP | 0878169 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0843906 | B1 | 3/2000 |
| EP | 0552050 | B1 | 5/2000 |
| EP | 0833592 | B1 | 5/2000 |
| EP | 0832605 | B1 | 6/2000 |
| EP | 0830094 | B1 | 9/2000 |
| EP | 1034747 | A1 | 9/2000 |
| EP | 1034748 | A1 | 9/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 0717960 | B1 | 2/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1011494 | B1 | 1/2007 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1800610 | A1 | 6/2007 |
| EP | 1300117 | B1 | 8/2007 |
| EP | 1813199 | A1 | 8/2007 |

(56) References Cited

FOREIGN PATENT DOCUMENTS

| | | |
|---|---|---|
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 1719461 B1 | 6/2009 |
| EP | 1834594 B1 | 6/2009 |
| EP | 1745748 B1 | 8/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 1994890 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2314254 A2 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 2153781 B1 | 11/2011 |
| EP | 1847225 B1 | 12/2011 |
| EP | 1785102 B1 | 1/2012 |
| EP | 2090253 B1 | 3/2012 |
| EP | 1813204 B1 | 7/2012 |
| EP | 2189121 B1 | 7/2012 |
| EP | 2005895 B1 | 8/2012 |
| EP | 2090248 B1 | 8/2012 |
| EP | 2481359 A1 | 8/2012 |
| EP | 2090252 B1 | 10/2012 |
| EP | 2517637 A1 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 B1 | 4/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| GR | 930100110 A | 11/1993 |
| JP | 50-33988 U | 4/1975 |
| JP | S 58500053 A | 1/1983 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 05-084242 A | 4/1993 |
| JP | H 05-084252 A | 4/1993 |
| JP | 5-212039 A | 8/1993 |
| JP | 6007357 A | 1/1994 |
| JP | H 6-30945 A | 2/1994 |
| JP | H 06-26812 U | 4/1994 |
| JP | H 6-121798 A | 5/1994 |
| JP | 7051273 A | 2/1995 |
| JP | 7-124166 A | 5/1995 |
| JP | 07-171163 | 7/1995 |
| JP | 7-255735 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |

(56) References Cited

FOREIGN PATENT DOCUMENTS

| | | |
|---|---|---|
| JP | 8229050 A | 9/1996 |
| JP | H 09-501081 A | 2/1997 |
| JP | H 09-501577 A | 2/1997 |
| JP | H 09-164144 (A) | 6/1997 |
| JP | H 10-118090 (A) | 5/1998 |
| JP | H 10-512469 | 12/1998 |
| JP | 2000-14632 | 1/2000 |
| JP | 2000033071 A | 2/2000 |
| JP | 2000-112002 A | 4/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001-517473 A | 10/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-164066 | 6/2003 |
| JP | 2003-521301 A | 7/2003 |
| JP | 2004-162035 A | 6/2004 |
| JP | 2004-229976 A | 8/2004 |
| JP | 2004-531280 A | 10/2004 |
| JP | 2004-532084 A | 10/2004 |
| JP | 2004-532676 (A) | 10/2004 |
| JP | 2004-4532676 (A) | 10/2004 |
| JP | 2004-329624 A | 11/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 T | 2/2005 |
| JP | 2005-103280 A | 4/2005 |
| JP | 2005-103281 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2005-335432 A | 12/2005 |
| JP | 2006-034975 A | 2/2006 |
| JP | 2006-34977 A | 2/2006 |
| JP | 2006-034980 A | 2/2006 |
| JP | 2006-506106 A | 2/2006 |
| JP | 2006-187649 A | 7/2006 |
| JP | 2006-218297 A | 8/2006 |
| JP | 2006-281405 A | 10/2006 |
| JP | 2006-346445 A | 12/2006 |
| JP | 2007-61628 A | 3/2007 |
| JP | 2007-098130 A | 4/2007 |
| JP | 3906843 B2 | 4/2007 |
| JP | 2007-117725 A | 5/2007 |
| JP | 2007-222615 A | 6/2007 |
| JP | 2007-203051 A | 8/2007 |
| JP | 2007-203057 A | 8/2007 |
| JP | 2007/524435 A | 8/2007 |
| JP | 2007-229448 A | 9/2007 |
| JP | 2007-325922 A | 12/2007 |
| JP | 2008-68073 A | 3/2008 |
| JP | 2008-283459 A | 11/2008 |
| JP | 2009-506799 A | 2/2009 |
| JP | 2009-106752 A | 5/2009 |
| JP | 2009-539420 A | 11/2009 |
| JP | 2010-098844 A | 4/2010 |
| RU | 1814161 A1 | 5/1993 |
| RU | 2008830 C1 | 3/1994 |
| RU | 2141279 C1 | 11/1999 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94-24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |

(56) References Cited

FOREIGN PATENT DOCUMENTS

| | | |
|---|---|---|
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A2 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A2 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |

(56) References Cited

FOREIGN PATENT DOCUMENTS

| | | |
|---|---|---|
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/023851 A1 | 2/2009 |
| WO | WO 2009/046394 A1 | 4/2009 |
| WO | WO 2009/137761 A2 | 11/2009 |
| WO | WO 2009/143092 A1 | 11/2009 |
| WO | WO 2009/143331 A1 | 11/2009 |
| WO | WO 2010/028332 A2 | 3/2010 |
| WO | WO 2010/030434 A1 | 3/2010 |
| WO | WO 2010/054404 A1 | 5/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044551 A1 | 4/2012 |
| WO | WO 2012/044820 A1 | 4/2012 |
| WO | WO 2012/044844 A2 | 4/2012 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell- synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIS™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 30-12.

Hoffman, "Hydrogels for Biomedical Applications," Advanced Drug Delivery Reviews, 54 (2002) pp. 30-12.

Peppas, "Physiologically Responsive Hydrogels," Journal of Bioactive and Compatible Polymers, vol. 6 (Jul. 1991) pp. 241-246.

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

Peppas, Editor "Hydrogels in Medicine and Pharmacy," vol. I, Fundamentals, CRC Press, 1986.

International Preliminary Report on Patentability for PCT/US2012/028886, Sep. 17, 2013 (12 pages).

* cited by examiner

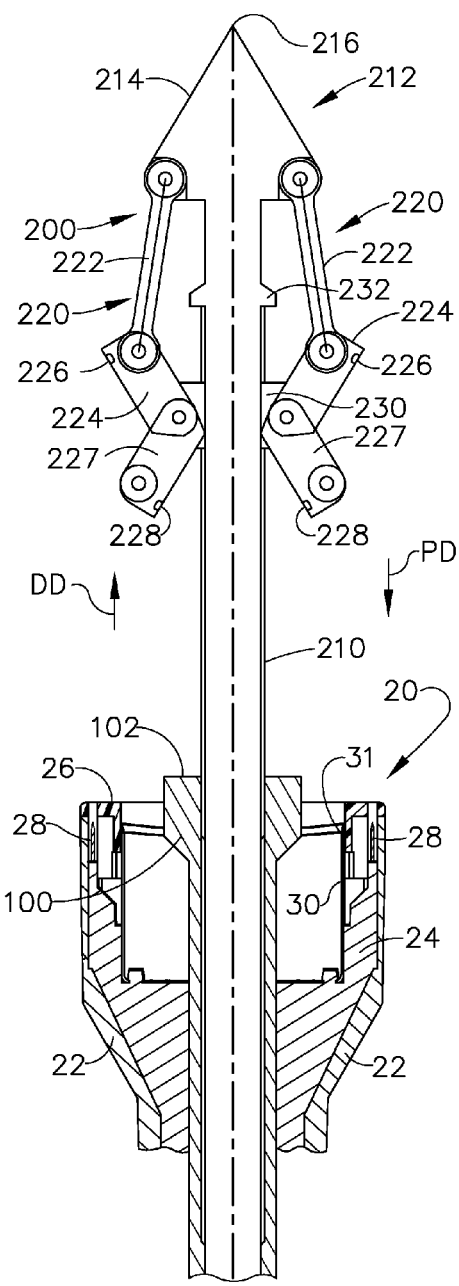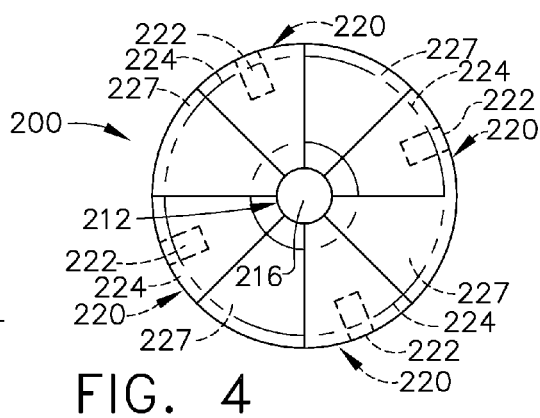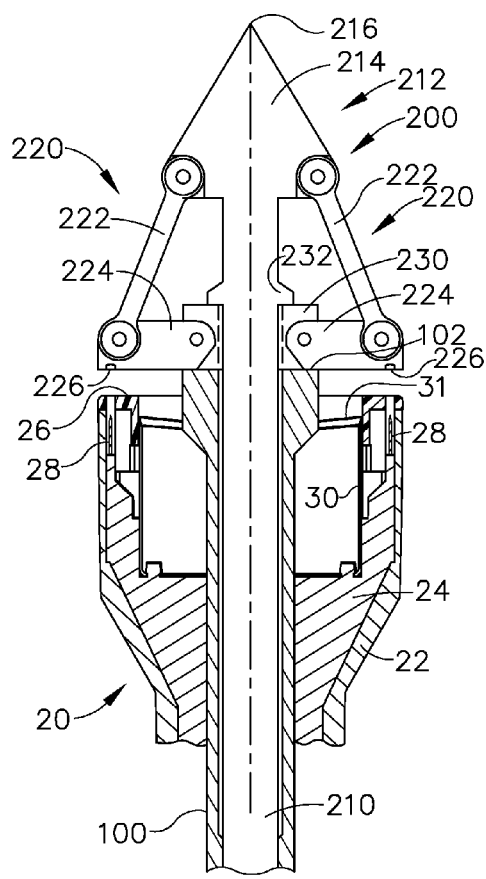
FIG. 2
FIG. 4
FIG. 3

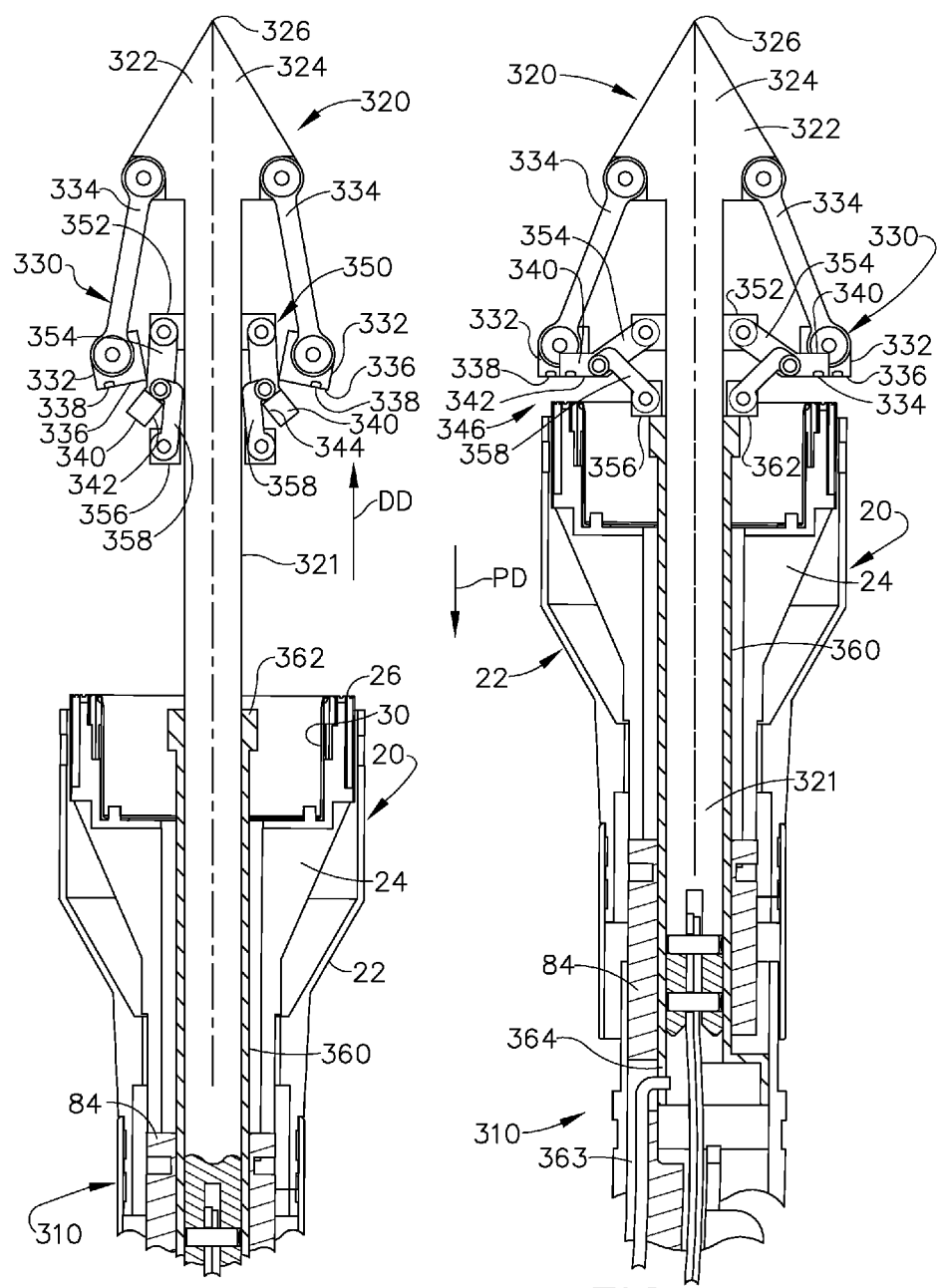

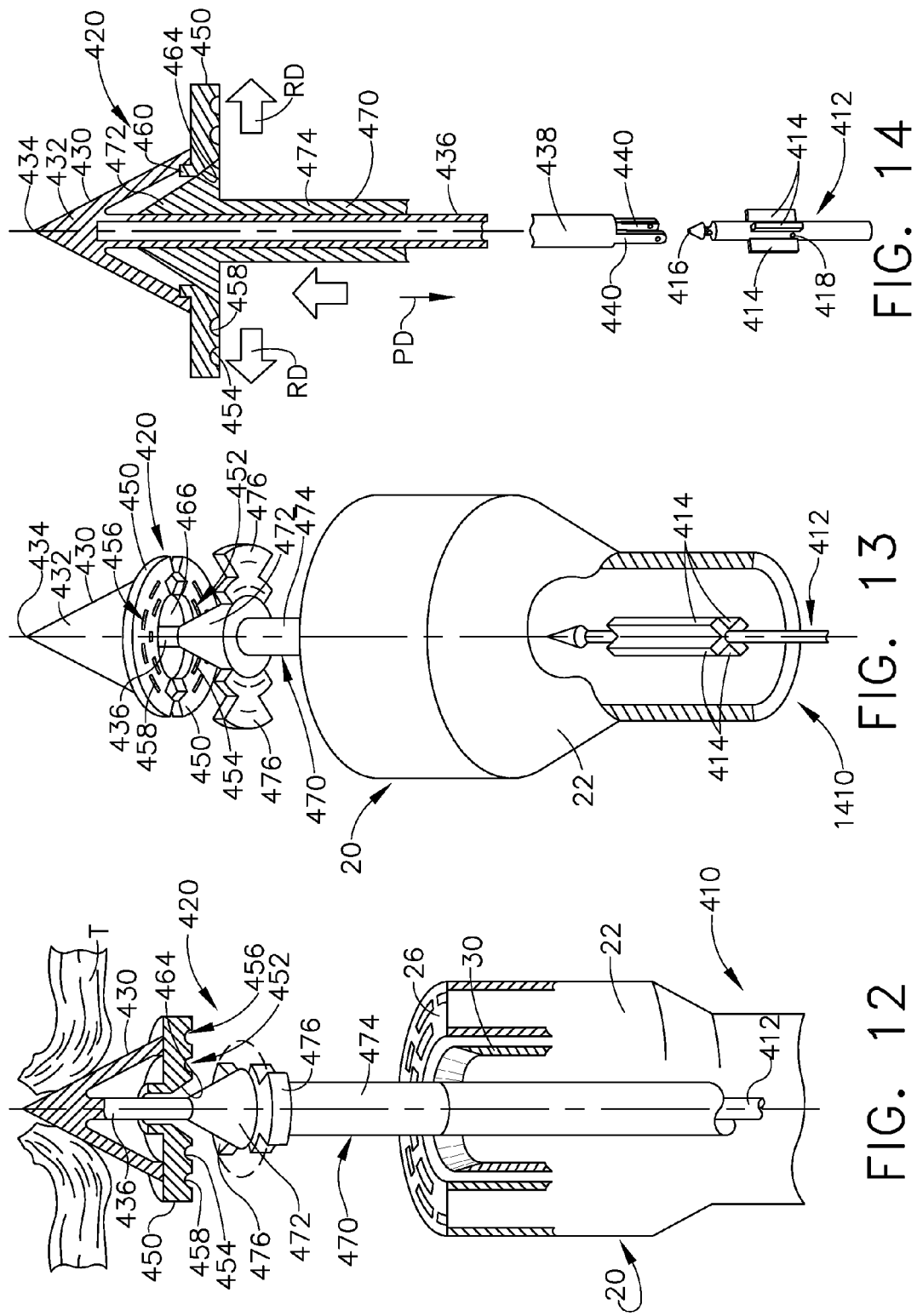

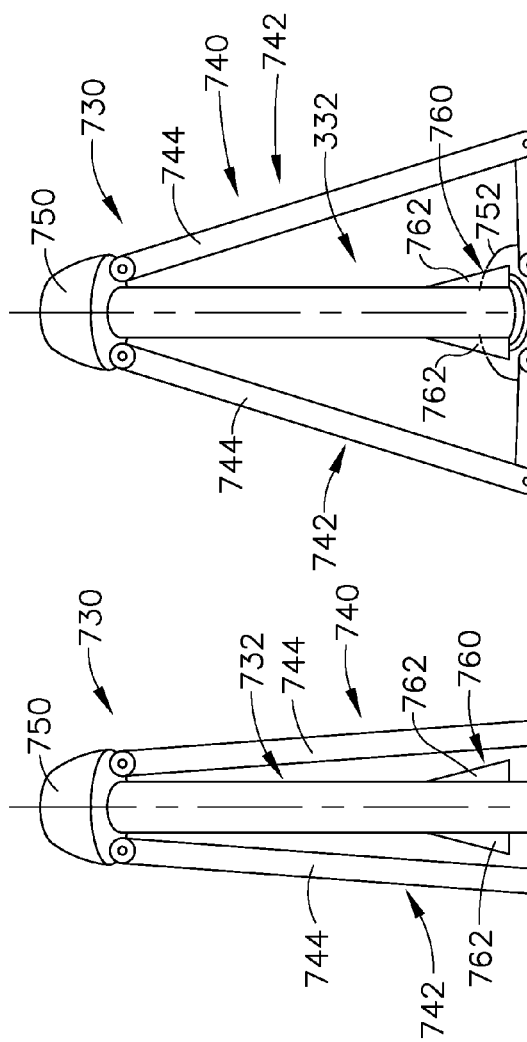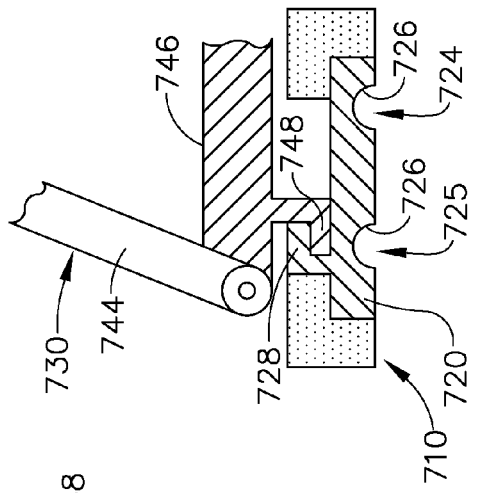

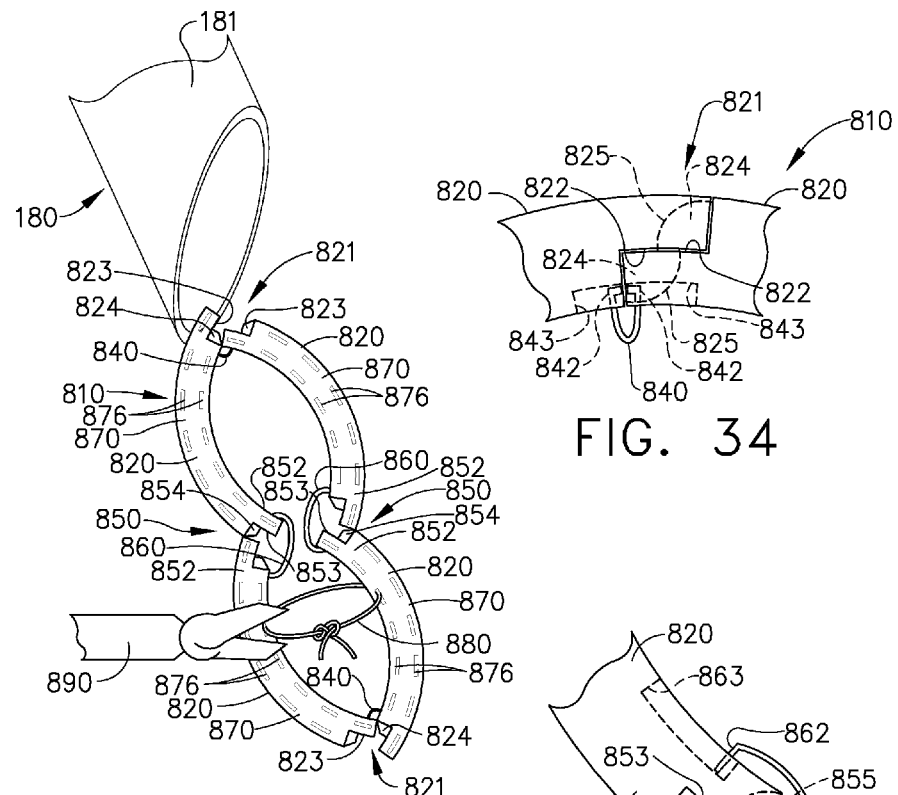
FIG. 32
FIG. 34
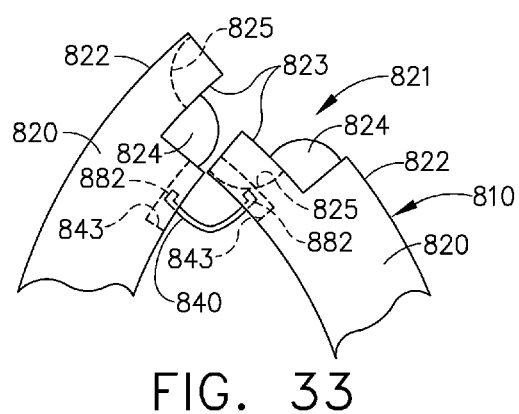
FIG. 33
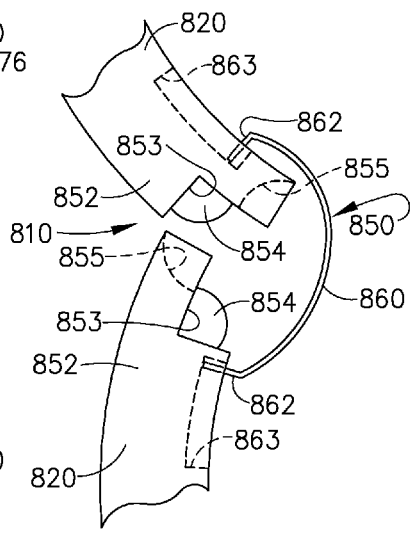
FIG. 35

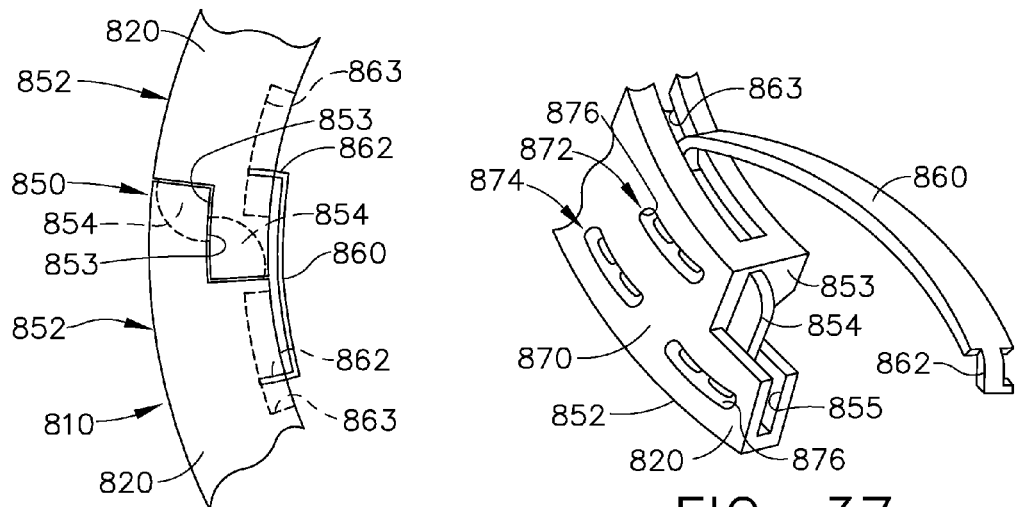
FIG. 36
FIG. 37
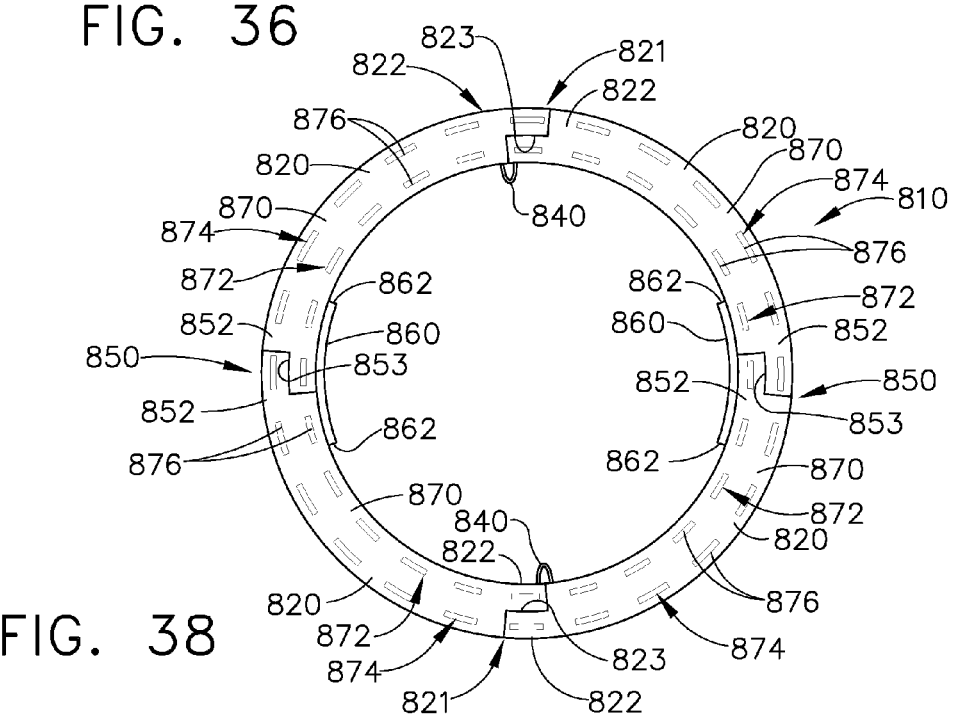
FIG. 38

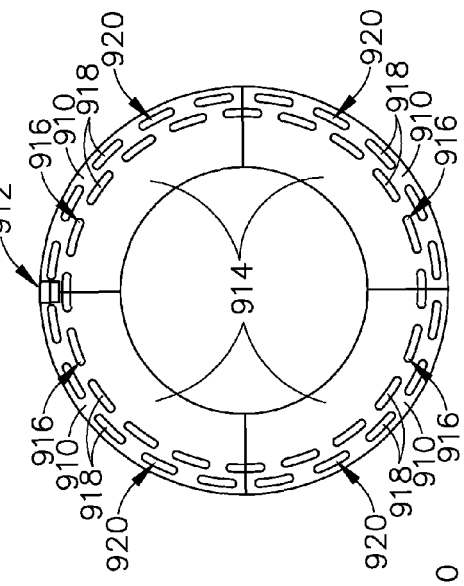
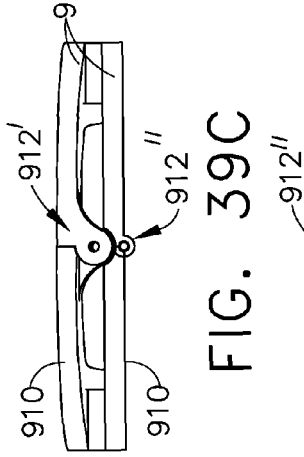
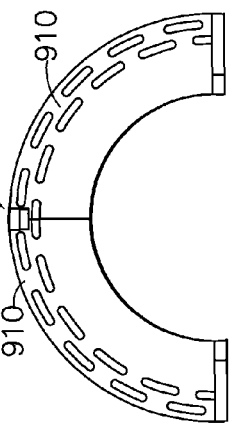
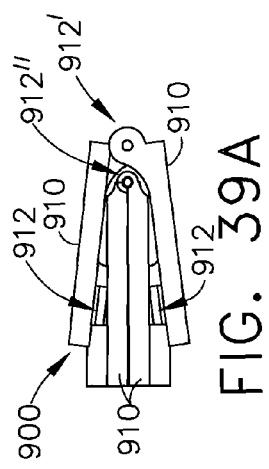
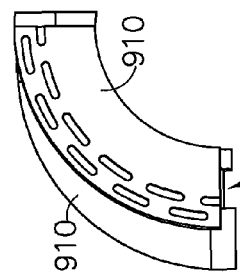

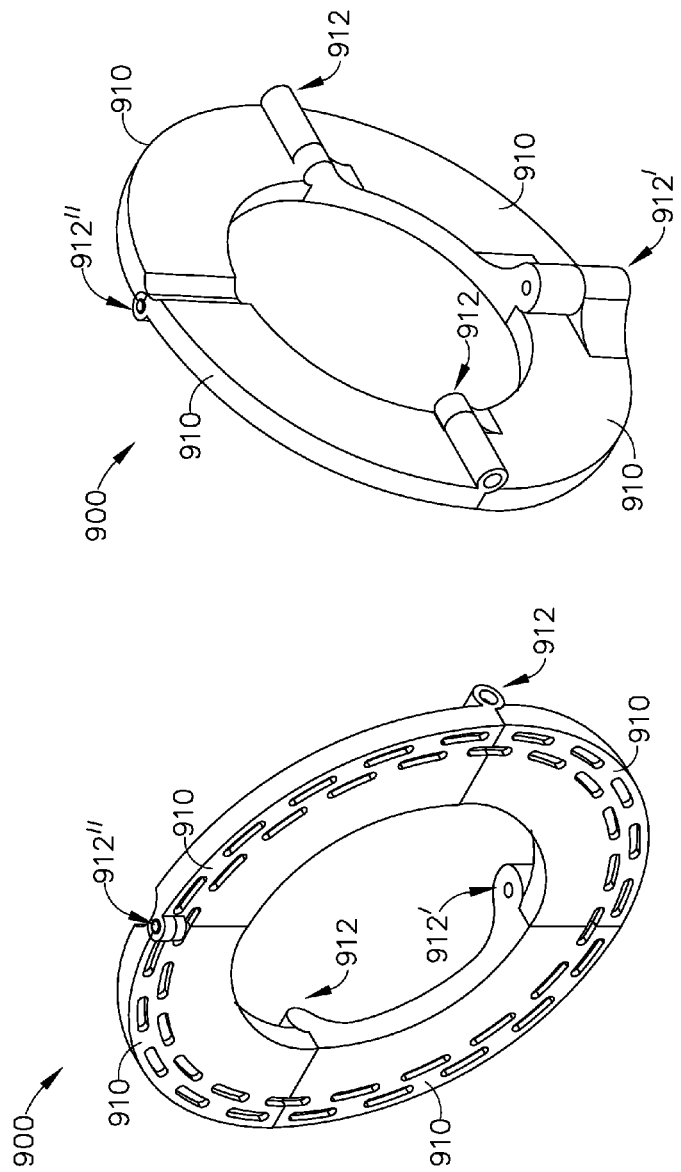

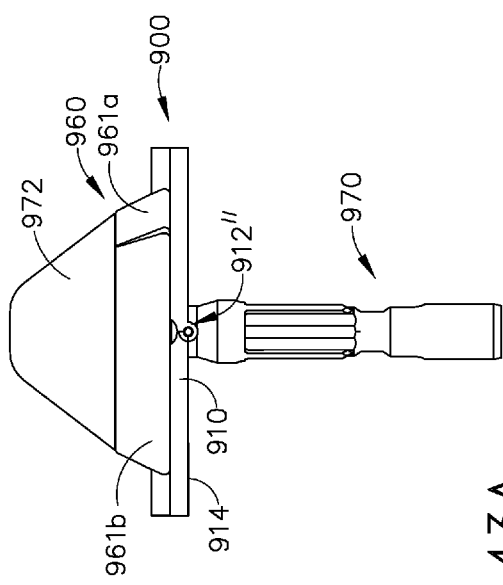
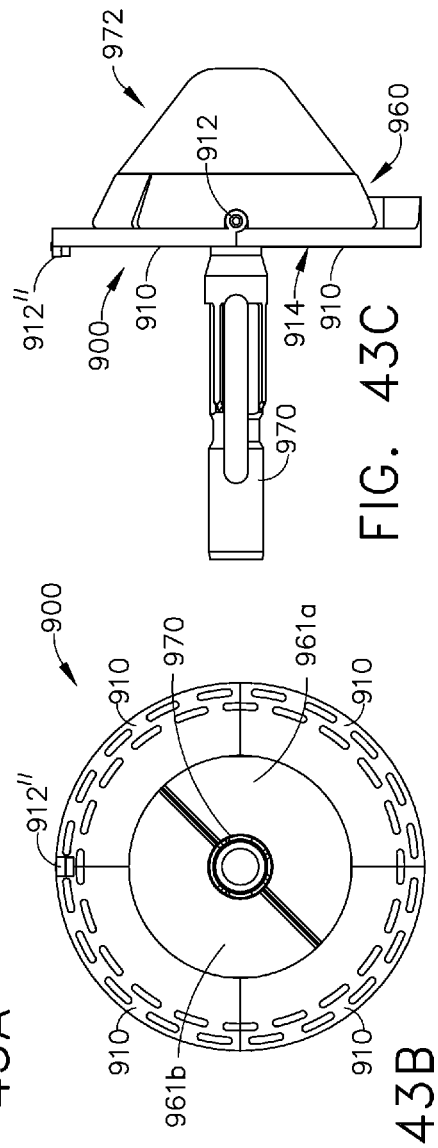
FIG. 43A
FIG. 43B
FIG. 43C

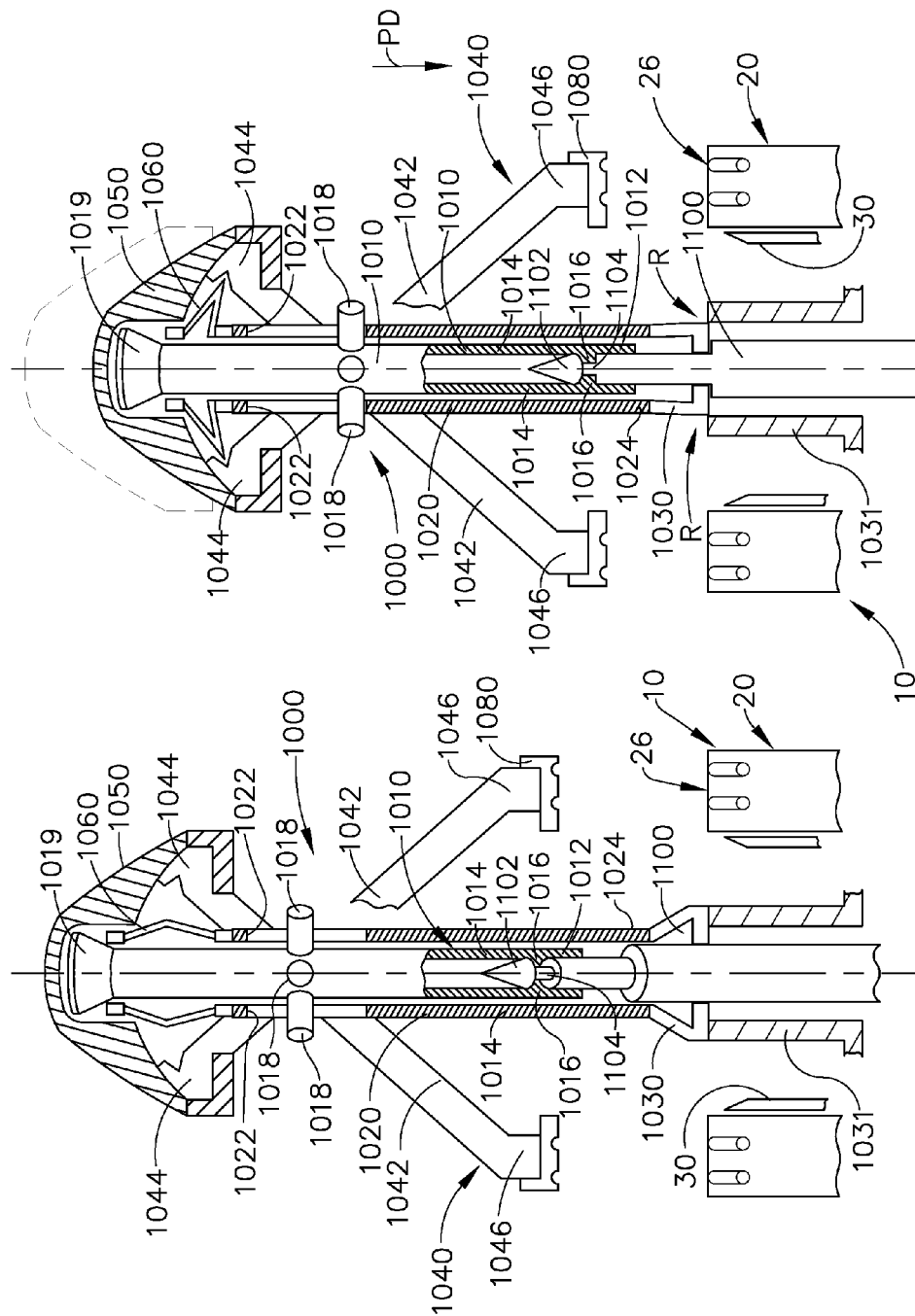

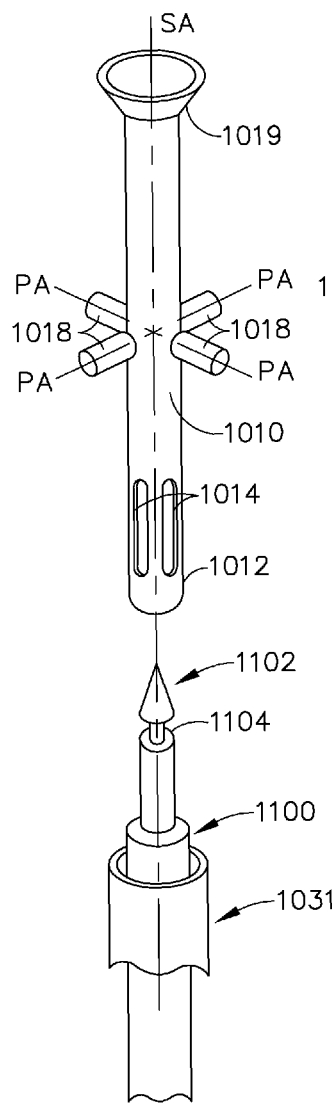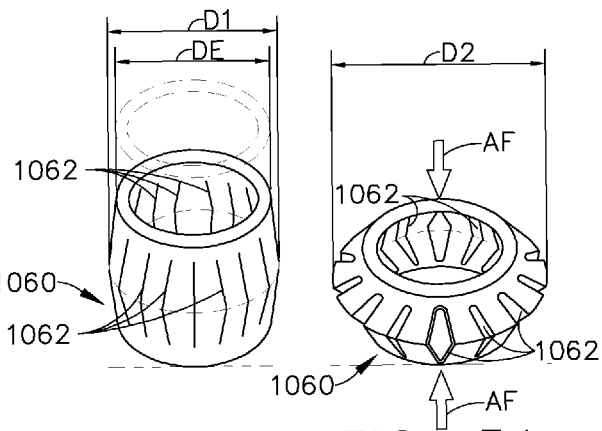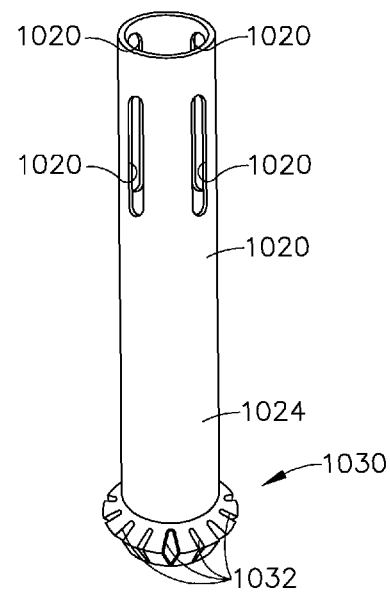
FIG. 48    FIG. 49    FIG. 50    FIG. 51

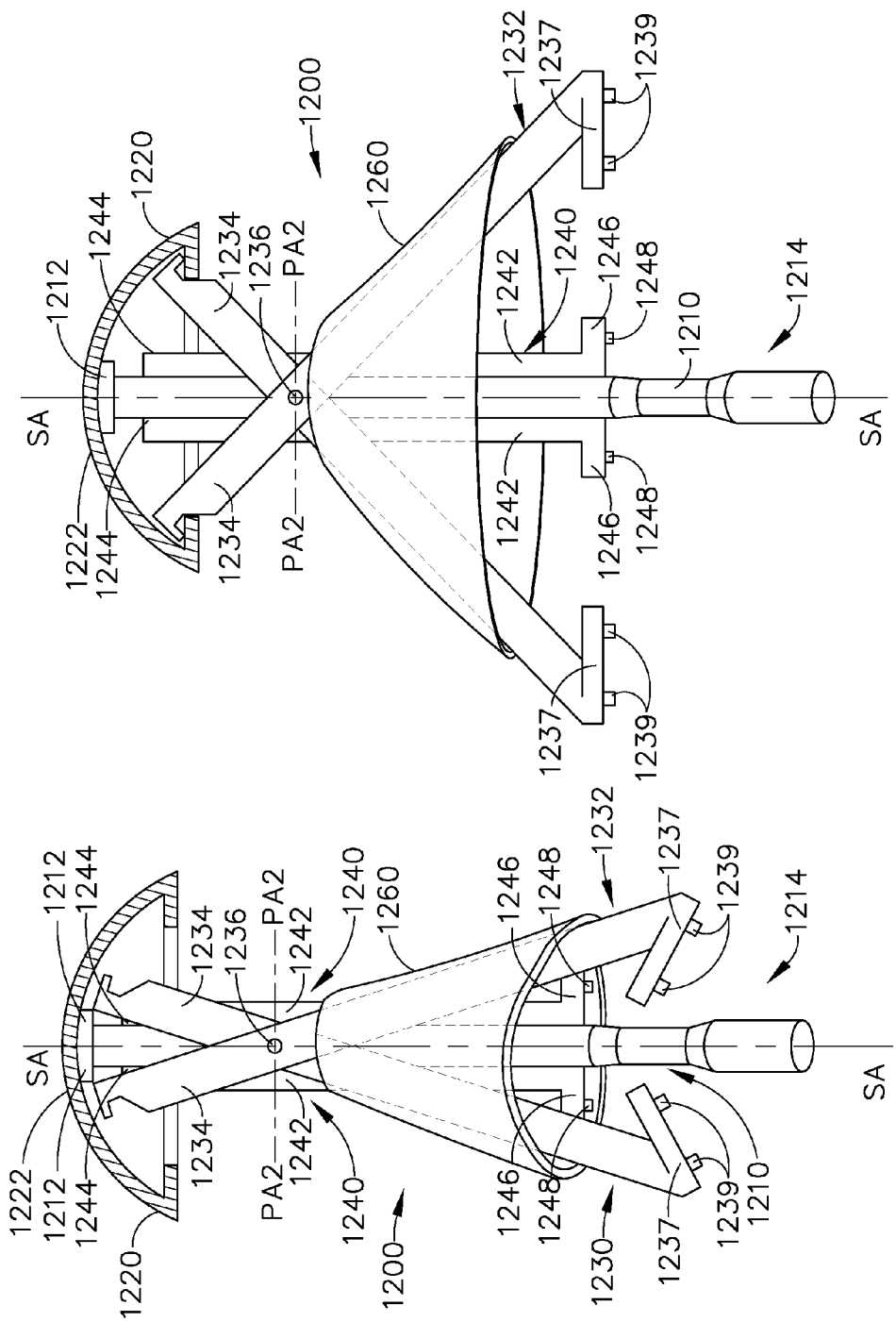

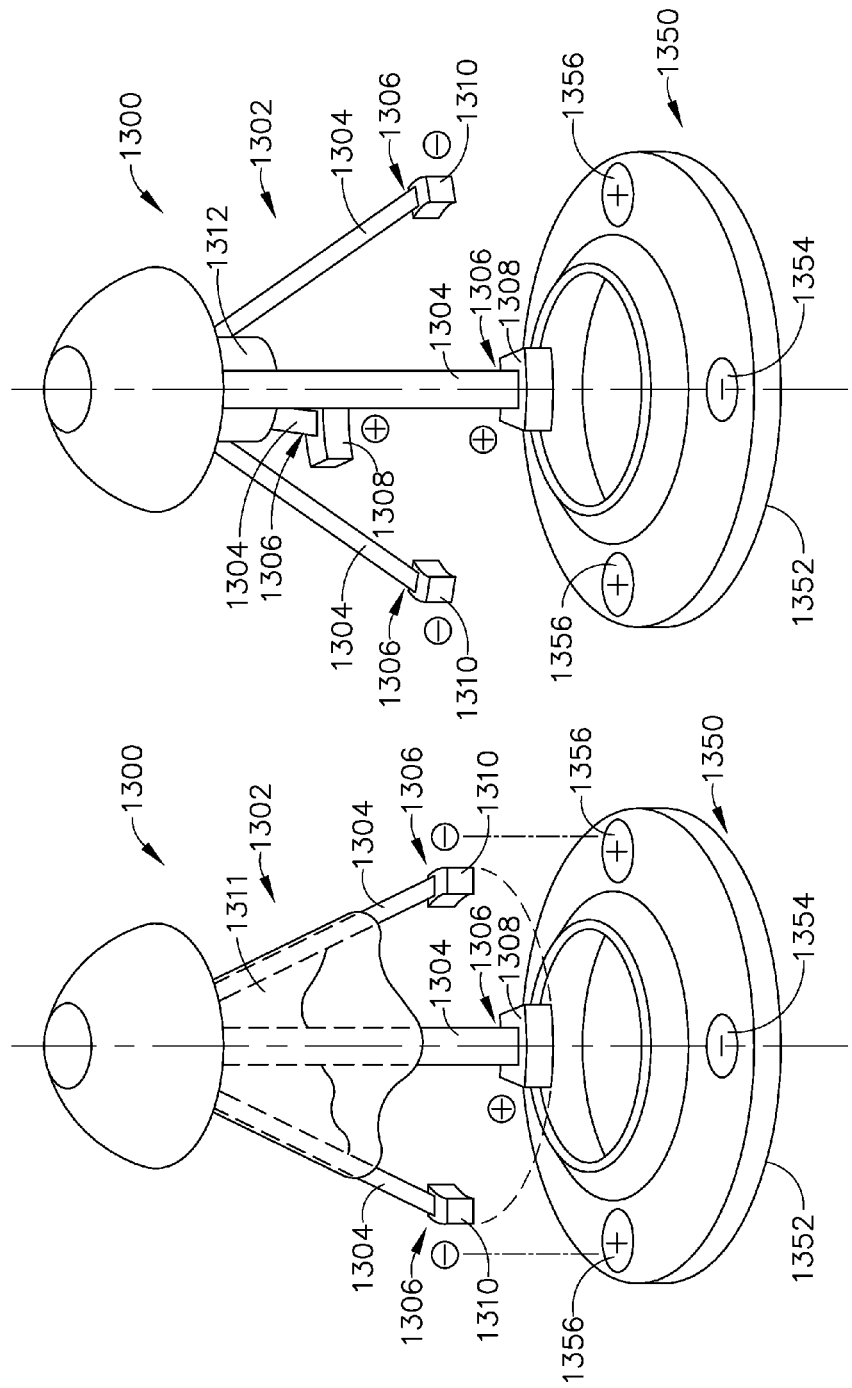

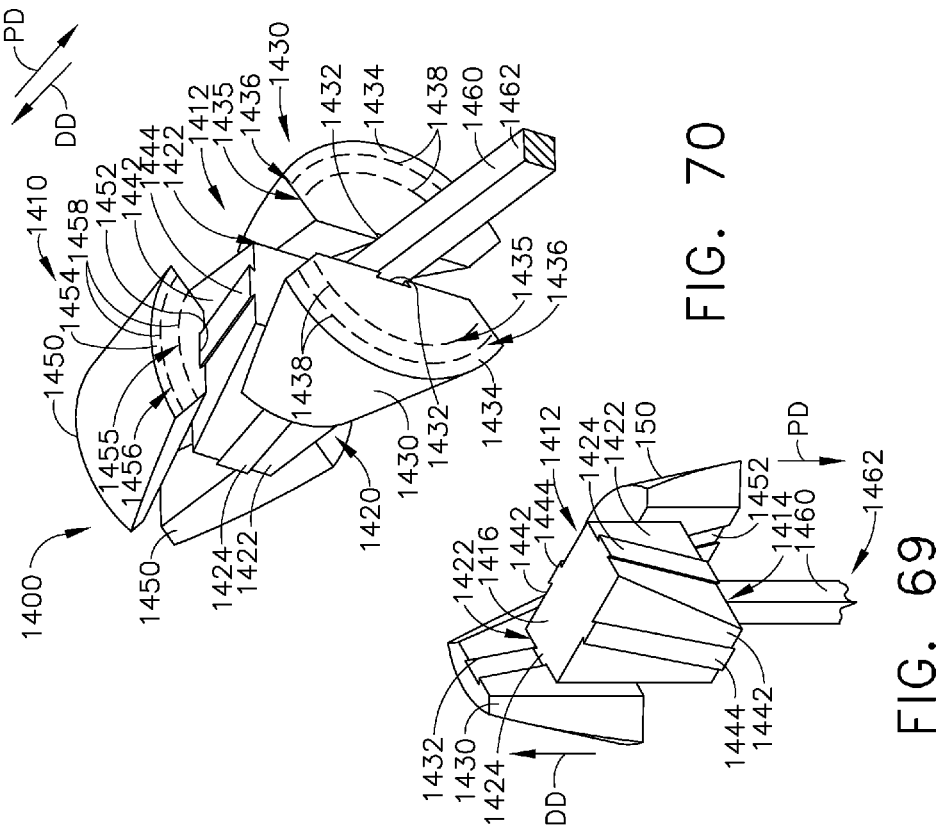
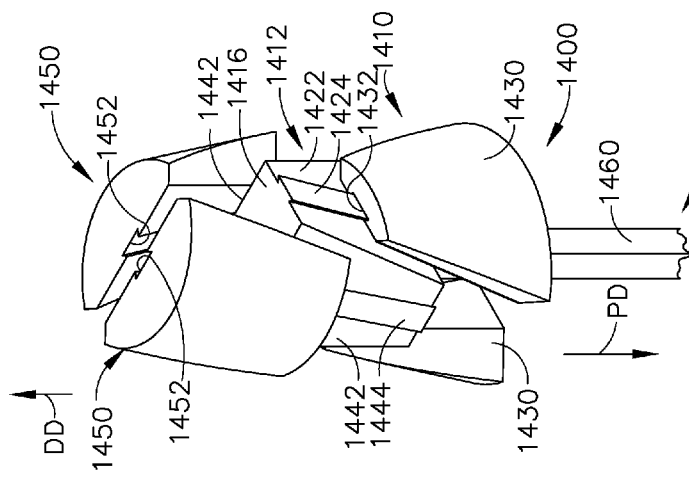
FIG. 68
FIG. 69
FIG. 70

COLLAPSIBLE ANVIL PLATE ASSEMBLIES FOR CIRCULAR SURGICAL STAPLING DEVICES

CROSS-REFERENCE TO RELATED APPLICATIONS

This non-provisional patent application claims the benefit of and priority from U.S. Provisional Patent Application Ser. No. 61/452,432, filed Mar. 14, 2011, entitled "Surgical Stapling Instruments", the entire disclosure of which is hereby incorporated by reference.

FIELD OF THE INVENTION

The present invention generally relates to surgical procedures and surgical instruments for completing such procedures, and more particularly, to surgical stapling devices and methods of use.

BACKGROUND

Obesity is one of the fastest growing health problems in the world. For example, the Center for Disease Control estimates that over 20% of the U.S. population is obese. Gastric bypass surgery has been found to be one of the most effective treatments for morbid obesity.

Several different gastric bypass surgeries exist. The most common gastric bypass surgery is a Roux-en-Y gastric bypass. In a Roux-en-Y gastric bypass, the stomach is made smaller by creating a small pouch at the top of the stomach using surgical staples. The smaller stomach is connected to the middle portion of the small intestine (jejunum), bypassing the rest of the stomach and the upper portion of the small intestine (duodenum). The procedure can be done by making a large incision in the abdomen (an open procedure) or by making a small incision and using small instruments and a camera to guide the surgery (a laparoscopic procedure). Laparoscopic procedures generally result in quicker recoveries and shorter hospital stays. The risk associated with wound infection is significantly reduced and patients generally report less pain and experience a quicker return to normal activity.

When performing Roux-en-Y gastric bypass surgery laparoscopically, a number of conventional trocar devices are placed in various locations through the abdominal wall to provide passages through which surgical instruments, grasping devices and cameras may be inserted. As indicated above, such procedure involves the creation of a small stomach pouch and the attachment of the jejunum thereto by means of an anastomosis (commonly referred to as the G-J anastomosis). The jejunum portion is then reattached to the middle portion of the jejunum by another anastomosis (commonly referred to as the J-J anastomosis). Such arrangement therefore bypasses the severed portion of stomach and duodenum.

The circular stapler is an essential tool for construction of gastrointestinal anastomosis. Circular staplers useful for performing such procedures are disclosed, for example, in U.S. Pat. Nos. 5,104,025; 5,205,459; 5,285,945; and 5,309,927 which are each herein incorporated by reference in their respective entireties. In general, a conventional circular stapler typically consists of an elongated shaft that has a proximal actuating mechanism and a distal stapling mechanism mounted to the elongated shaft. The distal stapling mechanism commonly consists of a fixed stapling cartridge that contains a plurality of staples configured in a concentric circular array. A round cutting knife is concentrically mounted in the cartridge interior to the staples for axial travel therein. Extending axially from the center of the cartridge is a movable trocar shaft that is adapted to have a staple anvil removably coupled thereto. The anvil is configured to form the ends of the staples as they are driven into it. The distance between a distal face of the staple cartridge and the staple anvil is commonly controlled by an adjustment mechanism that is mounted to the proximal end of the stapler shaft for controlling the axial movement of the trocar. Tissue that is clamped between the staple cartridge and the staple anvil is simultaneously stapled and cut when the actuating mechanism is activated by the surgeon.

When using conventional circular staplers to perform Roux-en-Y gastric bypass surgery, the anvil of the device is placed transabdominally through an enlarged port site and passed through a gastrotomy on the anterior aspect of the stomach. The gastric pouch is constructed around the anvil and the gastrotomy is closed. The staple head of the circular stapler is inserted through the upper portion of the jejunum portion and the anvil is connected thereto. The stapler is then "fired" to create the anastomosis. Such method has been adopted by many surgeons. However, some drawbacks exist, including the need to enlarge the trocar site to accommodate the anvil and the construction of the gastrotomy and its closure. Such additional steps undesirably lengthen the time needed to complete the surgical procedure.

Thus, the need exists for a circular stapling device with an anvil arrangement that can puncture through gastric walls in an unexpanded state and then moved to an expanded state to facilitate formation of the anastomosis when the surgical stapler is actuated.

Such circular stapling devices are also commonly employed to removed diseased portions of the colon. Introduction and management of the circular stapler anvil into a conventional laparoscopic approach for colorectal surgery has been an ongoing limiter to employing laparoscopic procedures and techniques to complete such procedure. For example, laparoscopic colorectal procedures may be generally cumbersome to perform due to the number of steps involved. Such procedures are also complicated by the need to avoid crossing staple lines. Other problems that may be encountered with such procedures involve seeding from subject tissue removal, the need to create one or more ports for the introduction of anvils into the body cavity and the creation of colon defects that result from anvil placement challenges.

Thus, another need exists for a circular stapling device with an anvil arrangement that can be inserted into the patient in a collapsed state and then reconfigured into an expanded state to facilitate formation of the anastomosis when the surgical stapler is actuated.

The foregoing discussion is intended only to illustrate some of the shortcomings present in the field of the invention at the time, and should not be taken as a disavowal of claim scope.

BRIEF SUMMARY

In connection with general aspects of various embodiments of the present invention, there is provided an anvil assembly for a surgical stapling instrument. In various forms, the anvil assembly comprises a plurality of anvil plates that are movably coupled together for selective movement between a collapsed orientation and an expanded orientation. The plurality of anvil plates form at least a portion of a substantially planar anvil plate assembly when they are in the expanded orientation. An anvil expansion member is movably supported relative to the plurality of anvil plates and is selectively movable between a first unactuated position to a second position wherein the anvil expansion member moves the plurality of anvil plates to the expanded orientation. The anvil assembly further has a tissue-piercing tip portion.

In connection with yet another general aspect of one form of the present invention, there is provided a circular surgical stapling device. In one form, the device comprises a staple cartridge that operably supports a plurality of surgical staples therein. The device further comprises a trocar shaft that has a tissue-piercing tip formed thereon. The trocar shaft being selectively axially movable relative to the staple cartridge. The device further includes an umbrella-like anvil assembly that is movably supported relative to the staple cartridge. The umbrella-like anvil assembly comprises a plurality of anvil plate segments that are movably supported relative to each other for selective movement from a collapsed orientation to an expanded orientation in response to an application of actuation motion applied thereto by the trocar shaft. The plurality of anvil plate segments form an annular anvil plate assembly that is supported in substantial confronting relationship with the staple cartridge when the anvil assembly is in the expanded orientation.

In accordance with still another general aspect of one form of the present invention, there is provided a surgical procedure for forming an anastomosis. In one form the procedure comprises providing a circular stapler that has a staple cartridge end with an anvil attached thereto that is selectively movable between a collapsed configuration and an expanded configuration. The procedure further comprises orienting the anvil in a collapsed orientation and inserting the staple cartridge end with collapsed anvil attached thereto through an opening in a patient. The procedure additionally comprises piercing through target tissues through which the anastomosis is to be formed with the staple cartridge end with anvil attached thereto and expanding the anvil such that the target tissues are located between the expanded anvil and the staple cartridge end. Additionally the procedure comprises firing the stapler to drive surgical staples supported in the staple cartridge into forming contact with the expanded anvil and removing the staple cartridge end with an anvil attached thereto from the patient.

In accordance with a general aspect of one form of the present invention, there is provided an anvil plate for a surgical stapling instrument. In various forms, the anvil plate comprises a plurality of anvil plate segments that are movably interconnected and reconfigurable from a first orientation wherein the anvil plate segments may be inserted through a cannula opening as a unit and then reconfigured into a second orientation in the form of a substantially planar anvil plate assembly that has a diameter that is larger than the cannula opening.

In accordance with another general aspect of one form of the present invention, there is provided an anvil for a surgical stapling instrument. In one form, the anvil comprises a plurality of anvil plates that are movably coupled together for selective movement between non-planar orientations and a substantially planar orientation wherein the plurality of anvil plates form an annular anvil plate assembly. The anvil further comprises an anvil support member that is configured for attachment to the anvil plate assembly to retain it in the substantially planar orientation.

In accordance with a general aspect of one form of the present invention, there is provided an anvil for a surgical stapling instrument. In one form, the anvil comprises an anvil plate assembly that has a staple forming surface thereon and an anvil support member that is configured to move between a collapsed position and an expanded position wherein, when the anvil support member is in the expanded position, the anvil support member is attachable to the anvil plate assembly. In various embodiments, the anvil support member is couplable to an actuator portion of the surgical stapling instrument.

In accordance with another general aspect of one form of the present invention, there is provided an anvil support member for a surgical stapling device. In one form, the anvil support member comprises a shaft that is configured for attachment to an actuator portion of the surgical stapling device. The anvil support member further comprises a reconfigurable linkage assembly that is coupled to the shaft. The linkage assembly is reconfigurable from a first configuration wherein the linkage assembly may be inserted through a cannula opening to a second expanded configuration adapted to support an anvil plate assembly.

In accordance with still another general aspect of one form of the present invention, there is provided an anvil for a surgical stapling instrument. In one form, the anvil comprises an anvil shaft that is configured for attachment to an actuator portion of the surgical stapling device. The anvil shaft defines a shaft axis. A reconfigurable anvil head assembly is coupled to the anvil shaft and has an overall width measured along an axis that is substantially perpendicular to the shaft axis. The anvil head is reconfigurable between a first orientation wherein the overall width has a first magnitude and a second orientation wherein the overall width has a second magnitude that is greater than the first magnitude.

In accordance with one general aspect of one form of the present invention, there is provided an anvil assembly for a circular stapling instrument. In one form, the anvil assembly comprises an annular anvil plate assembly that has a staple-forming surface thereon. An anvil support member is couplable to an actuator portion of the surgical stapling instrument and is configured to selectively move between a collapsed position and an expanded position. The anvil assembly further comprises structures for coupling the anvil support member to the anvil plate assembly when the anvil support member is in the expanded position such that when the anvil support member is coupled to the actuator of the surgical stapling instrument, the staple-forming surface of the annular anvil plate assembly is in substantial registry with corresponding staples supported in the circular stapling instrument.

In accordance with another general aspect of one form of the present invention, there is provided a circular stapling instrument that includes a stapling head that supports a plurality of surgical staples therein. A firing system operably communicates with the stapling head for applying a firing motion to the stapling head to thereby drive the surgical staples therefrom. The instrument further includes an anvil adjustment system and an anvil assembly. In one form, the anvil assembly comprises an anvil shaft that is configured to be attached to the anvil adjustment system in a predetermined orientation. An anvil support member is operably coupled to the anvil shaft and is configured to be selectively moved between a collapsed position and an expanded position. The anvil assembly further comprises an anvil plate assembly that has a staple-forming surface thereon and structures configured to coupling the anvil support member to the anvil plate assembly when the anvil support member is in the expanded position such that when the anvil shaft is coupled to the anvil adjustment system in the predetermined orientation, the staple-forming surface of the anvil plate assembly is in substantial registry with corresponding surgical staples in the stapling head.

In accordance with still another general aspect of one form of the present invention, there is provided a method for stapling tissue that includes providing a circular stapling instrument that comprises a stapling head that supports a plurality of surgical staples therein. The stapling instrument further comprises a firing system that operably communicates with the stapling head for applying a firing motion to the stapling head to thereby drive the surgical staples therefrom and an anvil adjustment system. The method further includes providing an anvil support member that is selectively movable between a collapsed orientation and an expanded orientation and providing an anvil plate assembly that has a staple-forming surface thereon. In addition, the method comprises coupling the anvil support member to the anvil adjustment system when the anvil adjustment system is in the collapsed orientation and inserting the stapling head and attached anvil support member through an opening in a patient. The method further includes inserting the anvil plate assembly through the opening or another opening in the patient and orienting the anvil support member in the expanded orientation. In addition, the method includes attaching the anvil plate assembly to the expanded anvil support member in such a way that the staple-forming surface thereon is in substantial registry with the surgical staples in the stapling head and that the tissue to be stapled is positioned between the staple forming surface and the stapling head and activating the firing system to drive the surgical staples into forming contact with the staple forming surface.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2 is a partial cross-sectional view of a stapling head and anvil assembly embodiment of the present invention wherein the anvil assembly is in a collapsed configuration for puncturing through tissue;

FIG. 3 is a partial cross-sectional view of the stapling head and anvil assembly of FIG. 2 wherein the anvil assembly is in an open or expanded configuration to form a substantially planar anvil plate into which the staples in the stapling head may be fired;

FIG. 4 is a top view of the expanded anvil assembly of FIG. 3;

FIG. 10 is a partial cross-sectional view of another stapling head and anvil assembly embodiment of one form of the present invention wherein the anvil assembly is in a collapsed orientation;

FIG. 11 is a partial cross-sectional view of the stapling head and anvil assembly of FIG. 10 wherein the anvil assembly is in an expanded or deployed orientation;

FIG. 12 is a partial cross-sectional view of another stapling head and anvil assembly embodiment of the present invention being used to puncture through tissue;

FIG. 13 is a bottom perspective view of the stapling head and anvil assembly of FIG. 12 with the anvil assembly in the collapsed orientation;

FIG. 14 is a partial cross-sectional side view of the anvil assembly embodiment of FIGS. 12 and 13;

FIG. 29 is a side elevational view of an anvil support member embodiment depicted in FIG. 25 in a collapsed orientation;

FIG. 30 is a side elevational view of the anvil support member embodiment of FIG. 29 in an expanded or deployed orientation;

FIG. 31 is a partial cross-sectional view of an anvil plate embodiment of one form of the present invention latched to an anvil support member embodiment of one form of the present invention;

FIG. 32 is a perspective view illustrating insertion of another anvil plate assembly embodiment of the present invention in a collapsed orientation and inserted through a trocar cannula;

FIG. 33 is a view of a first anvil plate joint embodiment employed in the anvil plate assembly depicted in FIG. 32 and in a collapsed or open orientation;

FIG. 34 is another view of the first anvil plate joint embodiment of FIG. 33 in the expanded or closed orientation;

FIG. 35 is a view of a second anvil plate joint embodiment employed in the anvil plate assembly depicted in FIG. 32 in the collapsed or open orientation;

FIG. 36 is another view of the second anvil joint embodiment of FIG. 35 in the expanded or closed orientation;

FIG. 37 is an enlarged, view of an end of an anvil plate segment forming the second anvil joint depicted in FIG. 36;

FIG. 38 is a bottom view of the anvil plate assembly embodiment of FIGS. 32-37 in the expanded/assembled orientation;

FIGS. 39A-F and 39AA and 39CC depict various folded or collapsed orientations of another anvil plate assembly embodiment of another form of the present invention;

FIG. 40 is a front perspective view of an expanded anvil plate assembly embodiment depicted in FIGS. 39A-39F, 39AA and 39CC;

FIG. 40A is a back perspective view of the expanded anvil plate assembly embodiment of FIG. 40;

FIGS. 43A-43C are various views of the anvil assembly of FIG. 43;

FIG. 46 is a partial cross-sectional view of a stapling head and anvil assembly embodiment of one form of the present invention;

FIG. 47 is another partial cross-sectional view of the stapling head and anvil assembly embodiments of FIG. 46 with the linkage assembly thereof in a locked position;

FIG. 48 is a partial exploded assembly view of some of the components of the anvil assembly embodiment depicted in FIGS. 46 and 47 and a trocar shaft of a circular stapling instrument;

FIG. 49 is a perspective view of a locking sleeve and retention ring of the anvil assembly embodiment of FIGS. 46 and 47;

FIG. 50 is a perspective view of a locking ring embodiment of the present invention before being expanded;

FIG. 51 is a perspective view of the locking ring embodiment of FIG. 50 after being expanded;

FIG. 53 is a perspective view of another anvil support member embodiment of one form of the present invention in a collapsed orientation and with the anvil cap shown in cross-section;

FIG. 54 is another perspective view of the anvil support member embodiment of FIG. 53 in an open or expanded orientation;

FIG. 58 is an exploded perspective view of an anvil support member arrangement and anvil plate assembly arrangement of various embodiments of the present invention;

FIG. 59 is another exploded perspective view of the anvil support member embodiment and anvil plate assembly embodiment depicted in FIG. 58;

FIG. 68 is a perspective view of the anvil assembly of FIGS. 64-67 in a collapsed orientation;

FIG. 69 is a perspective view of a portion of the anvil assembly of FIGS. 64-68;

FIG. 70 is another perspective view of the anvil assembly of FIGS. 64-69 in a collapsed orientation;

DETAILED DESCRIPTION

Figure 1:
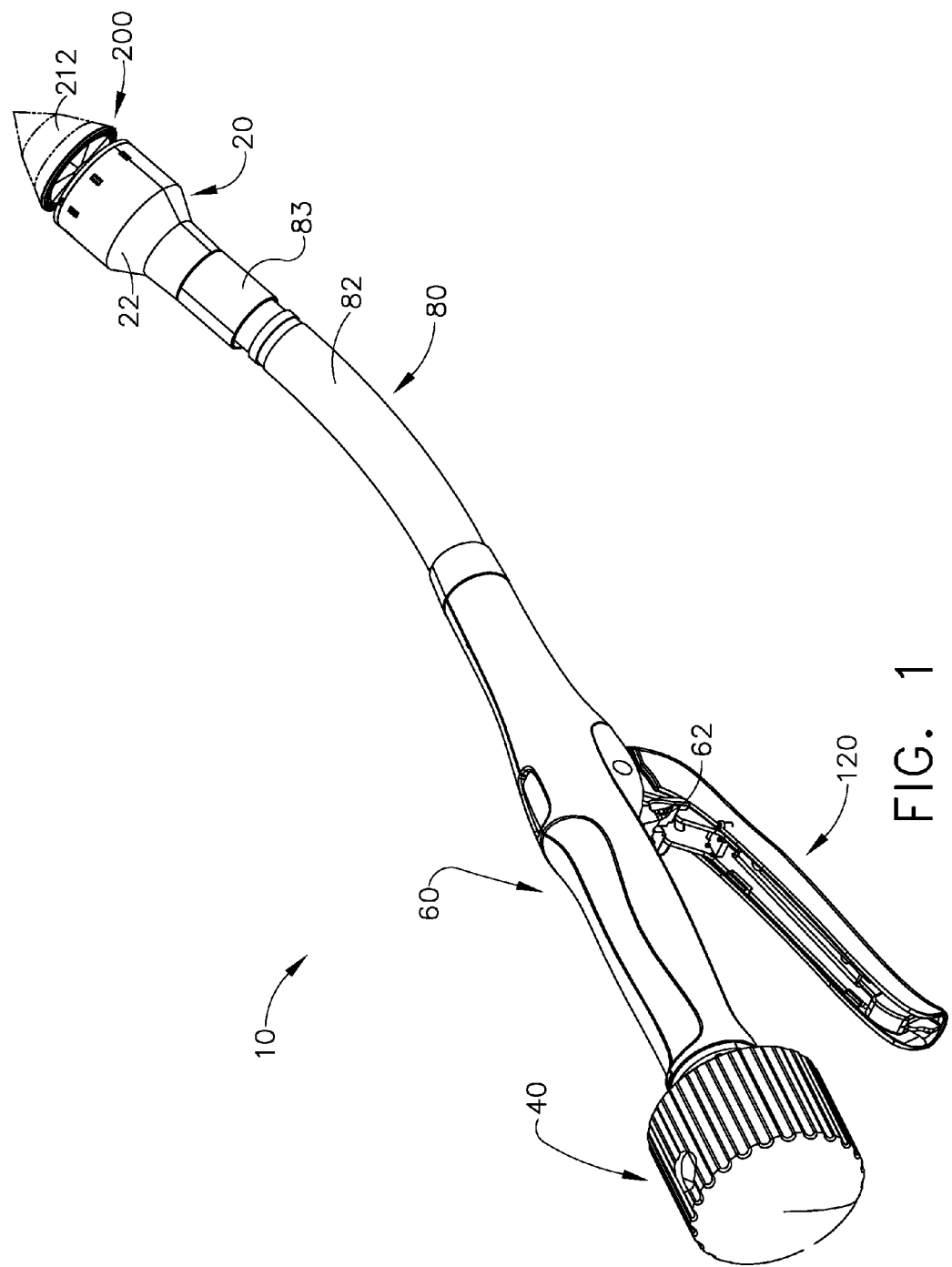
FIG. 1 is a perspective view of a surgical circular stapling instrument with an anvil assembly embodiment of the present invention shown in phantom lines.

The assignee of the present application also owns the following applications which were contemporaneously filed herewith and which are each herein incorporated by reference in their respective entireties:

U.S. patent application Ser. No. 13/181,779, filed Jul. 13, 2011, entitled "Multiple Part Anvil Assemblies For Circular Surgical Stapling Devices";

U.S. patent application Ser. No. 13/181,798, filed Jul. 13, 2011, entitled "Modular Surgical Tool Systems";

U.S. patent application Ser. No. 13,181,801, filed Jul. 13, 2011, entitled "Specimen Retraction Devices and Methods";

U.S. patent application Ser. No. 13,181,807, filed Jul. 13, 2011, entitled "Modular Occlusion and Tissue Acquisition Mechanisms For Circular Stapling Devices";

U.S. patent application Ser. No. 13,181,831, filed Jul. 13, 2011, entitled "Tissue Manipulation Devices";

U.S. patent application Ser. No. 13,181,786, filed Jul. 13, 2011, entitled "Circular Stapling Devices With Tissue-Puncturing Anvil Features";

U.S. patent application Ser. No. 13,181,774, filed Jul. 13, 2011, entitled "Anvil Assemblies With Collapsible Frames For Circular Staplers";

U.S. patent application Ser. No. 13,181,842, filed Jul. 13, 2011, entitled "Rectal Manipulation Devices";

U.S. patent application Ser. No. 13,181,836, filed Jul. 13, 2011, entitled "Surgical Access Devices With Anvil Introduction and Specimen Retrieval Structures"; and U.S. patent application Ser. No. 13,181,827, filed Jul. 13, 2011, entitled "Surgical Bowel Retractor Devices".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 illustrates a circular stapling instrument 10 that may be employed in connection with various anvil assembly embodiments of the present invention. The construction and operation of circular surgical stapling instruments are generally known in the art. Thus, those conventional components and features of circular staplers will not be discussed in detail herein beyond what may be necessary to understand the construction and operation of the various embodiments of the present invention. As the present Detailed Description proceeds, those of ordinary skill in the art will understand that the various embodiments of the present invention may be effectively employed with a variety of different circular stapler configurations without departing from the spirit and scope of the present invention. For example, various embodiments of the present invention may be employed with those circular staplers disclosed in U.S. Pat. No. 7,506,791, entitled "Surgical Stapling Instrument With Mechanical Mechanism For Limiting Maximum Tissue Compression", the disclosure of which is herein incorporated by reference in its entirety. Accordingly, the scope of protection afforded to the various embodiments of the present invention should not otherwise be limited to use with the exemplary circular stapler depicted herein.

The circular stapling instrument 10 depicted in FIG. 1 includes a stapling head 20, an anvil assembly 200, an adjustment knob assembly 40, and handle assembly 60. The stapling head 20 is coupled to the handle assembly 60 by an arcuate shaft assembly 80. A trigger 120 is pivotally supported by the handle assembly 60 and acts to operate the stapler 10 when a safety mechanism 62 is released. As will be discussed in further detail below, when the trigger 120 is activated, a firing system (not shown in FIG. 1) operates within the shaft assembly 80 to cause the staples to be expelled from the stapling head 20 into forming contact with the anvil assembly 200. Simultaneously, a knife operably supported within the stapling head 20 acts to cut tissue held within the circumference of the stapled tissue. The stapler 10 is then pulled through the tissue leaving stapled tissue in its place.

FIGS. 2 and 3 illustrate one form of stapling head 20 that may be employed in connection with various anvil assembly embodiments of the subject invention. In various embodiments, the stapling head 20 may comprise a casing member 22 that supports a staple cartridge 26 therein. The casing member 22 further supports a circular staple driver 24 that is adapted to interface with the staple cartridge 26 and drive staples 28 supported therein into forming contact with the anvil assembly 200 as will be discussed in further detail below. A circular knife member 30 is also centrally disposed within the staple driver 24. The proximal end of the casing member 22 may be coupled to an outer tubular shroud 82 of the arcuate shaft assembly 80 by a distal ferrule member 83.

Figure 5:
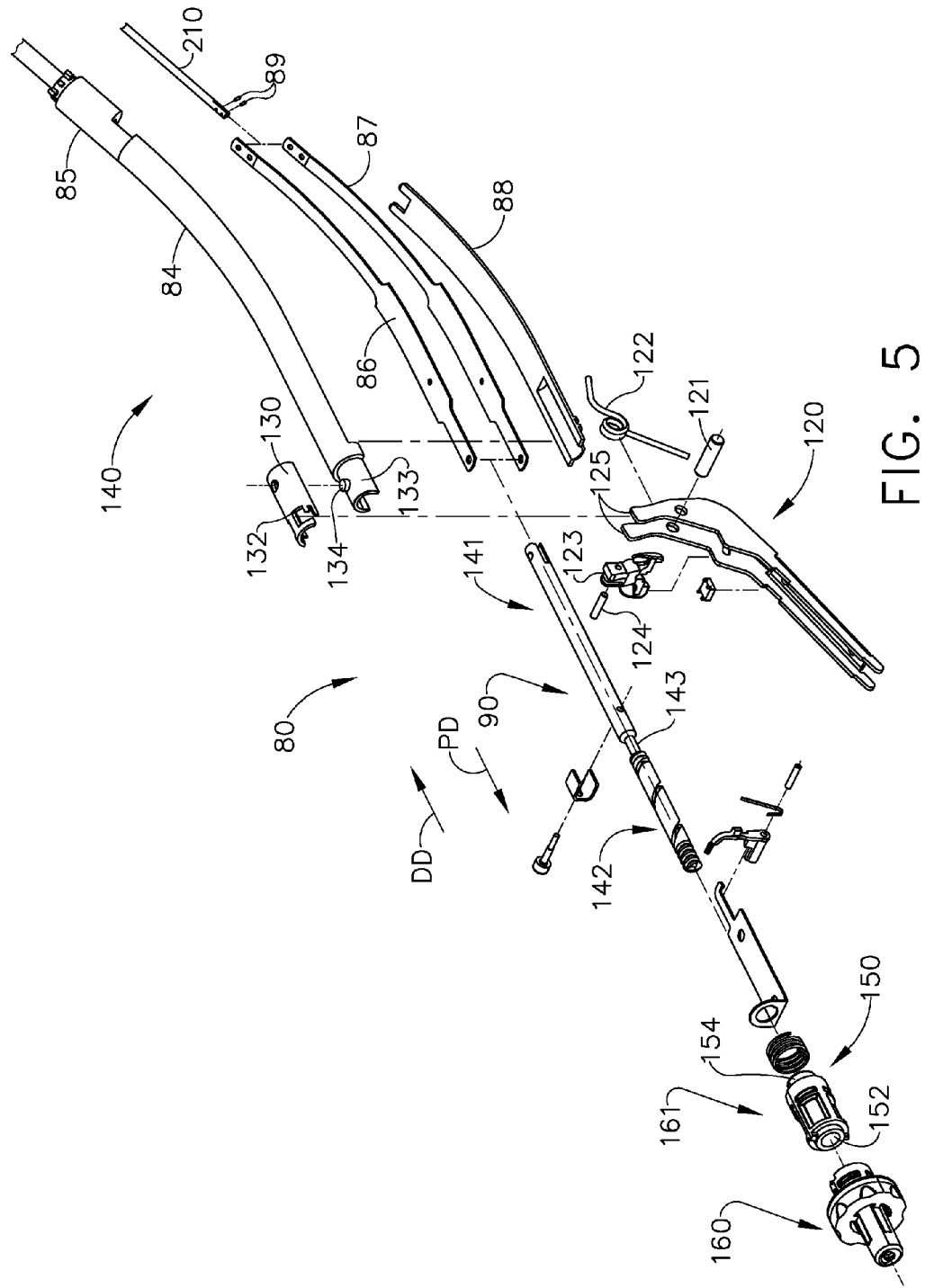
FIG. 5 is an exploded perspective view of a portion of the circular stapling instrument of FIG. 1.
Figure 6:
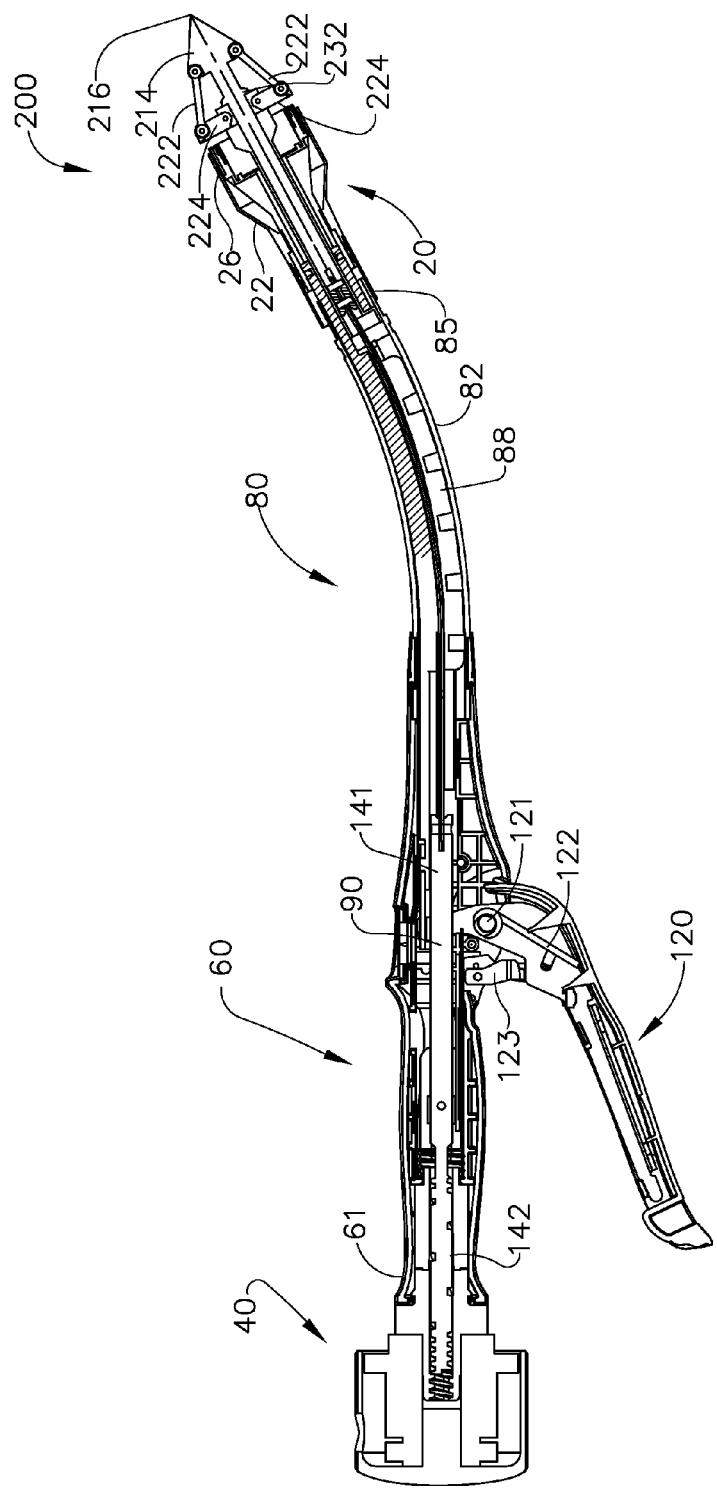
FIG. 6 is a cross-sectional view of the circular stapling instrument of FIG. 1.
Figure 7:
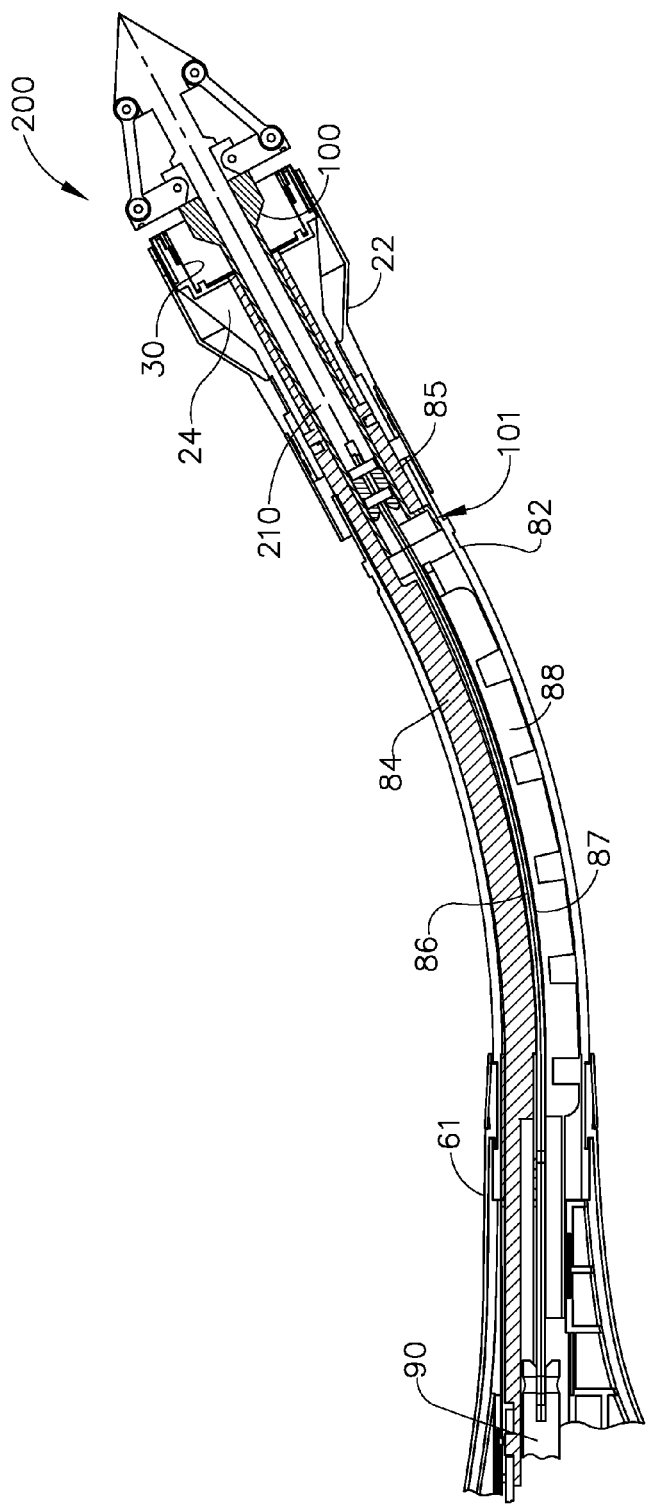
FIG. 7 is a partial cross-sectional view of a portion of the circular stapling instrument shaft and stapling head with an anvil assembly embodiment of the present invention attached thereto and in an expanded or deployed configuration.

FIGS. 5-7 illustrate one form of arcuate shaft assembly 80 that may be employed with various circular stapling instrument embodiments of the present invention. As can be seen in FIGS. 5 and 7, the arcuate shaft assembly 80 may include a compression shaft 84, a distal compression shaft portion 85, a top tension band 86, a bottom tension band 87 and a spacer band 88 that are assembled within the outer tubular shroud 82. The anvil shaft 210 of the anvil assembly 200 is attached to the top tension band 86 and bottom tension band 87 by fasteners 89. The proximal ends of the top tension band 86 and bottom tension band 87 are attached to a distal end of an adjustment shaft 90. As can be seen in FIG. 7, stapling head 20 includes a distally protruding central hub portion 100 that is centrally disposed within the stapling head 20 and attached to the shaft casing 82 at point 101. The central hub portion 100 may be attached to the shaft casing 82 by, for example, adhesive, welding, rivets, etc. The compression shaft 84 is free to move axially relative to the central hub portion 100 to drive the staple driver 24 distally. Thus, axial movement of the compression shaft 84 within the outer tubular shroud 82 causes the staple driver 24 to move axially within the casing member 22. As will be discussed below, actuation of the firing trigger 120 will cause the compression shaft 84 to move in the distal direction (arrow "DD") thereby driving the staple driver 24 distally to tire the staples 28 into forming contact with the anvil assembly 200. As the staple driver 24 is driven distally, it also drives the distal end 31 of the knife 30 through the tissue held within the circumference of the stapled tissue.

In various embodiments, the adjusting shaft 90 is movably supported within the handle assembly 60 that may comprise two handle casing segments 61 that are interconnected together by suitable fastener arrangements for ease of assembly. The trigger 120 is pivotally attached to the handle assembly 60 by a pivot pin 121. A spring 122 is supported on pivot pin 121 and serves to bias the trigger 120 away from the handle assembly 60 to an unactuated position. A safety yoke 123 is pivotally coupled to the handle 60 by pin 124 such that it can be pivoted between a safe position wherein the trigger 120 cannot be depressed towards the handle 60 and an off position wherein the safety yoke 123 does not inhibit pivotal travel of the trigger assembly 120 toward the handle assembly 60. As can be seen in FIG. 5, the trigger 120 may have a pair of fins 125 that are sized to be received in slots 132 in a firing clip 130 that is attached to the proximal end 133 of compression shaft 84 by a protrusion 134 or other suitable fastener arrangements. Such arrangement permits the distal axial movement (arrow "DD") and the proximal axial movement (arrow "PD") of the compression shaft 84 by pivoting the trigger 120 as will be further discussed below.

As can be seen in FIGS. 5 and 6, the adjustment shaft 90 has a distal portion 141 that is attached to the top and bottom tension bands 86, 87 and a proximal portion 142 that is adjoined to the distal portion 141 by a reduced diameter segment 143. The proximal portion 142 is axially received within an axial passage 152 in a distal closure nut 150 that is keyed onto or otherwise attached to a proximal closure nut 160 to form a closure nut assembly generally designated as 161 such that the distal closure nut 150 and the proximal closure nut 160 may rotate together. The distal closure nut 150 may further have a distally extending hub portion 154 that abuts an inwardly extending retainer flange formed inside the handle assembly 60. Such arrangement permits the distal closure nut 150 to freely rotate within the handle assembly 60, but is unable to move axially therewithin. Likewise, the proximal end portion 142 of the adjustment shaft 90 is axially received within an axial passage within the proximal closure nut 160. Also in various embodiments, the closure knob assembly 40 is attached to the proximal end of the proximal closure nut 160 in the various manners described in U.S. Pat. No. 7,506,791, the disclosure of which has been herein incorporated by reference. The closure knob assembly and adjustment shaft and related components for adjusting the position of the anvil relative to the stapling head is referred to herein as the "anvil adjustment system". Rotation of the closure knob assembly 40 results in the axial travel of the anvil shaft 210 in the proximal and distal directions depending on the direction in which the knob assembly 40 is rotated.

Turning to FIGS. 2-4, one implementation of an anvil assembly 200 is shown. As can be seen in those Figures, the anvil assembly 200 includes the anvil shaft 210 that has a tissue-penetrating tip member 212 formed at the distal end thereof. In various embodiments, the tissue-penetrating tip member 212 includes a substantially conically-shaped tip portion 214 that terminates in a sharpened point 216. In various embodiments, the tissue-penetrating tip member 212 may be integrally formed with the anvil shaft 210. In various implementations, the anvil shaft 210 and tissue-penetrating tip member 212 are fabricated from metal material.

Various forms of the anvil assembly 200 further include a plurality of linkage assemblies 220. In the embodiment depicted in FIG. 4, four linkage assemblies 220 are employed. Each linkage assembly 220 includes a distal link 222 that is pivotally coupled to the tissue-penetrating tip member 212. Each distal link 222 is pivotally coupled to a primary anvil plate segment 224 that is, intern, pivotally coupled to a collar 230 that is movably supported on the anvil shaft 210. Each primary anvil plate segment 224 has a primary staple-forming surface 226 formed thereon. In addition, the anvil assembly 200 further includes a plurality of secondary anvil plate segments 227 that are pivotally coupled to the collar 230. As can be seen in FIG. 4, for example, a secondary anvil plate segment 227 is arranged between adjacent primary anvil plate segments 224. In various embodiments, the primary anvil plate segments 224 and the secondary anvil plate segments 227 have complementary-shaped surfaces thereon, such that when the primary anvil plate segments 224 are pivoted to the open position (FIG. 3), they contact the adjacent secondary anvil plate segments 227 and pivot them to the open position as well to form a substantially planar anvil plate assembly 229. Each secondary anvil plate segment 227 has a primary staple-forming surface 228 thereon that cooperates with the primary staple-forming surfaces 226 of the primary anvil segments 224.

FIG. 2 illustrates the anvil assembly 200 in a collapsed orientation that permits the anvil assembly 200 to be inserted through a trocar cannula or other opening in the body. As the surgeon draws the anvil shaft 210 in the proximal direction "PD" by rotating the knob 40, the collar 230 will eventually contact the distal end 102 of the central hub portion 100 of the compression shaft 85. Continued movement of the anvil shaft 210 in the proximal direction will cause the movable collar 230 to travel distally on the anvil shaft 210 until it contacts a distal flange 232 on the anvil shaft 210. See FIG. 3. When in that position, the anvil assembly 200 is in the "expanded" or deployed orientation and the primary and secondary staple-forming surfaces 226, 228 of the primary and secondary anvil plate segments 224, 227 form the substantially planar anvil plate assembly 229 whose staple-forming surface is in confronting relationship with the staple cartridge 26 in the stapling head 20. The surgeon may then activate or "fire" the circular stapler 10 to drive the staples 28 into the staple-forming surfaces 226, 228.

Figure 8:
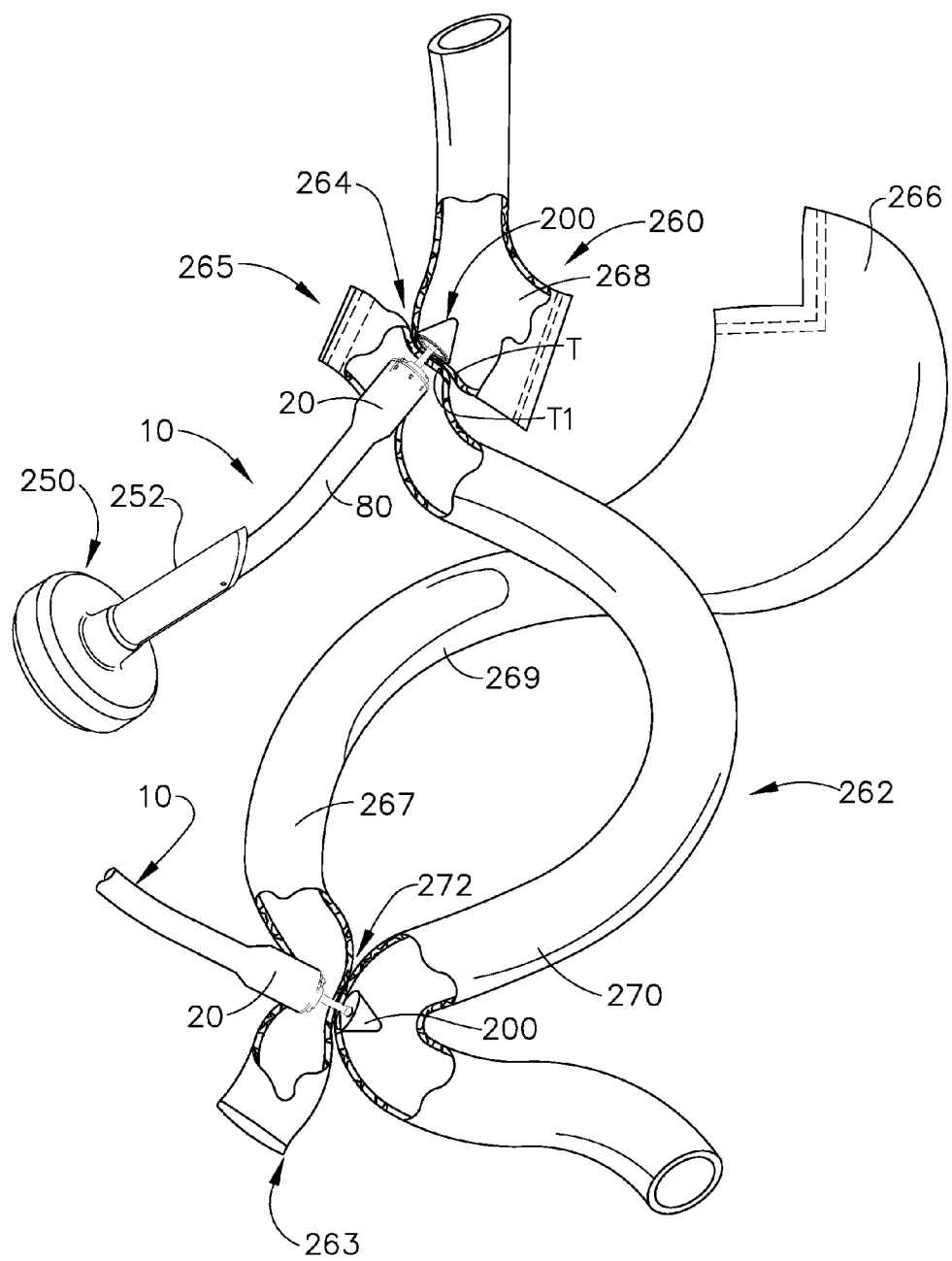
FIG. 8 is a diagrammatical view depicting use of various circular stapling instrument embodiments of the present invention to perform a Roux-en-Y procedure.

The circular stapling instrument 10 may be employed to perform a variety of different surgical procedures. FIG. 8 illustrates use of the circular stapling instrument 10 in connection with performing a Roux-en-Y procedure. When performing Roux-en-Y gastric bypass surgery laparoscopically, a number of conventional trocar devices 250 are placed in various locations through the patient's abdominal wall to provide passages through which surgical instruments, grasping devices and/or cameras may be inserted. As indicated above, such procedure involves the creation of a small stomach pouch 260 and the attachment of the jejunum 262 thereto by means of an anastomosis 264 (commonly referred to as the G-J anastomosis). The stomach pouch 260 may be formed by inserting a conventional endocutter (not shown) through the appropriate trocar device 250 and cutting and stapling a portion 268 of the stomach 266 at the esophago-gastric junction. A conventional endocutter may also be used to sever the jejunum 262 at a location 263 beyond where it exits the stomach 266. The severed end 265 of the jejunum 262 is then attached to the stomach pouch 260 using the anvil assembly 200 attached to a circular stapling instrument 10 that has been inserted through the trocar device 250.

In particular, the circular stapling head 20 with the anvil assembly 200 coupled thereto in a collapsed orientation (FIG. 2) is inserted through the cannula portion 252 of the trocar device 250. The anvil assembly 200 is advanced through the severed end portion 265 of the jejunum 262 by pushing the tissue-penetrating tip member 212 therethrough and also through the wall of the stomach pouch 260. Once the anvil assembly 200 has been inserted through the wall of the stomach pouch 260, the surgeon may then draw the anvil assembly 200 toward the stapling head 20 of the circular stapling instrument 10 to capture the wall ("T") of the pouch 260 and the wall ("T1") of the severed end portion 265 of the jejunum 262 between the anvil assembly 200 and the stapling head 20. As the anvil assembly 200 is drawn into expanding contact with the distal end 102 of the central hub portion 100 of the compression shaft 85, the anvil plate assembly 229 is formed. The stapling device 100 may then be fired to create the G-J anastomosis. The circular stapling instrument 10 may then be withdrawn from the trocar device 250.

A second circular stapling instrument 10 or the prior circular stapling instrument 10 with a new staple cartridge 26 installed therein may then be inserted through the cannula portion 252 of an appropriately located trocar device 250 and the tissue penetrating tip member 212 may be used to penetrate through a portion 267 of the jejunum below the duodenum 269 and through a portion of the lower jejunum portion 270 as shown in FIG. 8. Once the anvil assembly 200 has been located within the lower jejunum portion 270, the surgeon may then draw the anvil assembly 200 toward the stapling head 20 which causes the anvil assembly 200 to move to the expanded or deployed orientation. The surgeon continues to draw the expanded anvil plate assembly 200 toward the stapling head assembly 20 to capture the walls "(T2" and "T3") of the jejunum portions 267, 270 therebetween and then fires the circular stapling instrument 10 to form anastomosis 272 therebetween (commonly referred to as the J-J anastomosis). Such arrangement therefore bypasses the severed portion of stomach 266 and duodenum 269.

Figure 9:
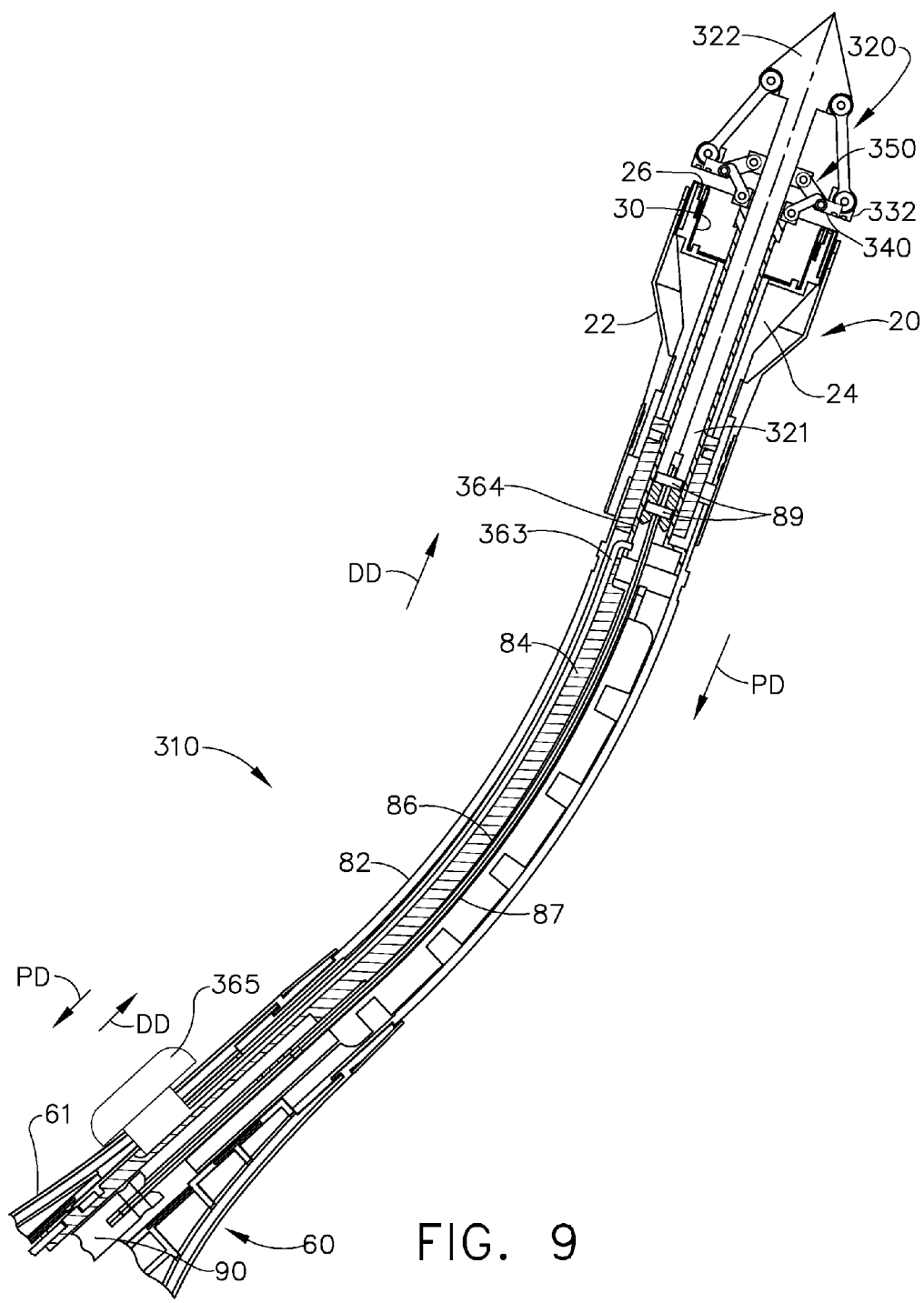
FIG. 9 is a partial cross-sectional view of a portion of a circular stapling instrument shaft and stapling head embodiment of one form of the present invention with another anvil assembly embodiment of the present invention attached thereto and in an expanded or deployed orientation.
Figure 15:
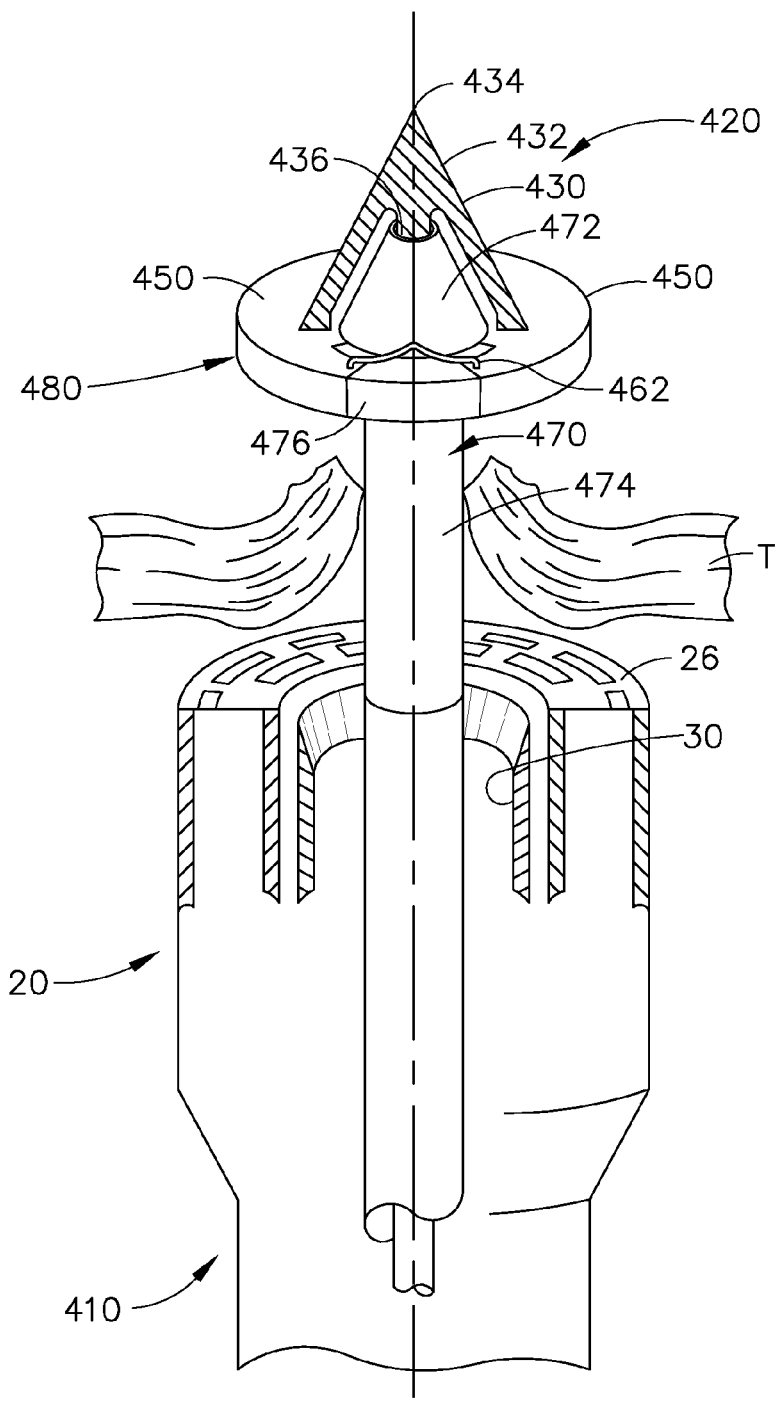
FIG. 15 is a partial perspective view of the stapling head and anvil assembly of FIGS. 12-14 after it has punctured through tissue and has been moved to the expanded or deployed orientation and wherein some components thereof are shown in cross-section.
Figure 18:
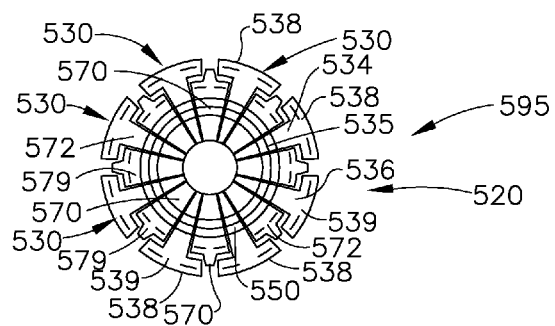
FIG. 18 is a top view of the anvil assembly embodiment of FIGS. 16 and 17 in an expanded or deployed orientation.

FIGS. 9-11 illustrate another circular stapling instrument 310 of the present invention. Various embodiments of the circular stapling instrument 310 have components that are substantially identical to the circular stapling instrument 10 described above and have been identified with the same element numbers in FIGS. 9-11. Those components that differ from or are in addition to the components of the circular stapling instrument 10 will now be described. As can be seen in FIG. 9, the circular stapling instrument 310 includes an anvil assembly 320 that includes an anvil shaft 321. The anvil shaft 321 is attached to the top tension band 86 and bottom tension band 87 on the circular stapling instrument 310 by fasteners 89. The proximal ends of the top tension band 86 and bottom tension band 87 may be attached to a distal end of the adjustment shaft 90 as was described above. In this embodiment, the distal compression shaft portion 85 is configured to engage the staple driver assembly 24 that is operably supported within the stapling head 20. Thus, axial movement of the compression shaft 84 within the outer tubular shroud 82 causes the staple driver assembly 24 to move axially within the casing member 22 of the stapling head 20. As was discussed above, actuation of the firing trigger 120 (FIG. 1) will cause the compression shaft 84 to move in the distal direction (arrow "DD") thereby driving the staple driver assembly 24 distally to fire the staples in the staple cartridge 26 into forming contact with the anvil assembly 320. As the staple driver assembly 24 is driven distally, it also drives the distal end of the knife 30 through the tissue held within the circumference of the stapled tissue.

Turning to FIGS. 10 and 11, one implementation of an anvil assembly 320 is shown. As can be seen in those Figures, a tissue-penetrating tip member 322 is formed at the distal end of the anvil shaft 321. In various embodiments, the tissue-penetrating tip member 322 includes a substantially conically-shaped tip portion 324 that terminates in a sharpened point 326. In various embodiments, the tissue-penetrating tip member 322 may be integrally formed with the anvil shaft 321. The anvil shaft 321 and tissue-penetrating tip member 324 is fabricated from metal material.

Various forms of the anvil assembly 320 further include an anvil linkage assembly 330. In the embodiment depicted in FIGS. 10 and 11, the anvil linkage assembly 330 includes a plurality of (four) outer anvil plate segments 332 that are pivotally coupled to the tissue-penetrating tip member 324 by corresponding first links 334. Each outer anvil plate segment 332 has a staple-forming surface 336 that has staple-forming pockets 338 formed therein. When the anvil assembly 320 is in the expanded or deployed position (FIG. 11), the staple-forming pockets 338 correspond to the outermost row of staples within the staple cartridge 26 supported in the stapling head 20 of the circular stapling instrument 310.

As can also be seen in FIGS. 10 and 11, the anvil linkage assembly 330 further comprises a collection of inner anvil plate segments 340. The inner anvil plate segments 340 are pivotally coupled to an inner linkage assembly 350 that is coupled to the anvil shaft 321. In at least one implementation, for example, the inner linkage assembly 350 includes a central collar 352 that is attached to the anvil shaft 321. Each inner anvil plate segment 340 is pivotally coupled to the central collar 352 by a primary link 354. The inner linkage assembly 350 further includes a plurality of actuator blocks 356. Each inner anvil plate segment 340 has a corresponding actuator block 356 attached thereto by a secondary link 358. Each inner anvil plate segment 340 has a staple-forming surface 342 that has staple-forming pockets 344 therein. When the anvil assembly 320 is in the expanded or deployed position (FIG. 11), the staple-forming pockets 344 correspond to the innermost row of staples within the staple cartridge 36 in the circular stapling instrument 310.

In various embodiments, a central hub portion 360 extends centrally through the stapling head 20. A proximal end 361 of the central hub portion 360 is configured to slidably engage the inside wall of the tubular shroud 82 as can be seen in FIG. 11. The compression shaft 84 is free to move axially relative to the central hub portion 360 to drive the staple driver assembly 24 distally. Thus, axial movement of the compression shaft 84 within the tubular shroud 82 causes the staple driver assembly 24 to move axially within the casing member 22 of the stapling head 20. As will be discussed below, actuation of the firing trigger 120 will cause the compression shaft 84 to move in the distal direction (arrow "DD") thereby driving the staple driver assembly 24 distally to fire the staples in the staple cartridge 26 into forming contact with the substantially planar anvil plate assembly 346 formed by the outer anvil plate segments 332 and the inner anvil plate segments 340. As the staple driver assembly 24 is driven distally, it also drives the distal end of the knife 30 through the tissue held within the circumference of the stapled tissue.

In various implementations, the central hub portion 360 is also configured to move axially within the stapling head 20. As can be seen in FIGS. 9 and 11, an actuator rod 363 is coupled to the proximal end 364 of the central hub portion 360 and is coupled to a slider switch 365 mounted in the handle 60. The slider switch 365 may be configured to slide distally and proximally to axially advance and retract the central hub portion 360. The slider switch may be configured with a series of detents (not shown) or other structures (nor shown) which define switch positions that correspond to axial positions for the central hub portion 360. Thus, the slider switch 365 and ultimately the central hub portion 360 will be locked in position and unable to move axially when the slider switch 365 is moved to one of those switch positions.

FIG. 10 illustrates the anvil assembly 320 in a collapsed orientation that permits the anvil assembly 320 to be inserted through a cannula portion of a trocar device or other opening in the body. Once the anvil assembly 320 has been punctured through the tissue to be cut and stapled, the surgeon draws the anvil shaft 321 in the proximal direction "PD" by rotating the knob 40. Once the collapsed anvil assembly 320 is drawn adjacent to the staple cartridge 26, the surgeon may then advance the central hub portion 360 distally to cause the anvil assembly 320 to move to the expanded or deployed orientation. As the distal end 362 of the central hub portion 360 moves distally, it contacts the actuator blocks 356 of the inner linkage assembly 350. Movement of the actuator blocks 356 distally facilitates pivotal movement of the inner anvil plate segments 340 into contact with the outer anvil plate segments 332 to bias the outer anvil plate segments 332 radially outward to form a substantially planar anvil plate assembly 346 as shown in FIG. 11. When in that position, the anvil assembly 320 is in the "expanded" or deployed orientation and the staple-forming surfaces 336, 342 of the anvil plate segments 332, 340 are in confronting relationship with the staple cartridge 26 in the stapling head 20 of the circular stapling instrument 310. The surgeon may then activate or "fire" the circular stapling instrument 310 to drive the staples into the staple-forming pockets 338, 344 in the staple-forming surfaces 336, 342, respectively. The circular stapling instrument 310 may, for example, be used to perform a Roux-en-Y procedure in the manner described above, as well as to perform other surgical procedures.

FIGS. 12-15 illustrate another expandable anvil embodiment of various forms of the present invention that may be used in connection with a circular stapling instrument 410. Various embodiments of the circular stapling instrument 410 have components that are substantially identical to the circular stapling instrument 10 described above and therefore, their construction and operation will not be repeated again, beyond that which is necessary to understand the construction and operation of the circular stapling instrument 410. As can be seen in FIGS. 12-15, the circular stapling instrument 410 includes an expandable and collapsible anvil assembly 420. In this implementation, the circular stapling instrument 420 includes a trocar shaft 412 that may be attached to the top tension band 86 and bottom tension band 87 of the circular stapling instrument 410 by fasteners 89. The proximal ends of the top tension band 86 and bottom tension band 87 may be attached to a distal end of an adjustment shaft 90 as was described above.

FIGS. 13 and 14 illustrate one form of trocar shaft 412 that may be employed with various embodiments of the present invention. Those of ordinary skill in the art will also appreciate that various embodiments of the present invention may also be employed with conventional trocar shaft arrangements without departing from the spirit and scope of the present invention. As can be seen in FIGS. 13 and 14, the trocar shaft 412 is provided with a plurality of (preferably four) outwardly extending attachment fins 414. Such arrangement permits the trocar shaft 412 to be non-rotatably attached to a variety of different tip assemblies that may be employed in connection with different types of end effector arrangements that are specifically configured to perform various surgical procedures and actions.

The circular stapling instrument 410 may be effectively employed with an anvil assembly 420 which serves to form the staples as they are driven from the staple cartridge 26. As can be seen in FIG. 14, one form of anvil assembly 420 includes a tissue-penetrating tip member 430 that is attachable to the trocar shaft 412. In various embodiments, the tissue-penetrating tip member 430 includes a substantially conically-shaped tip portion 432 that terminates in a sharpened point 434 and has an anvil shaft 436 attached thereto. The proximal end 438 of the anvil shaft 436 is substantially hollow and sized to receive the trocar tip 416 therein. The proximal end 438 has a pair of spaced attachment tabs 440 protruding therefrom which extend between the trocar fins 414. Each attachment tab 440 has a hole or recess 442 therein that is oriented to receive a corresponding detent 418 formed on the trocar shaft 412. Thus, when the detents 418 snap into their corresponding hole or recess 442, the tissue-penetrating tip member 430 is affixed to the trocar shaft 412 for travel therewith. In various embodiments, the tissue-penetrating tip member 430 is fabricated from metal material.

Various forms of the anvil assembly 420 further include a plurality of anvil plates 450. In the embodiment depicted in FIGS. 12-15, two anvil plates 450 are employed. In at least one embodiment, each anvil plate 450 has an arcuate shape and has at least one staple-forming pocket therein. In a preferred embodiment, each anvil plate 450 has a first arcuate configuration 452 of staple-forming pockets 454 therein and a second arcuate configuration 456 of staple-forming pockets 458 therein that, when the anvil assembly 420 is in the expanded or deployed orientation, correspond to the circular array of staples within the staple cartridge 26. In various embodiments, the anvil plates 450 each have an anvil hub portion 460 that extends around a portion of the anvil shaft 436. The anvil plates 450 are movably coupled together by at least two spring clips 462 (shown in FIG. 15). The spring clips 462 serve to bias the anvil hub portions 460 into frictional engagement with the anvil shaft 436 to retain the anvil plates 450 in the collapsed orientation. See FIGS. 12 and 13. In addition, in at least one implementation, each anvil plate 450 has a tapered inner wall portion 464 formed thereon. When the anvil plates 450 are in collapsed orientation, a space 466 is provided between the tapered inner wall portions 464 of the confronting anvil plates 450. See FIG. 13.

Various embodiments of the anvil assembly 420 further comprise an anvil expansion member 470 that has a centrally-disposed conical tip portion 472 that is sized to axially extend into the opening 466 when the anvil assembly 420 is moved in the proximal direction "PD" toward the stapling head 20. A hollow expansion shaft 474 extends from the conical tip portion 472 and is sized to permit the anvil shaft 436 to axially move within it. In addition, the anvil expansion member 470 further has a pair of diametrically-opposed anvil plate sections 476 protruding therefrom. The anvil plate sections 476 are sized and shaped relative to the anvil plates 450 such that when they are received between the confronting anvil plates 450, they interlock therewith to form a substantially planar and annular anvil plate assembly 480. See FIG. 15.

As can be seen in FIGS. 12 and 13, each of the anvil plate sections 476 has a first arcuate configuration 452 of staple-forming pockets 454 therein and a second arcuate configuration 456 of staple-forming pockets 458 therein that, when the anvil assembly 420 is in expanded or deployed orientation, correspond to the circular array of staples within the staple cartridge 26. It will be understood, that the staple-forming pockets 454, 458 serve to form the staples as they are driven through the tissue "T" to be stapled and into the anvil plate assembly 480.

In various embodiments, the expansion shaft 474 extends through a centrally-disposed hub shaft (not shown) in the stapling head 20. The expansion shaft 474 is sized and shaped relative to the hub shaft to establish a slidable frictional fit therewith. FIGS. 12 and 13 illustrate a starting position of the anvil expansion member 470 when the anvil assembly 420 is in the collapsed position. When in that position, the anvil expansion member 470 is retained in that position by the frictional fit established between the expansion shaft 474 and the hub shaft. When in the collapsed orientation, the surgeon may then force the tissue-penetrating tip member 432 through the tissue "T" to be stapled to enable the anvil assembly 420 to extend therethrough. Once the collapsed anvil assembly 420 is located on the opposite side of the tissue "T", the substantially planar anvil plate assembly 480 is then drawn toward the stapling head 20 to capture the target tissues therebetween. The anvil assembly 420 is moved in the proximal direction "PD" by rotating the knob 40 on the handle portion 60 to drawn the trocar shaft 412 toward the handle 60 as is known. As the anvil assembly 420 is moved in the proximal direction, the tip portion 472 of the anvil expansion member 470 enters the opening 466 between the anvil plates 450 and engages the tapered inner walls 464 of the anvil plates 450 to bias the anvil plates 450 radially outward in the radial direction "RD" (FIG. 14) until the anvil plate sections 476 are received between the anvil plates 450. See FIG. 15. When in that expanded orientation, the anvil plates 450 interlock with the anvil plate sections 476 to form a substantially planar and annular anvil plate assembly 480. Further movement of the anvil assembly 420 in the proximal direction "PD", causes the anvil expansion shaft 474 to slide within the hub shaft to enable the anvil assembly 420 to be moved to the desired position for stapling and cutting tissue. Once the anvil assembly 420 has been properly positioned relative to the stapling head 20, the surgeon may then "fire" the device by activating the firing trigger 60 which drives the knife 30 and drives the staples into forming contact with the substantially planar annular anvil plate assembly 480. The expandable anvil assembly 420 may be in connection with a circular stapling instruments of the type described above or other circular stapling instruments may, for example, to be used to perform a Roux-en-Y procedure in the manner described above, as well as to perform other surgical procedures.

FIGS. 16-19 illustrate another expandable anvil assembly 520 that may be employed with the circular stapling instrument 510 to perform various stapling procedures such as the Roux-en-Y procedure described above. Various embodiments of the circular stapling instrument 510 have components that are substantially identical to the circular stapling instruments 310 described above and/or others described and therefore, their construction and operation will not be repeated again beyond that which is necessary to understand the construction and operation of the circular stapling instrument 510.

In at least one implementation, the expandable anvil assembly 520 comprises an umbrella-like assembly that includes a plurality of selectively splayable first anvil links 530 that have a distal end portion 532 that is pivotally attached to an anvil shaft 540. Each first anvil link has an elongated body portion 534 and a proximal end 536 that has a first anvil plate segment 538 formed on thereon. The first anvil links 530 may be fabricated from metal material. The first anvil plate segments 538 each have a first staple-forming surface that has a first arcuate configuration of first staple-forming pockets 539 therein. See FIG. 18. In various embodiments, each of the first anvil links 530 has a lock ring detent 535 formed thereon and are movably received within a lock ring 550.

In various embodiments, the expandable anvil assembly 520 further includes a second anvil link assembly 570 that includes a plurality of primary links 572 that are pivotally coupled to an intermediate harness ring 574. A secondary anvil plate segment 576 is pivotally coupled to each of the primary links 572. The secondary anvil plate segments 576 are pivotally coupled to an actuator ring 580. The intermediate harness ring 574 and the actuator ring 580 are movably journaled on the anvil shaft 540. Each of the secondary anvil plate segments 576 have a staple-forming underside 577 thereon that have a staple-forming pockets 579 therein. See FIG. 18.

Figure 16:
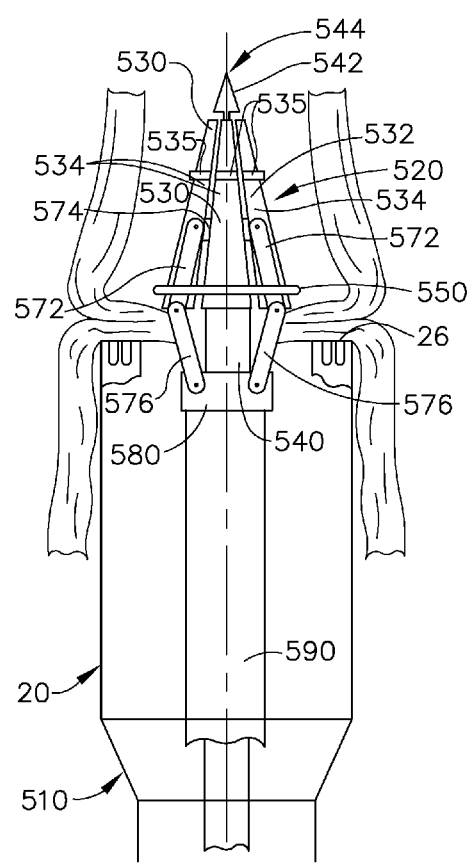
FIG. 16 is a partial cross-sectional view of another stapling head and anvil assembly embodiment of one form of the present invention after the anvil assembly has been used to puncture through adjacent target tissues.
Figure 19:
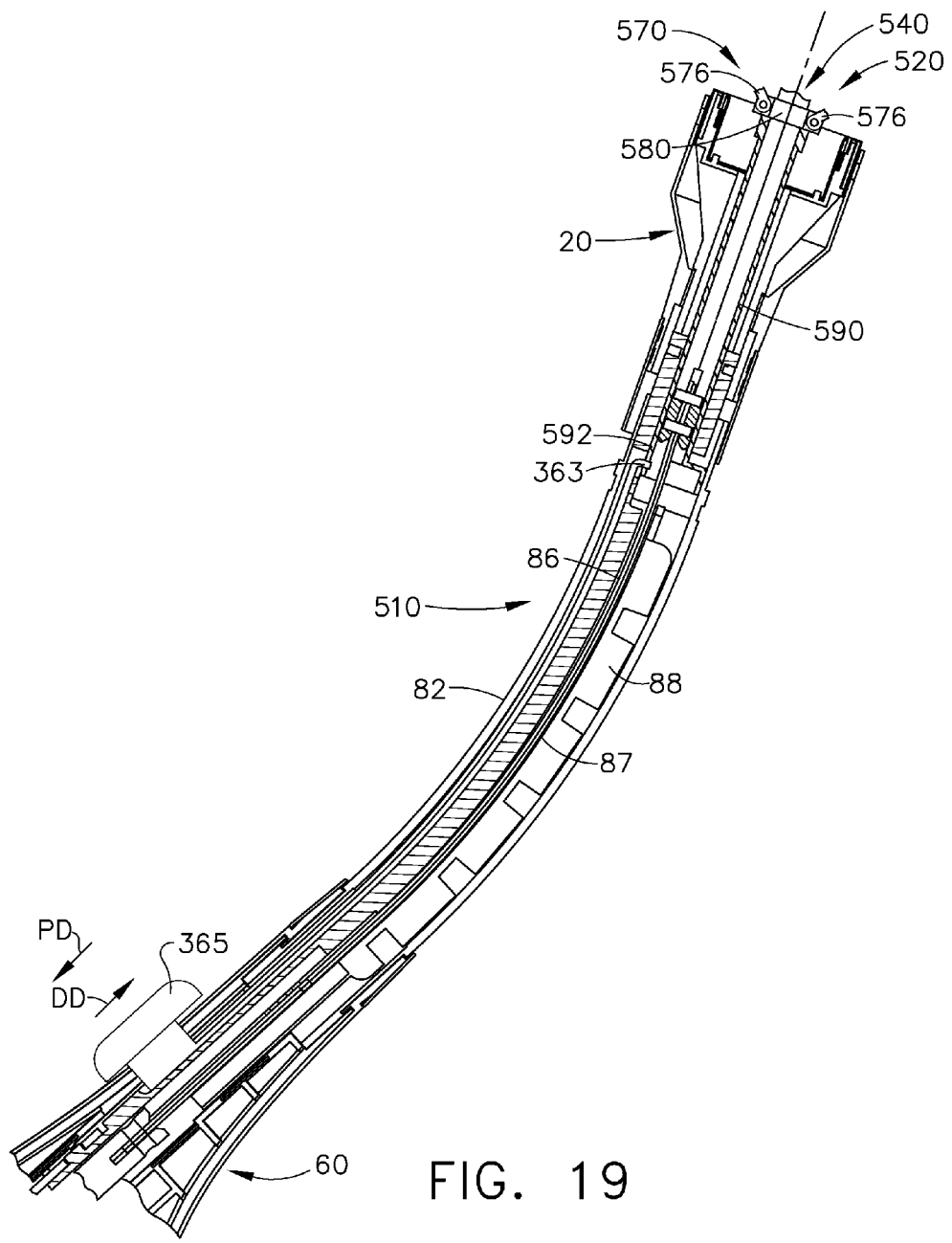
FIG. 19 is a partial cross-sectional view of another circular stapling instrument embodiment of the present invention coupled to the anvil assembly embodiment depicted in FIGS. 16-18.

This embodiment further includes a centrally disposed actuator hub 590 that is movably supported within the stapling head 20 as shown in FIG. 19. The proximal end 592 of the actuator hub 590 is attached to the actuator rod 361 which is coupled to the slider switch 365 on the handle 60. Movement of the slider switch 365 in the distal direction "DD" will drive the actuator hub 590 in the distal direction within the stapling head 20. Such movement of the actuator hub 590 drives the second anvil link assembly 570 distally to cause the first anvil links 530 to splay open. As the first anvil links 530 splay open, the locking ring 550 is caused to slide up the first anvil links 530. The surgeon will continue to advance the second anvil link assembly 570 distally until the staple-forming surfaces 577 of the secondary anvil plate segments 576 are in confronting relationship to the staple cartridge 26 in the stapling head 20. FIG. 16 illustrates the secondary anvil plate segments 576 in an intermediate position prior to attaining the confronting relationship relative to the staple cartridge 26. In various embodiments, the slider switch 365 may be configured with detents or other locking arrangements to define the final "firing" position of the second anvil link assembly wherein the first anvil plate segments and the secondary anvil plate segments cooperate to form a substantially planar annular anvil plate assembly generally designated as 595. See FIG. 18. Thus, when the slider switch 365 is locked in position, the actuator hub 590 is locked in position wherein the intermediate harness ring 574 is in abutting relationship with a locking flange 541 on the anvil shaft 540. When in that position, the locking ring 550 is in abutting relationship with the locking ring detents 535 on the first anvil links 530 to lock the first anvil links 530 in that splayed position.

Figure 17:
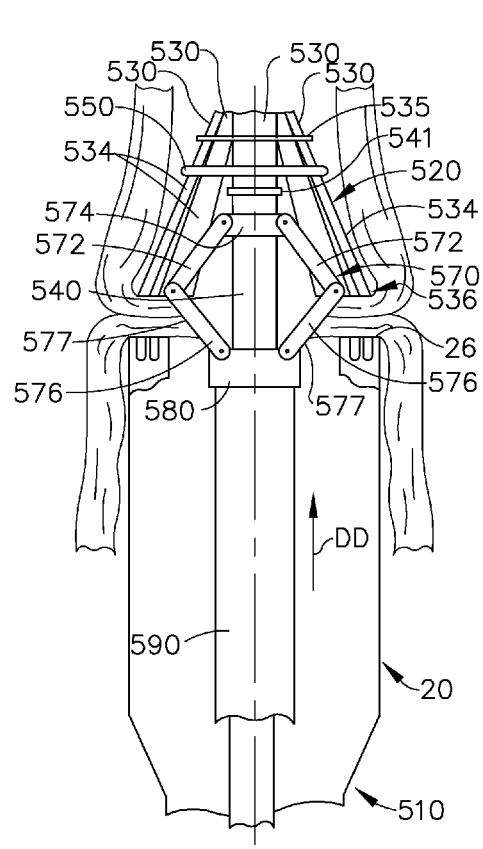
FIG. 17 is another partial cross-sectional view of the stapling head and anvil assembly embodiment of FIG. 16 prior to commencing the firing of staples.

In various implementations, the anvil shaft 540 of the circular stapling instrument 510 has a trocar tip portion 542 that terminates in a pointed tissue-penetrating tip 544. See FIG. 17. In FIG. 17, the expandable anvil assembly 520 is in the collapsed orientation. When in the collapsed orientation, the trocar tip portion 542 may be used to puncture through tissue. As can be see in that Figure, for example, the trocar tip portion 542 has punctured through the tissues "T" and "T1" that are to be cut and stapled. Thereafter, the surgeon may activate the slider switch 365 to form the substantially planar annular anvil plate assembly 595. Once the anvil plate assembly 595 has been formed in confronting relationship with the staple cartridge 26 supported in the stapling head 20, the surgeon may activate the firing trigger 120 on the handle 60 to fire the staples and knife 30 as described above.

In the past, laparoscopic colectomies were cumbersome to perform due to the number of steps required to be performed to introduce the stapling instruments to the surgical site. Problems with crossing staple lines, seeding from subject tissue removal, creation of ports for introduction of anvils into the body cavity, and colon defects from anvil placement were often encountered when employing such procedures. The various embodiments of the present invention described above may be effectively used to perform a laparoscopic colectomy while avoiding many, if not all of such problems.

Figure 20:
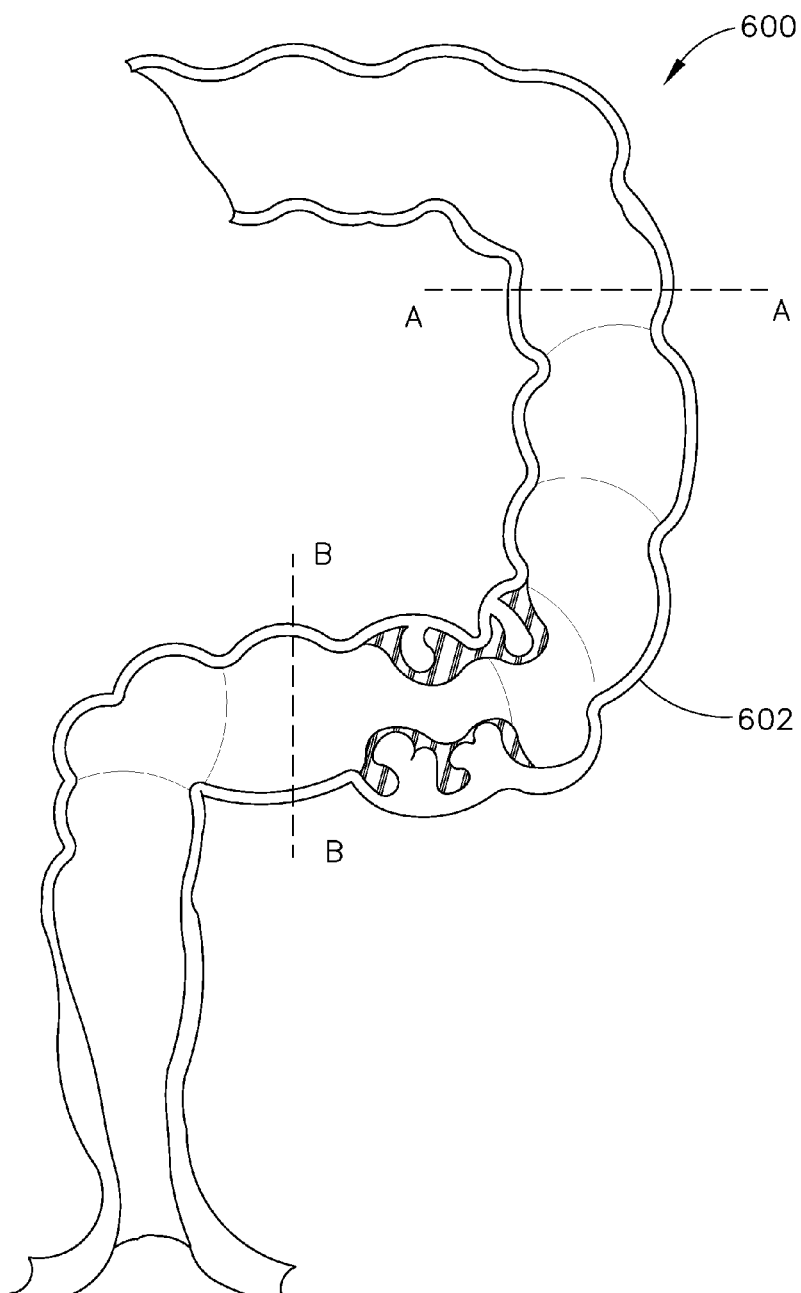
FIG. 20 is a diagrammatic view of a portion of a patient's colon that has a diseased portion to be removed.
Figure 21:
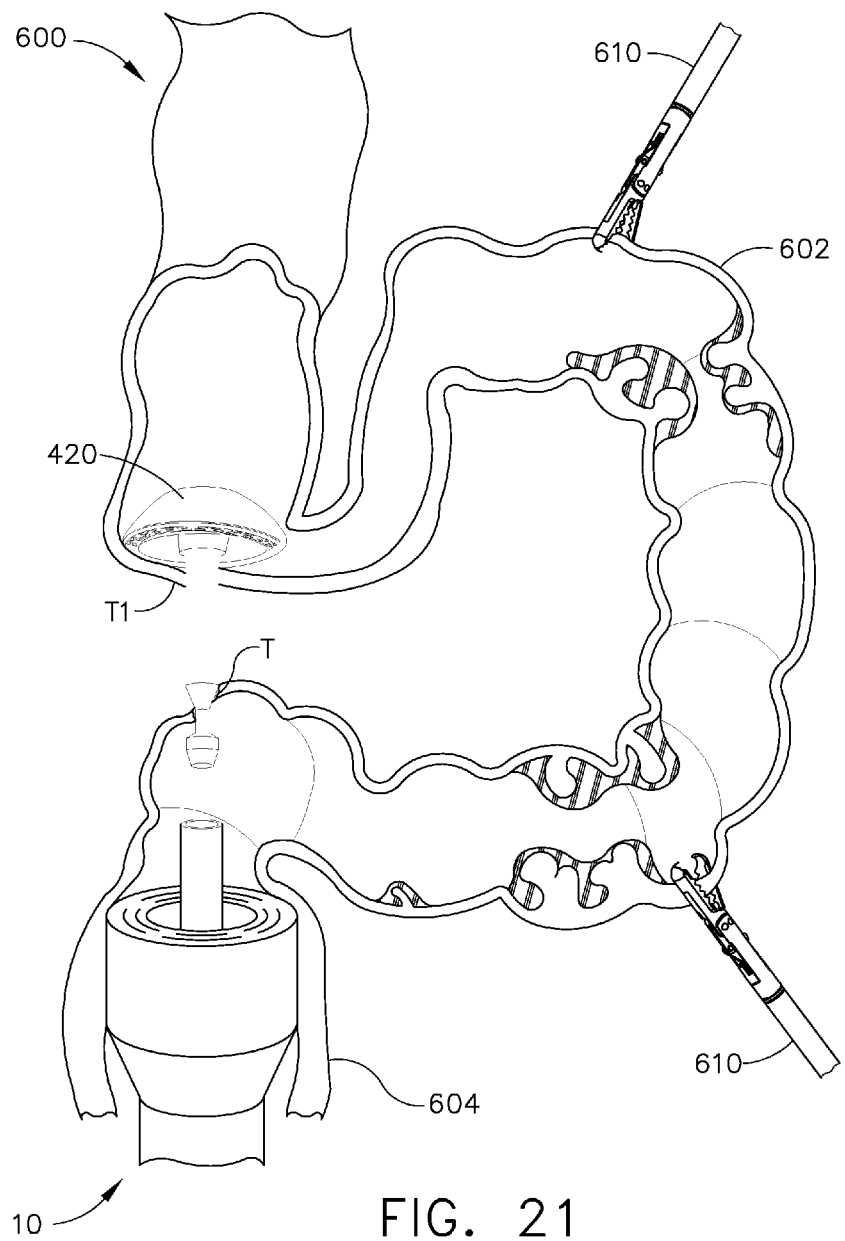
FIG. 21 is another diagrammatic view of the patient's colon depicted in FIG. 20 depicting use of a stapling instrument and anvil assembly embodiment of the present invention in connection with the removal of the diseased portion.
Figure 22:
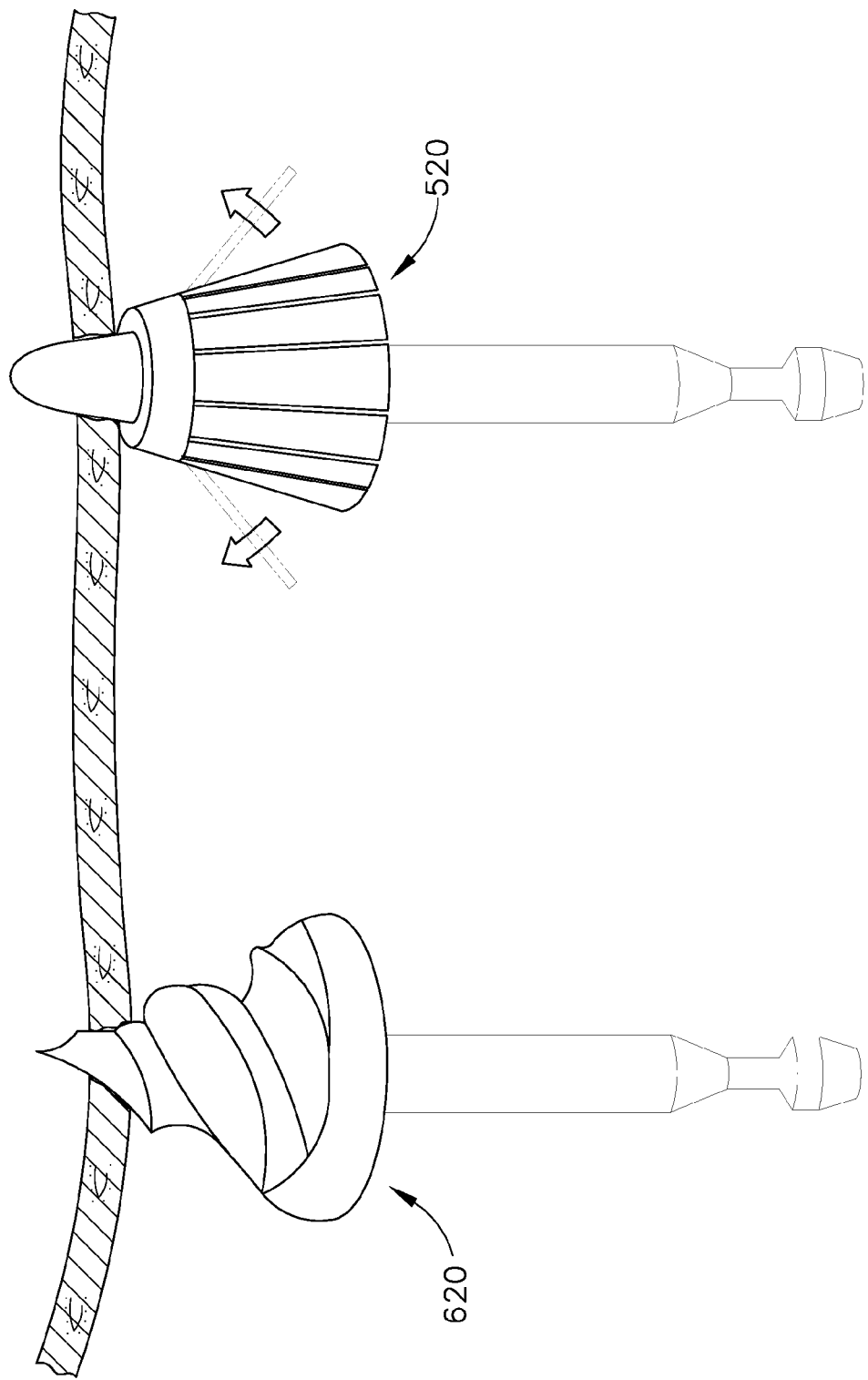
FIG. 22 is a partial side view of additional anvil assembly embodiments of various forms of the present invention used to puncture through the colon wall.

FIGS. 20 and 21 illustrate a section of colon 600 that has a diseased portion 602 that is to be removed therefrom. As can be seen in FIG. 21, a circular stapling instrument 10 of the type and constructions described above with a corresponding anvil assembly 420 of the type and construction described above is inserted into the colon 600 through the rectum 604. The anvil assembly 420 is used to puncture through the portions of the colon wall "T" and "T1" when the anvil assembly 420 is in the collapsed position in the manners described above. FIG. 21 illustrates this process generally. As can be seen in that Figure, conventional graspers 610 may be employed through appropriately located trocars (not shown) to grasp the diseased portion 602. Those of ordinary skill in the art will understand that any of the above-described embodiments may be employed to perform this procedure. FIG. 22 illustrates anvil assembly 520 as well as a pointed anvil assembly 620 that has an auger-type tip formed thereon to penetrate the colon wall. Once the anvil assembly has penetrated through the colon wall portions "T" and "T1" the circular stapling instrument 10 may be operated as described above to complete the anastomosis 606. Thereafter, the instrument 10 is withdrawn out through the rectum 604.

Figure 23:
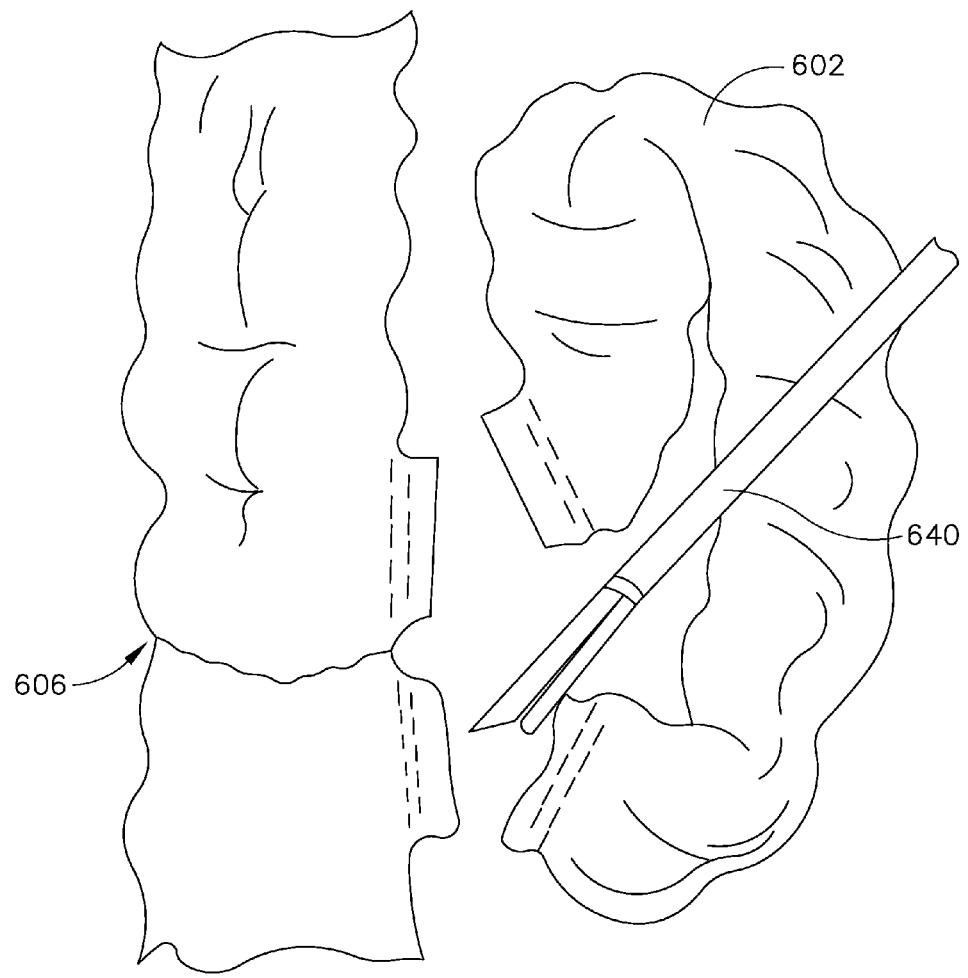
FIG. 23 is a side view of the colon of FIGS. 20 and 21, after the diseased portion has been removed and the ends of the colon have been reconnected using the stapling instrument of FIG. 21.
Figure 24:
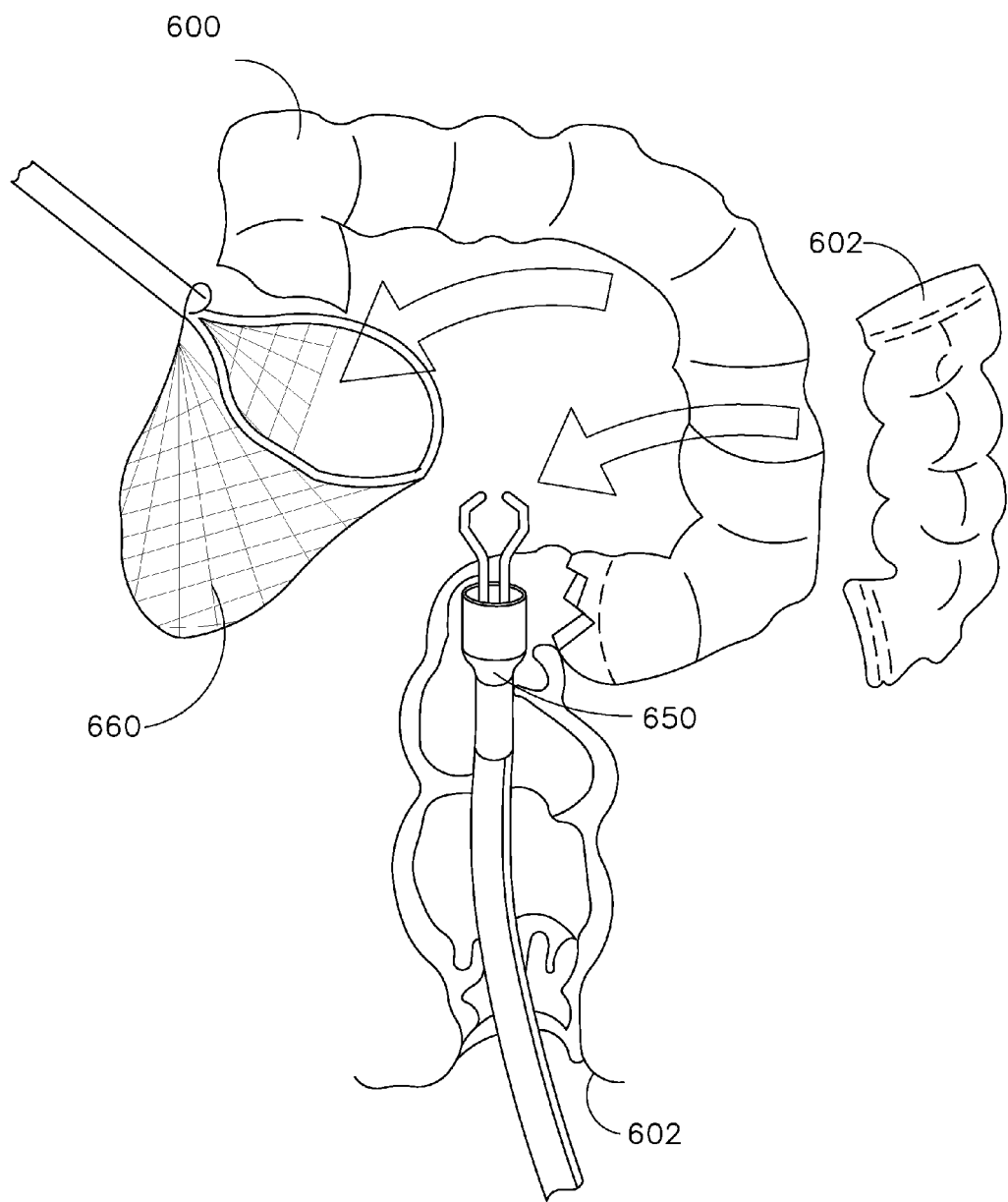
FIG. 24 is another diagrammatic view of the colon of FIGS. 21 and 22 illustrating removal of the diseased colon segment from the patient.

FIG. 23 illustrates use of conventional endocutter devices 640 to sever the diseased colon portion 602. Again the endocutter 640 may be inserted through an appropriately located trocar. FIG. 24 illustrates removal of the diseased portion by inserting a conventional specimen retrieval device 650 through the colon 600 to grab the specimen 602 and either withdraw it back out through the rectum 604 or to place it in a specimen retrieval bag 660 inserted through another appropriately placed trocar.

As can be appreciated from the foregoing, the various circular stapling instrument configurations and anvil assembly configurations described herein represent vast improvements over prior circular stapler arrangements. Use of the various circular stapling instrument and anvil embodiments of the present invention may eliminate the often time-consuming process of tying purse string sutures around the anvil shaft. In addition, the various anvil assemblies disclosed above may be effectively used with conventional circular stapling instruments. Such self-puncturing and self centering anvil arrangements may also eliminate the need for creating "side-to-side" anastomosis. Various anvil assembly embodiments of the present invention described above may also result in a reduction of the insertion and removal forces needed to use the instruments. The need for creating another defect to insert an anvil in the patient may also be eliminated when employing various embodiments of the present invention. Such embodiments of the present invention may also result in little or no dilation of the staple line which can lead to better hemostasis.

Figures 25, 26:
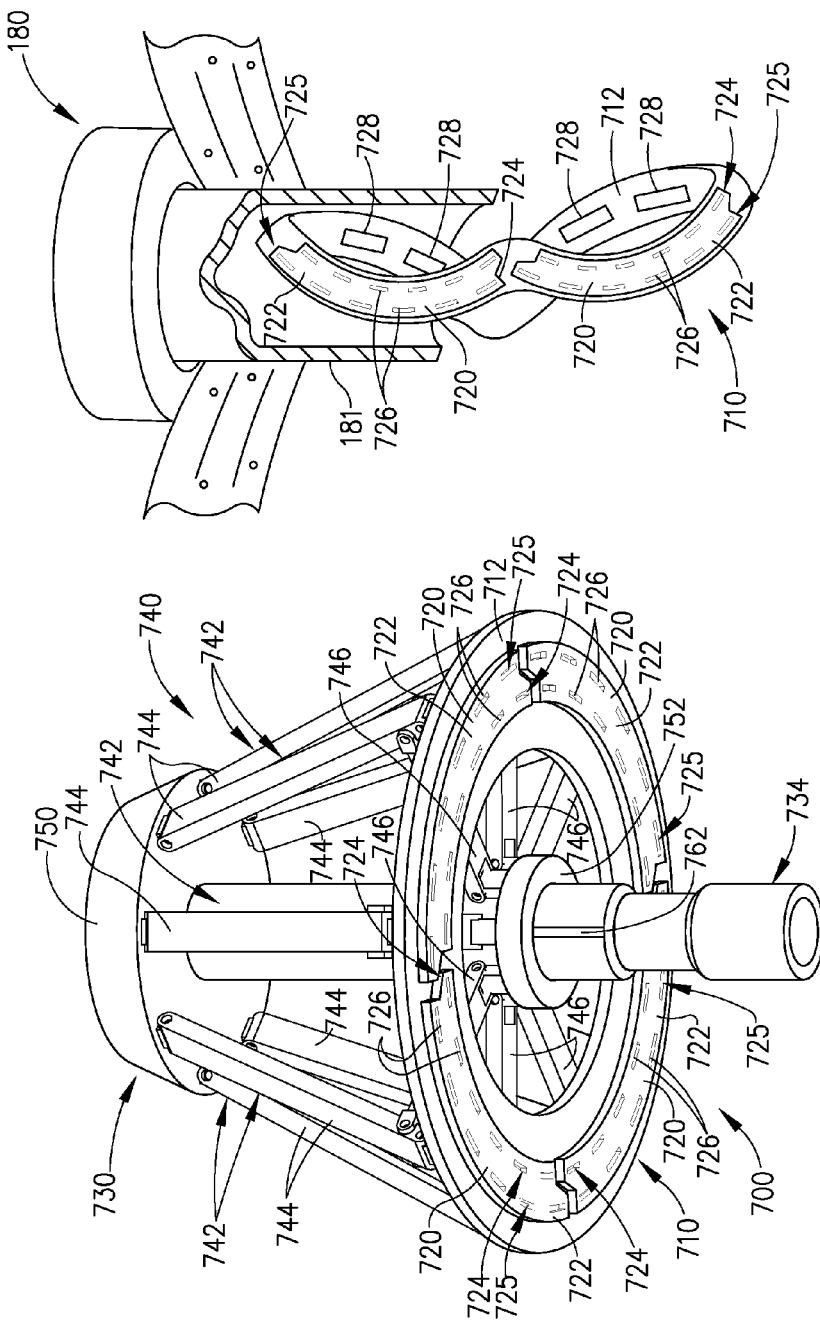
FIG. 25 is a bottom perspective view of another anvil assembly embodiment of one form of the present invention in an expanded or deployed orientation.
FIG. 26 is a diagrammatic view of an anvil plate assembly of FIG. 25 in a collapsed orientation and being inserted through a cannula portion of a trocar device.
Figure 27:
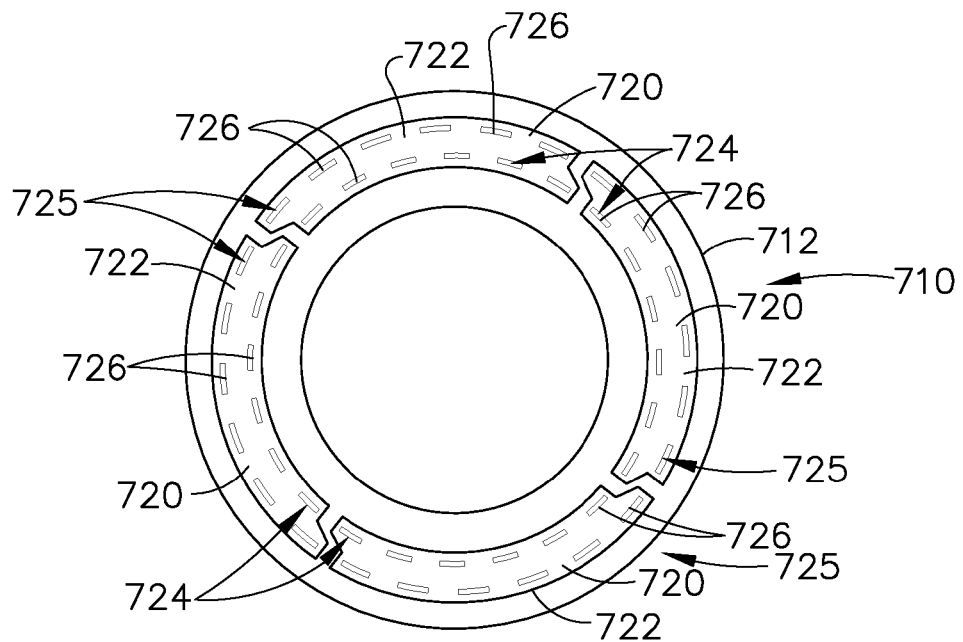
FIG. 27 is a bottom view of the anvil plate assembly of FIG. 26 in the expanded planar orientation.
Figure 28:
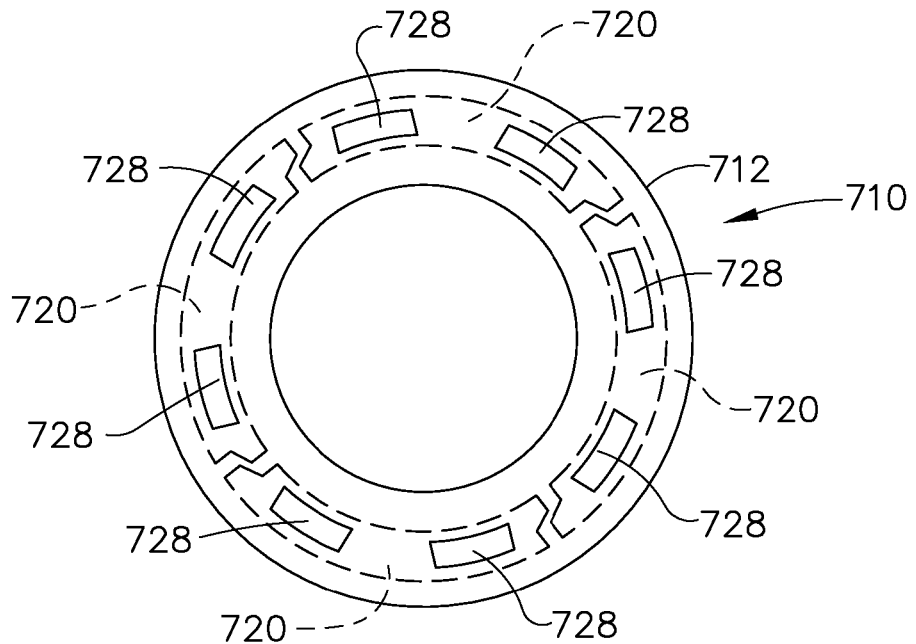
FIG. 28 is a top view of the anvil plate assembly of FIG. 27.

FIGS. 25-28 illustrate another expandable anvil assembly 700 that may be employed with the circular stapling instrument 10 to perform various stapling procedures such as the Roux-en-Y procedure described above. In at least one implementation, the expandable anvil assembly 700 includes an anvil plate assembly 710 that, in at least one embodiment, includes a flexible ring member 712 that supports a plurality of metal anvil plate segments 720 thereon. The flexible ring member 712 may be fabricated from an elastomeric material that permits the ring member 712 to be collapsed into a first configuration which permits it to be inserted through the cannula portion 181 of a trocar device 180 (FIG. 26) and then spring open to a second configuration comprising a substantially planar annular anvil plate assembly 710 as shown in FIGS. 27 and 28. The metal anvil plate segments 720 are arcuate in shape and may be embedded in or otherwise attached to the flexible ring member 712. Each anvil plate segment 720 has a staple-forming surface 722 thereon that has a plurality of arcuate configurations of staple-forming pockets 726 therein. In one embodiment for example, the staple-forming surface 722 has an inner configuration 724 and an outer configuration 725 of staple-forming pockets 726 therein. As can be seen in FIGS. 25-27, the inner configuration 724 of staple-forming pockets 726 is staggered with respect to the outer configuration 725 of staple-forming pockets 726 to match the concentric array of staples in the stapling head 20.

In various embodiments, the expandable anvil assembly 700 further includes an anvil support member 730 that is configured for attachment to the anvil plate assembly 710 to orient and provide load bearing support thereto. As can be seen in FIGS. 25 and 29-31, in at least one implementation, the anvil support member 730 comprises a central shaft 732 that has a proximal end 734 that is configured to be attached to the end of the trocar shaft of the circular stapling device. The proximal end 734 may have a cavity therein sized to receive the trocar tip therein. In other embodiments, the proximal end 734 is configured to releasably engage a trocar shaft arrangement of the type disclosed in FIG. 14.

In at least one implementation, the anvil support member 730 includes a linkage assembly 740 that is movably journaled on the central shaft 732 such that it is movable thereon between a collapsed orientation (FIG. 29) and an expanded or deployed orientation (FIGS. 25 30). As can be seen in FIGS. 25, 29, and 30, the linkage assembly 740 comprises a plurality of jointed links 742 that each include a distal link 744 and a proximal link 746 that are pivotally (pinned) together. In other embodiments, however, each distal link 744 may be coupled to a corresponding proximal link 746 by a living hinge arrangement that includes a detent arrangement to lock the links together when in the anvil plate supporting position. Each of the distal links 744 is pivotally coupled to a distal end ring 750 that is mounted to the distal end of the central shaft 732. Each of the proximal links 746 is pivotally coupled to a lock ring 752 that is movably journaled on the central shaft 732. A retention collar 760, in the form of a plurality of spaced outwardly extending flanges 762, is provided on the central shaft 732 to retainingly engage the lock ring 752 when the linkage assembly 740 is in the expanded or deployed orientation as shown in FIG. 30. When the lock ring 752 is retainingly engaged with the retention collar 760, the linkage assembly 740 is locked in the expanded orientation.

As can be seen in FIGS. 29-31, each of the proximal links 746 has a latch feature 748 formed thereon. The latch feature 748 is adapted to engage a corresponding latch tab 728 formed on the underside 727 of each anvil plate 720. As can be seen in FIG. 28 in at least one embodiment, each anvil plate 720 has two latch tabs 728 thereon. The latch tabs 728 are positioned such that when they latchingly engage the corresponding latch features 748 on the anvil support member 730, the staple-forming pockets 726 in the anvil plates 720 are aligned with corresponding staples in the stapling head of the circular stapling instrument, such that when the staples are driven into the anvil plates 720, the staples are properly formed by the corresponding staple-forming pockets 726 therein. In alternative embodiments, the ends of the links may be configured to retainingly engage corresponding holes in the anvil plates 720.

In use, the anvil plate assembly 710 is oriented in the collapsed orientation so that it can be passed through the cannula portion 181 of the trocar device 180 (FIG. 26) or other opening in the body (e.g., through the colon, etc.). The anvil support member 730 is likewise oriented in the collapsed orientation (FIG. 29) so that it may also pass through the cannula portion 181 or other body opening. It may be attached to the trocar shaft of the circular stapling instrument and inserted through the cannula portion 181 or body opening with the stapling head of the instrument. In other approaches, however, the collapsed anvil support member 730 may be separately inserted into the patient and then attached to the trocar shaft of the circular stapling instrument that has been inserted, for example, through a cannula portion of another trocar device or other opening. Once the anvil plate assembly 730 has passed through the cannula portion 181, the flexible ring 712 causes the plate assembly to flex into its planar orientation. If the anvil support member 730 was inserted through the cannula portion or opening without being attached to the trocar shaft of the circular stapling instrument, with, for example, a grasping device, the surgeon may use the grasping device to move the linkage assembly 740 to the expanded orientation such that the lock ring 752 is brought into locking engagement with the retention collar 760. Thereafter, the expanded anvil support member 730 is mated to the anvil plate assembly 710. More specifically, the anvil plate assembly 710 is oriented relative to the proximal links 746 of the linkage assembly 740 such that the latch features 748 are first oriented adjacent to the corresponding latch tabs 728 on the anvil plates 720 and then rotated into latching engagement therewith as illustrated in FIG. 31. The assembled anvil assembly 700 may then be attached to the trocar shaft of the circular stapling instrument. To ensure that the staple-forming pockets 726 are insubstantial registry with the corresponding staples in the stapling head, the proximal end 734 of the shaft 732 is attached to the trocar shaft in an aligned manner. Such alignment may be accomplished by using the trocar shaft arrangement configured as shown in FIG. 14 or other suitable alignment arrangement (i.e., keys/keyways, grooves, etc.). In applications wherein the anvil assembly 700 is introduced into the patient while it is attached to the trocar shaft of the circular stapling instrument, the surgeon may insert the anvil plate assembly 710 over the collapsed anvil support member 730. Once the anvil plate assembly 710 has been inserted over the collapsed anvil support member 730, the surgeon may then move the anvil support member 730 to the expanded orientation and then the anvil plate assembly 710 may then be attached thereto in the manner discussed above.

FIGS. 32-38 illustrate another anvil plate assembly 810 that can be inserted through a cannula portion 181 of a trocar device 180 or other opening in the body in a collapsed orientation (FIG. 26) and then opened to assume a substantially planar orientation or configuration (FIG. 38). In at least one implementation, the anvil plate assembly 810 includes a plurality of anvil plates 820 that are movably fastened together by a plurality of first and second spring clips 840, 860. Each anvil plate 820 has an arcuate shape such that when configured in the expanded orientation, the anvil plates 820 cooperate to form a substantially annular and planar anvil plate configuration as shown in FIG. 38.

In various embodiments, the ends of the anvil plates 820 are configured to interlock together to form the expanded anvil plate assembly shown in FIG. 38. When assembled together, the anvil plate assembly 810 includes a pair of first attachment joints 821 that are opposed to each other and a pair of second attachment joints 850 that are opposed to each other. See FIGS. 32 and 38. FIGS. 33 and 34 illustrate an exemplary first attachment joint 821. As can be seen in those Figures, the adjacent first ends 822 of the anvil plates 820 forming a first attachment joint 821 each have a first notch 823 therein. Each first end 822 further has a planar first attachment tab 824 protruding therefrom that is sized to slidably extend into a complementary-shaped first slot 825 formed in the first end 822 of the adjoining anvil plate 820. The first ends 822 are movably coupled together by a first spring clip 840. The ends 842 of each first spring clip 840 are movably retained within first spring slots 843 formed in the first ends 822. When the anvil plate assembly 810 is in the collapsed orientation, the first spring clips 840 retain the first ends together as shown in FIGS. 32 and 33. When the anvil plate assembly 810 is in the expanded orientation, the ends 842 of the first spring clips 840 slide in their respective first spring slots 843 to retain the first ends 822 of the anvil plates 820 in interlocked engagement as shown in FIGS. 34 and 38.

FIGS. 35-37 illustrate a second attachment joint 850. As can be seen in those Figures, the adjacent second ends 852 of the attachment plates 820 forming a second attachment joint 850 each have a second notch 853 therein. Each second end 852 further has a planar second attachment tab 854 protruding therefrom that is sized to extend into a complementary-shaped second slot 855 formed in the second end 852 of the adjoining anvil plate 820. The second ends 852 are movably coupled together by a second spring clip 860. The ends 862 of each second spring clip 860 are movably retained within second spring slots 863 formed in the second ends 852. When the anvil plate assembly 810 is in the collapsed orientation, the second spring clips 860 retain the second ends 852 together as shown in FIGS. 32 and 35. When the anvil plate assembly 810 is in the expanded orientation, the ends 862 of the second spring clips 860 slide in their respective second spring slots 863 to retain the second ends 852 of the anvil plates 820 in interlocked engagement as shown in FIGS. 36 and 38. In various embodiments, the attachment tabs 824, 854 are substantially parallel with the staple-forming surfaces on the anvil plates 820 such that when the anvil plates 820 are assembled together in the expanded orientation, the attachment tabs 824, 854 provide additional support and rigidity to the anvil plate assembly 810 in the plane that is substantially perpendicular to the direction in which the staples are being fired.

Each anvil plate segment 820 has a staple-forming surface 870 thereon that has a plurality of arcuate configurations of staple-forming pockets 876 therein. In one embodiment for example, the staple-forming surface 870 has an inner configuration 872 and an outer configuration 874 of staple-forming pockets 876 therein. When in the expanded orientation, the anvil plate assembly 810 may be attached to the anvil support member 730 and used in the manner described above. In particular, each of the anvil plates 820 may have two latch tabs (not shown) formed on the underside thereof. The latch tabs are positioned such that when they latchingly engage the corresponding latch features 748 on the anvil support member 730, the staple-forming pockets 876 in the anvil plates 820 are aligned with corresponding staples in the stapling head of the circular stapling device, such that when the staples are driven into the anvil plates 820, the staples are properly formed by the corresponding staple-forming pockets 876. As shown in FIG. 32, a tether 880 may be employed to retain the anvil assembly 810 in the collapsed orientation during insertion into the patient. Thereafter, the tether 880 may be cut using a conventional cutting device 890 to permit the anvil assembly 810 to be moved to the expanded orientation.

Figure 41:
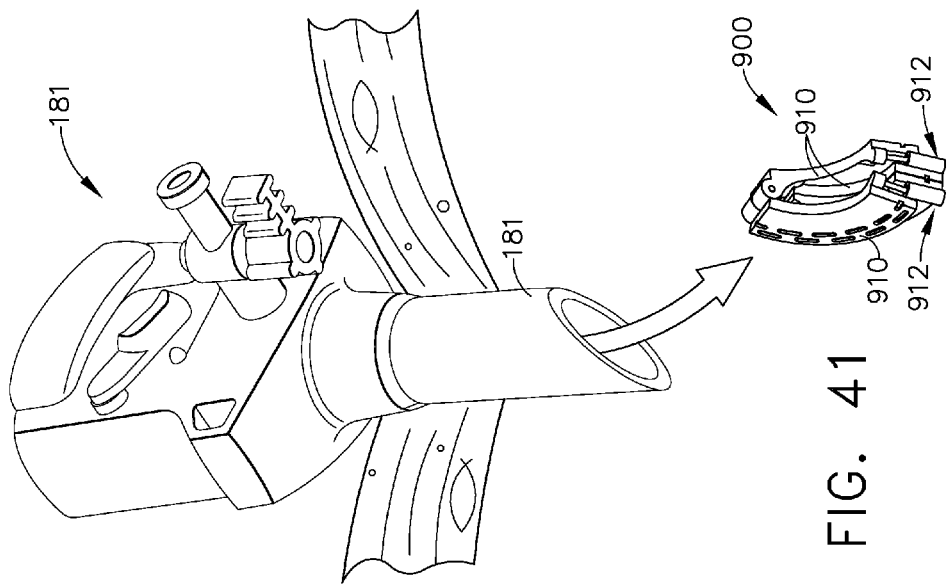
FIG. 41 is a partial perspective view illustrating insertion of the anvil plate assembly embodiment of FIGS. 39 and 40 in a collapsed orientation and inserted through a trocar cannula.

FIGS. 39A-39F, 39AA, 39CC, 40, 40A, and 41 illustrate another expandable anvil plate assembly 900 of the present invention. In one implementation, the anvil plate assembly 900 includes four arcuate anvil plate segments 910 that are coupled together by hinges 912, 912', 912". FIGS. 39A, 39B, and 39AA illustrate the anvil plate assembly 900 in a completely collapsed configuration. In the illustrated embodiment, the anvil plate assembly 900, when in the completely collapsed configuration, is sized to fit through the cannula portion 181 of a trocar device 180 that has a 12 mm opening. See FIG. 41. As can be seen in that Figure, the hinges 912 are partially separatable to enable the plate assembly 900 to assume that position. Once the anvil assembly 900 has been inserted through the trocar cannula 181 or other body opening, the anvil assembly 900 is unfolded as illustrated in FIGS. 39C-39F and 39CC to form a substantially planar anvil plate assembly 900. Each of the anvil plate segments 910, which may be fabricated from metal material, has a staple-forming surface 914 that has an inner configuration 916 of staple-forming pockets 918 and an outer configuration 920 of staple-forming pockets 918 therein.

Figure 42:
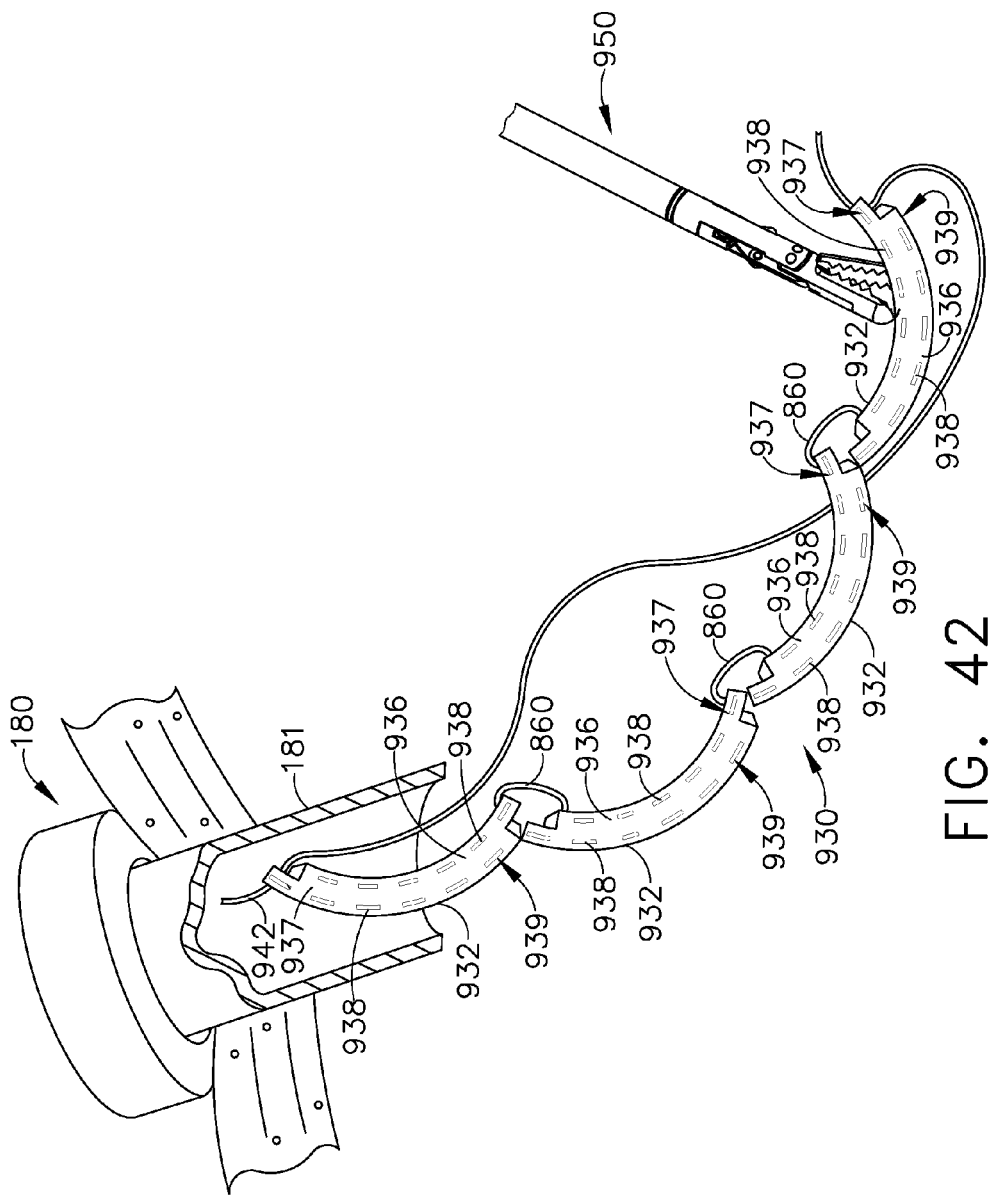
FIG. 42 is a diagrammatic view illustrating insertion of another anvil plate assembly embodiment of another form of the present invention in a collapsed orientation and inserted through a trocar cannula.

FIG. 42 illustrates another expandable anvil plate assembly 930 of the present invention. In one implementation, the anvil plate assembly 930 includes four arcuate anvil plate segments 932 that are coupled together by hinges 934. In the illustrated embodiment, a tether 940 is threaded through each of the segments 932. The collapsed anvil assembly 930 may be pulled through the trocar cannula 181 by a conventional grasping instrument 950 that has been inserted through another trocar device (not shown). As the collapsed anvil assembly 930 is inserted through the cannula 181, the end 942 of the tether is threaded out through the cannula 181 where it can be accessed outside of the trocar device 180. Once the collapsed anvil plate assembly 930 has been inserted through the cannula portion 181, the surgeon may then pull the end 942 of the tether 940 to draw the two end anvil plate segments 932 together to form the substantially planar annular anvil plate assembly. A releasable latch feature (not shown) is provided on each of the end segments to lock the anvil assembly 930 in the expanded configuration. As can be seen in FIG. 42, each of anvil plate segments 932, which may be fabricated from metal material, has a staple-forming surface 936 that has an inner configuration 937 of staple-forming pockets 938 and an outer configuration 939 of staple-forming pockets 938 therein.

Figure 43:
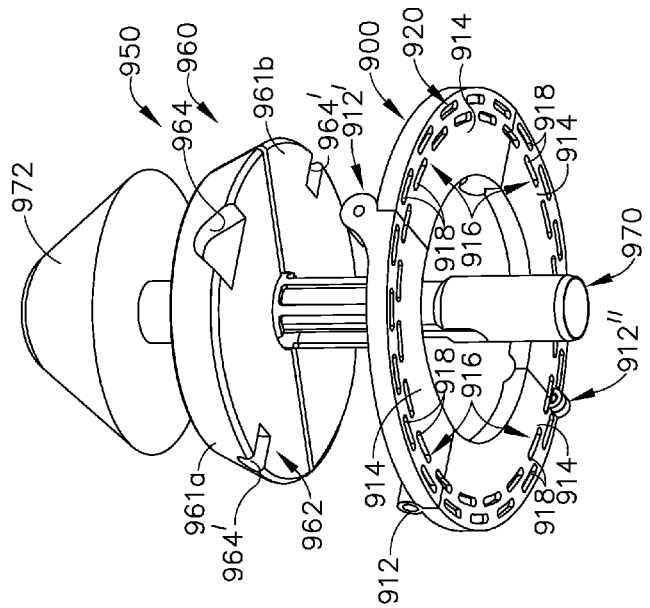
FIG. 43 is an exploded perspective view of another anvil assembly embodiment of another form of the present invention.

While the anvil plate assemblies 900, 930 may be employed with any of the anvil support member arrangements disclosed herein, FIG. 43 illustrates another anvil support member arrangement 950 of the present invention. One implementation of the anvil support member arrangement 950 includes an anvil bearing plate assembly 960 that is journaled on an anvil shaft 970. The anvil assembly 900, 930 (whichever the case may be) is inserted through the cannula portion 181. The anvil shaft 970 is also sized to be inserted through the cannula portion 181 or other body opening. The bearing plate assembly 960 may, for example, comprise two bearing plate halves 961a, 961b that are hingably coupled together. Such arrangement permits the bearing plate assembly 960 to be folded to a collapsed position wherein it may be inserted through the cannula portion 181 or other body opening. Once all three components 900 or 930, 960, 970 have been inserted into the patient, they may be assembled as shown in FIGS. 43 and 43A-43C. The bearing plate assembly 960 may be keyed onto the anvil shaft 970 to orient the bearing plate 960 in a desired orientation thereon. The anvil shaft 970 is configured to be attached to the trocar tip of the surgical stapling instrument in a desired orientation. The anvil shaft 970 may, for example, be configured as shown in FIG. 14. The bearing plate assembly 960 may also be configured to latch in position with the anvil shaft 970 or latch with the end cap 972 of the anvil shaft. As can also be seen in FIG. 43, in the illustrated embodiment, the underside 962 of the bearing plate assembly 960 is configured to latch with the particular anvil plate assembly 900, 930. In the depicted embodiment, a notch 964 is provided to receive the hinge 912' therein. The underside 962 further has notches 964' that are sized to receive the hinges 912 therein. The notches 964, 964' are sized to snappingly receive a portion of the hinges 912', 912 therein. Thus, when the anvil has been completely assembled and attached to the trocar shaft, the staple-forming pockets in the anvil plate assembly are properly aligned (i.e., insubstantial registry) with the staples in the stapling head of the circular stapling instrument.

Figure 45:
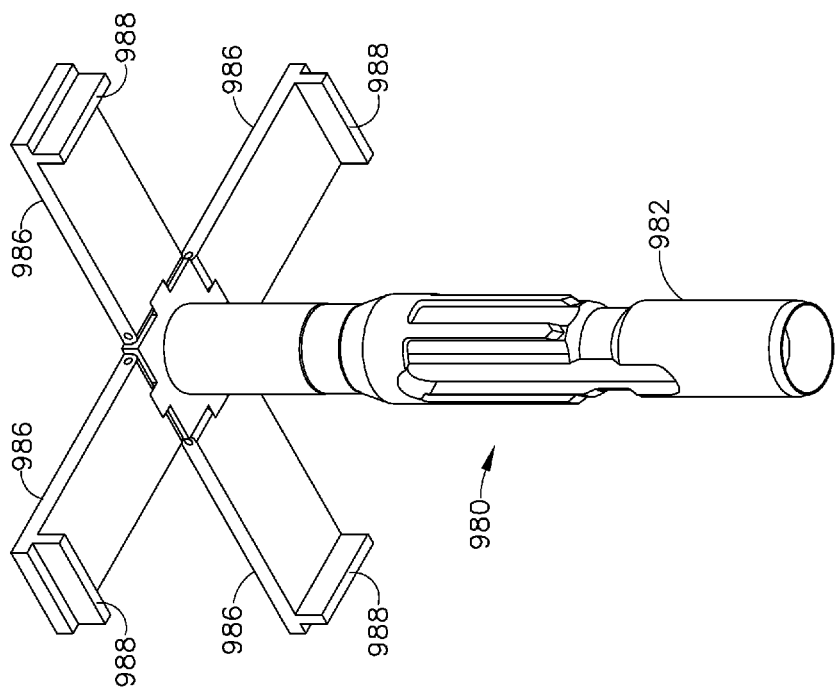
FIG. 45 is another perspective view of the anvil support member embodiment of FIG. 44 in an expanded or deployed orientation.
Figure 44:
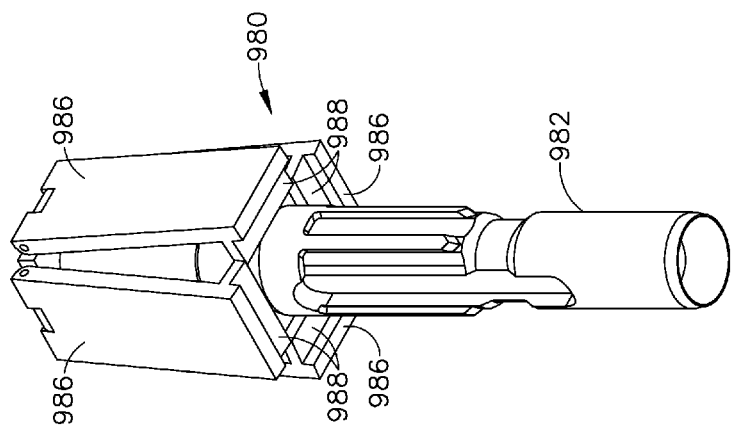
FIG. 44 is a perspective view of another anvil support member embodiment of another form of the present invention in a collapsed orientation.

FIGS. 44 and 45 illustrate another collapsible anvil support member 980 that may be used to support any of the anvil plate assemblies disclosed herein. As can be seen in those Figures, the anvil support member 980 includes an anvil shaft 982 that has a proximal end 984 that is configured to be attached to the tip of a trocar of a circular stapling instrument. The anvil shaft 982 is configured to be attached to the trocar tip of the surgical stapling device in a desired orientation. The anvil shaft 982 may, for example, be configured as shown in FIG. 14 to be attached to the trocar tip. In addition, the anvil support member 980 further includes a plurality of anvil support arms 986 that are pivotally coupled to the anvil shaft 982. The anvil support arms 986 may be configured with a detent or other latching arrangement such that when they are pivoted to the open position illustrated in FIG. 45, they are releasably locked in that position. In other embodiments, no latching arrangement is employed.

As can be seen in FIG. 45, each of the anvil support arms 986 has a latch tab 988 thereon that is configured to latch with the anvil plate assembly when the anvil plate assembly is in the open planar position. A variety of latch tab arrangements may be employed. In one embodiment, the tabs 988 may be configured to be pressed into openings in the anvil plate assembly. One of the tabs 988 may be sized or located such that it can only latch with a corresponding one opening or latch tab in the anvil plate assembly to properly orient the anvil plate assembly relative to the anvil shaft. Such arrangement serves to ensure that the staple-forming pockets in the anvil plate assembly are properly aligned with the staples in the stapling head when the anvil shaft has been properly attached to the trocar shaft in a desired orientation.

FIGS. 46-52 illustrate another expandable anvil support member 1000 that may be employed with the circular stapling device 10 or other circular stapling devices with the changes/modifications noted below to perform various surgical stapling procedures. In at least one implementation, the expandable anvil support member 1000 that may be used in connection with an anvil plate assembly 1080 or any of the other anvil plate assembly embodiments disclosed herein.

In various embodiments, the expandable anvil support member 1000 includes a central shaft 1010 that has a hollow proximal end 1012 that is sized to receive a tip 1102 of a trocar shaft 1100 of the circular stapling instrument 10. A plurality of engagement tabs 1014 are provided in the proximal end 1012 and have a locking detent or ledge 1016 formed thereon that are designed to snap into an undercut 1104 in the trocar shaft 1100. See FIGS. 46-48. Other latching arrangements may be employed to affix the central shaft 1010 to the trocar shaft 1100. Also in various implementations, a plurality (e.g., four) of pivot shafts 1018 transversely protrude from the central shaft 1010 and define pivot axes PA-PA that are substantially transverse to the shaft axis SA-SA. The distal end 1019 of the central shaft 1010 is flared as shown.

An embodiment of the expandable anvil support member 1000 further includes a hollow locking sleeve 1020 that is movably journaled on the central shaft 1010. The locking sleeve 1020 has a plurality of slots 1022 that are oriented to permit the pivot bars 1018 to slidably extend therethrough. The distal end 1024 of the locking sleeve 1020 has a deformable retention ring 1030 attached thereto that is configured to interact with a centrally disposed hub portion 1031 that extends through the stapling head 20 as shown. In its initial undeformed configuration, the retention ring 1030 is located at the distal end 1033 of the central hub 1031 and permits the trocar shaft 1100 to freely pass therethrough. As the trocar shaft 1100 is drawn in the proximal direction, the pivot shafts 1018 will contact the bottom of the slots 1022 in the locking sleeve 1020 thereby drawing the locking sleeve 1020 in the proximal direction as well. As the retention ring 1030 is drawn into the central hub portion 1031, the retention ring 1030 deforms into frictional contact with the inside wall of the central hub 1031 to retain the locking sleeve 1020 in position as will be discussed in further detail below.

Figure 52:
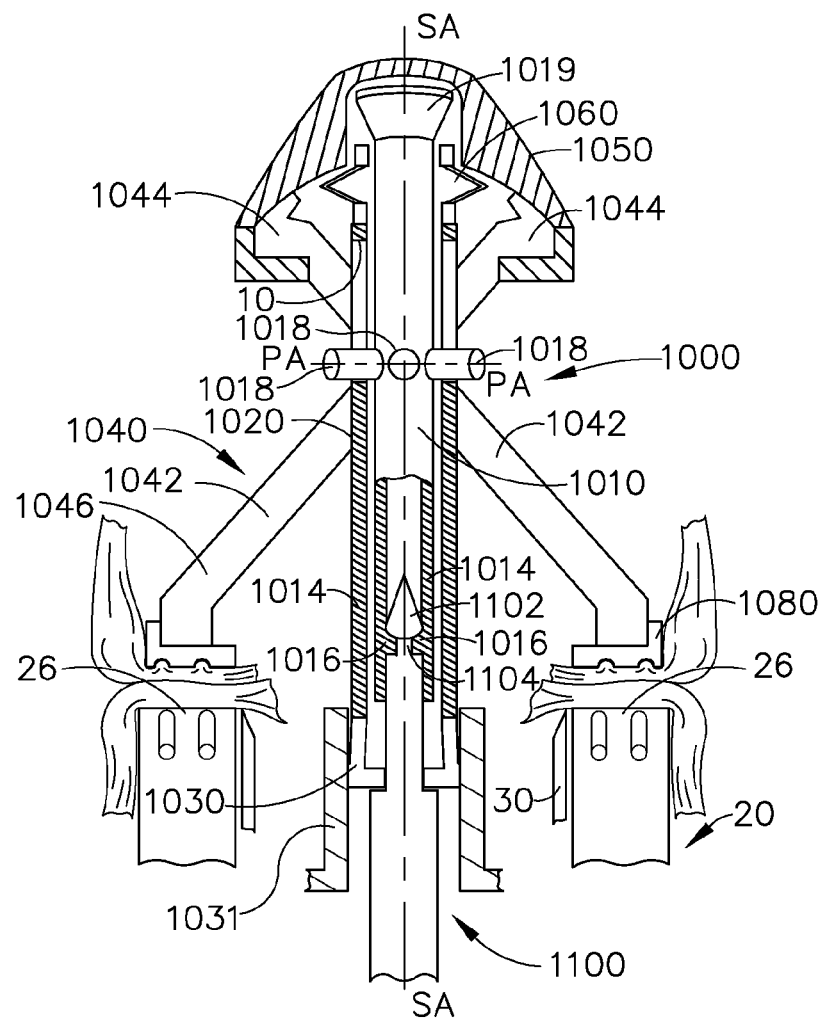
FIG. 52 is another cross-sectional view of the anvil assembly embodiment of FIGS. 46 and 47 prior to firing the circular stapling instrument.

In various implementations, the anvil support member 1000 further includes a movable linkage assembly 1040 that comprises two pairs (only one pair of linkage bars 1042 are shown in the Figures) of diametrically opposed linkage bars 1042 that are pivotally coupled to the pivot shafts 1018. For example, FIGS. 46, 47, and 52 depict two diametrically opposed linkage bars 1042 that are pivotally coupled to the central shaft 1010 about the pivot shafts 1018. Each linkage bar 1042 has a notched distal end 1044 that is configured to retainingly engage a shaft cap 1050 that is journaled over the distal end 1019 of the shaft 1010. The shaft cap 1050 is sized such that it may be inserted through a specific size of trocar cannula or other opening in the body. Each of the linkage bars 1042 has a proximal end 1046 that is configured to be latched to an anvil plate assembly 1080. Any of the latching arrangements disclosed herein may be employed to latch the anvil plate assembly 1080 or any of the other anvil plate assemblies disclosed herein to the proximal ends 1046 of the linkage bars 1042.

Various embodiments of the anvil support member 1000 further include a distal locking collar 1060 that is attached to the distal end 1022 of the locking sleeve 1020. FIGS. 50 and 51 illustrate one method of manufacturing the distal locking collar 1060. In various embodiments, the distal locking collar 1060 may comprise a hollow sleeve and which has a plurality of longitudinal slits 1062 equally spaced around its circumference. See FIG. 50. As can also be seen in FIG. 50 in its initial "unlocked" or "unformed position" the center of the sleeve 1060 may have a central outer diameter "D1" that is larger than its end diameters "DE". When axial forces "AF" are applied to the ends of the distal locking collar 1060, the collar collapses axially thereby increasing the central outer diameter ("D2" is larger than "D1").

In use, the anvil support member 1000 and the expandable anvil plate assembly 1080 (or any of the other anvil plate assemblies disclosed herein) may be separately introduced into the patient's body through, for example, a trocar cannula or other body opening. FIG. 46 illustrates the attachment of the anvil support member 1000 to the trocar shaft 1100. As can be seen in that Figure, the anvil plate assembly 1080 has been attached to the proximal ends 1046 of the linkage bars 1040. Once the central shaft 1010 has been attached to the trocar shaft 1100, the surgeon may then start to draw the anvil support member 1000 proximally ("PD") toward the stapling head 20 by rotating the knob 40 of the circular stapling instrument. As the shaft 1010 is drawn proximally, pivot shafts 2018 will contact the bottom of the respective slot 1022 from which they protrude in the locking sleeve 1020. In addition as the central shaft 1010 is drawn proximally, the distal locking collar 1060 will be collapsed outward between the distal end 1019 of the shaft 1010 and the distal end 1022 of the locking sleeve 1020. As shown in FIG. 47 as the distal locking collar 1060 collapses into retaining engagement with the notched distal ends 1044 of the linkage bars 1040 to retain them in engagement with the shaft cap 1050. Such configuration permanently retains the linkage bars 1040 in their expanded or deployed orientation.

The surgeon may then continue to draw the trocar shaft 1100 proximally which draws the anvil support member 1000 and the anvil plate assembly 1080 toward the stapling head 20. As the shaft 1010 and the locking sleeve 1020 are drawn proximally, the retention ring 1030 is biased radially inward (arrows "R" in FIG. 47) into the central hub portion 1031. As the retention ring 1030 is drawn into the central hub portion 1031, the retention ring 1030 deforms into frictional contact with the inside wall of the central hub portion 1031 to retain the locking sleeve 1020 in position. This embodiment may be employed to perform a variety of surgical procedures including those procedures described above.

FIGS. 53-57 illustrate another collapsible and expandable anvil support member 1200 that may be effectively employed with any of the anvil plate assemblies described herein. In at least one implementation, the anvil support member 1200 includes a central shaft 1210 that has a distal end 1212 and a proximal end 1214. The proximal end 1214 may be configured as illustrated in FIG. 14 to be releasably attached to a trocar shaft of a circular stapling instrument. In other embodiments, the proximal end 1214 may be latched onto the tip of a trocar shaft as described above. In still other arrangements, the proximal end 1214 may be keyed onto the trocar shaft to properly orient the staple support member 1200 relative to the staple cartridge supported within the stapling head of the circular stapling instrument. In each case, it is desirable to properly orient the staple support member 1200 relative to the stapling head and staple cartridge therein so that when an anvil plate assembly is attached thereto, the staple-forming-surface and staple-forming pockets therein are properly oriented to form the staples as they are driven into the anvil plate assembly.

As can also be seen in FIGS. 53-56, in at least one implementation, an anvil cap 1220 is attached to the distal end 1212 of the central shaft 1210. The anvil cap 1220 is sized to pass through a trocar cannula or other size of opening in the body. The anvil cap 1220 may be configured with an arcuate dome-shaped surface 1222 to facilitate easy passage through the body without inadvertently injuring adjacent tissue. However, in other implementations, the anvil cap 1220 may be configured to puncture through tissue to enable the anvil support member to be used to perform certain procedures described above.

Figure 56:
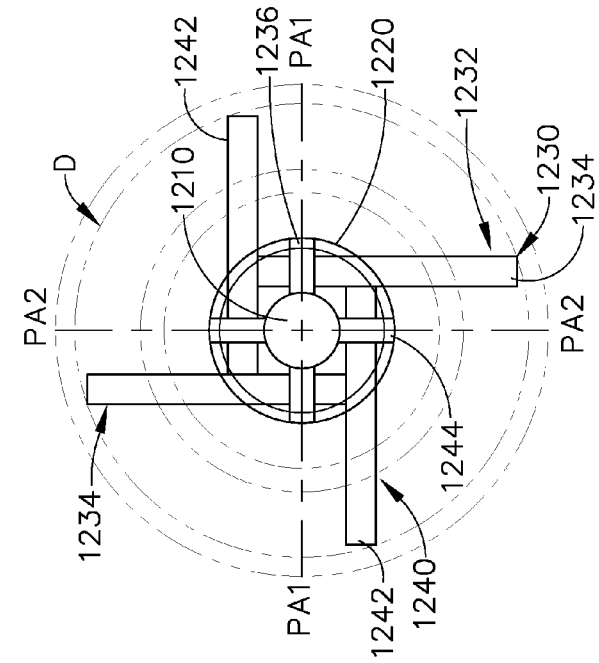
FIG. 56 is a top view of the anvil support member of FIGS. 54 and 55 with the linkage assembly thereof in the open or expanded position.
Figure 57:
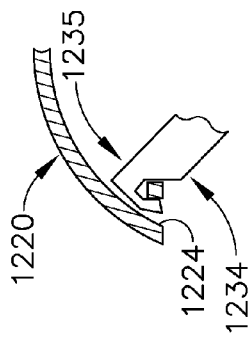
FIG. 57 is a partial cross-sectional view of a portion of the anvil cap and a linkage bar illustrating a latch configuration of at least one embodiment of one form of the present invention.
Figure 55:
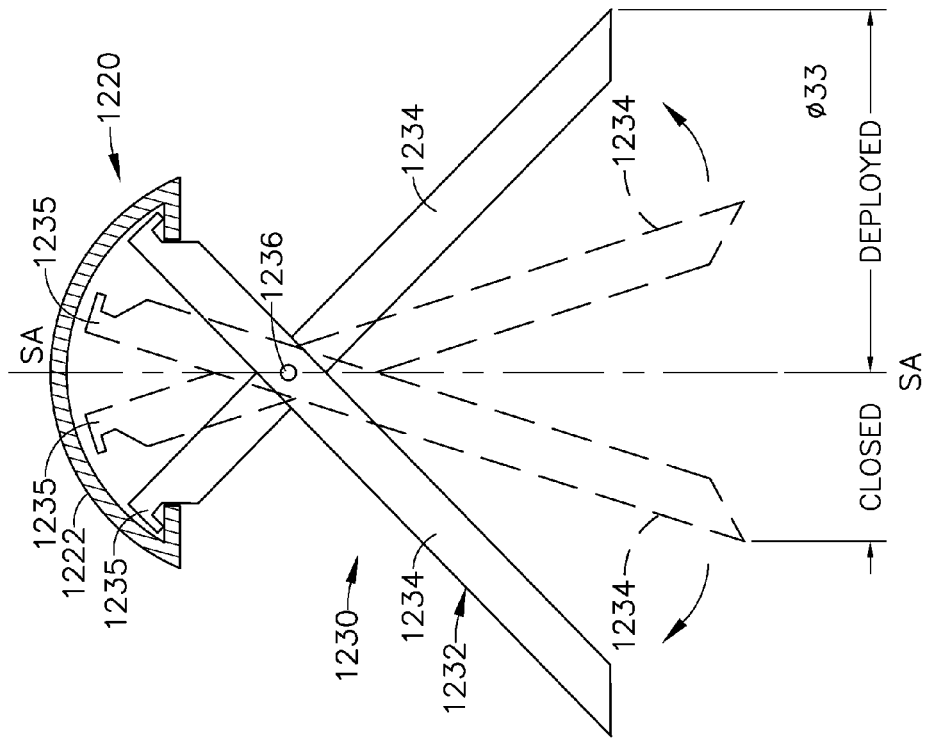
FIG. 55 is a side view of a portion of the anvil support member of FIGS. 53 and 54 illustrating a range of motion of the linkage bars thereof.
Figure 61:
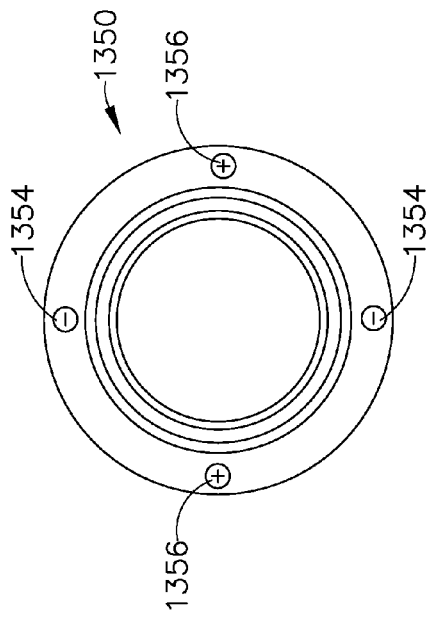
FIG. 61 is a top view of an anvil plate assembly embodiment of the present invention.

Various implementations of the anvil support member 1200 further include a linkage assembly 1230 that is movably journaled on the central shaft 1210. In various embodiments, the linkage assembly 1230 may include two pairs of linkage bars that are pinned to the distal end of the shaft 1210. More specifically, as can be seen in FIG. 56, the linkage assembly 1230 includes a first pair 1232 of diametrically opposed first linkage bars 1234 that are pivotally coupled to the central shaft 1210 about a first pivot shaft 1236 that defines a first pivot axis "PA1"-"PA1" that is substantially transverse to the shaft axis "SA"-"SA". The linkage assembly 1230 further includes a second pair 1240 of diametrically opposed second linkage bars 1242 that are pivotally coupled to the central shaft 1210 about a second pivot axis 1244 that defines a second pivot axis "PA2"-"PA2" that is substantially transverse to the shaft axis "SA"-"SA". Such arrangement permits each of the linkage bars 1234, 1242 to pivot in a corresponding plane that is offset from the center of the shaft 1210. This arrangement permits simple rotation of the linkage bars 1234, 1242 to cross each other when expanded (FIGS. 54 and 56), but to be rotated flat along the shaft 1210 (FIG. 53) and capable of fitting down a trocar cannula for rotation. For example, in at least one implementation, the diameter of the anvil cap 1220 is approximately slightly less than −15 mm diameter. When in the collapsed or closed position (FIGS. 53 and 55), the anvil support member 1200 may pass down a trocar cannula that has a diameter that is approximately 15 mm. When in the expanded position, however, the proximal ends of the linkage bars may open to a diameter "D" of approximately 35 mm. See FIG. 56. Of course, the anvil support member 1200 may be provided in different sizes to accommodate different cannula and opening sizes without departing from the spirit and scope of the present invention.

Also in various implementations, each of the first latch bars 1234 has a notched distal end 1235 that is configured to latching engage a corresponding first latch feature/cavity 1224 in the anvil cap 1220 when the linkage assembly 1230 is in the deployed or expanded orientation. See FIG. 57. Similarly, each of the second latch bars 1242 has a notched distal end 1244 that is configured to latching engage a corresponding second latch feature/cavity (not shown) in anvil cap 1220 when the linkage assembly 1230 is in the deployed or expanded orientation.

As illustrated in FIGS. 53 and 54 each of the first linkage bars 1234 have a first proximal end 1237 that is configured to latchingly engage an anvil plate assembly of any of the types described herein. In one implementation, for example, the first proximal ends 1237 may have a plurality of latch detents 1239 sized to latchingly engage corresponding first latch openings or features in the anvil plate assembly. However, other latch arrangements of the types and construction described above may be employed. Similarly each of the second linkage bars 1242 have a second proximal end 1246 that is configured to latchingly engage the anvil plate assembly. The second proximal end may have second detents 1248 that are sized to latchingly engage corresponding second latch openings or latch features in the anvil plate assembly. The first and second latch features may be configured to latch with the anvil plate in such a way that the anvil plate assembly is properly oriented relative to the stapling head of the instrument when the shaft 1210 has been attached to the trocar shaft of the instrument.

As can also be seen in FIGS. 53 and 54, an elastomeric locking sleeve 1260 is received on the linkage assembly 1230. The locking sleeve 1260 may have an open ended conical shape. The bias of the locking sleeve 1260 forces the first and second linkage bars 1234 and 1242 to the expanded or open position when unconstrained. When in that collapsed or undeployed position, the biasing force generated by the locking sleeve 1260 is not great enough to cause the first and second linkage bars 1234, 1242 to latchingly engage the anvil cap 1250. However, when the linkage bars 1234, 1242 are moved to their expanded or deployed orientation, the locking sleeve forms a set of rigid triangles locking the anvil support member 1200 and sufficiently strong to support the loads of forming staples. This embodiment may be employed to perform a variety of surgical procedures including those procedures described above.

Figure 60:
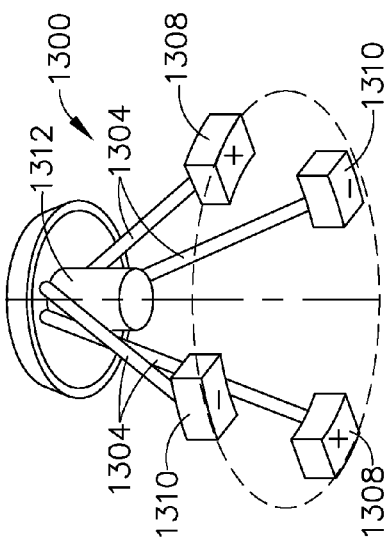
FIG. 60 is a bottom perspective view of another anvil support member embodiment of one form of the present invention.
Figure 63:
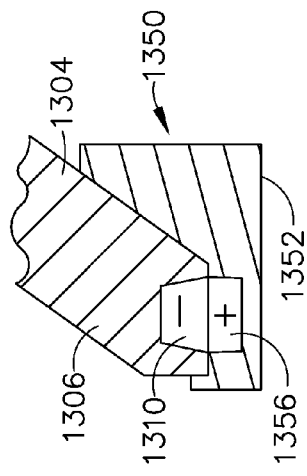
FIG. 63 is another partial cross-sectional view of the linkage bar and anvil plate of FIG. 62 after being coupled together.
Figure 62:
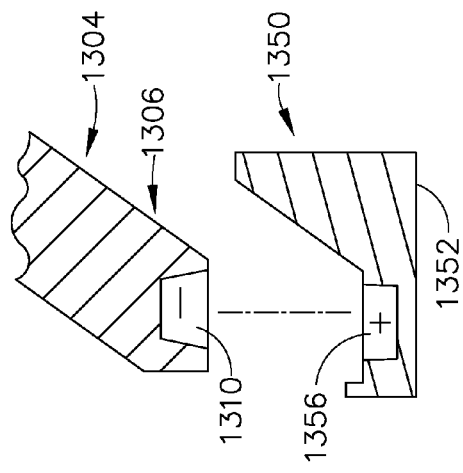
FIG. 62 is a partial cross-sectional view of a portion of a linkage bar and anvil plate assembly of FIGS. 60 and 61 prior to being coupled together.

FIGS. 58-63 illustrate, in diagrammatic form, a method of attaching an anvil support member 1300 to an anvil plate assembly 1350. Those of ordinary skill in the art will understand that features of the anvil support plate 1350 may be employed in connection with any of the anvil support member embodiments and any of the anvil plate assembly embodiments disclosed herein. As can be seen in FIGS. 58-60, the anvil support member 1300 has a linkage assembly 1302 that comprises a plurality of linkage bars 1304. In the depicted embodiment, the linkage bars 1304 are shown in the deployed or open position. In the depicted embodiment, an elastomeric locking sleeve 1311 is received on the linkage bars 1304 as shown in FIG. 58.

Each of the linkage bars 1304 has a magnet attached to its proximal end 1306. In particular, those linkage bars 1304 that are diametrically opposed to each other have a like-poled magnet attached thereto. As such, in ant least one form, two opposed linkage bars 1304 have a positively poled magnet 1308 attached thereto and the other two opposed linkage bars 1304 have a negatively poled magnet 1310 attached thereto. See FIGS. 59 and 60. The anvil plate assembly 1350 has a staple-forming surface 1352 thereon that has staple-forming pockets therein (not shown) that are configured to form staples as they are driven from the stapling head of the stapling instrument to which the anvil assembly is attached.

As with the various anvil support members described above, the shaft portion 1312 of the anvil support member 1300 is configured to be attached to the trocar shaft of the circular stapling instrument. Various methods of attaching the anvil support member to the trocar in a specific orientation (keys, locking tabs, detents, etc.) have been disclosed. In at least one implementation, the anvil plate assembly 1350 has a plurality of magnets attached thereto or embedded therein that are arranged to mate with the magnets 1308, 1310 of the staple support member 1300. When the anvil plate assembly 1350 is attached to an anvil support member 1300 that has been properly coupled to the trocar shaft of a surgical stapling instrument, the staple-forming surface 1352 of the anvil plate assembly 1350 is properly oriented relative to the surgical staples within the stapling head of the instrument. As such, the negative poled magnets 1354 are oriented within the anvil plate assembly 1350 to magnetically couple to the positive poled magnets 1308 attached to the anvil support member 1300 and the positive poled magnets 1356 are oriented to magnetically couple to the negative poled magnets 1310 on the anvil support member 1300.

Figure 64:
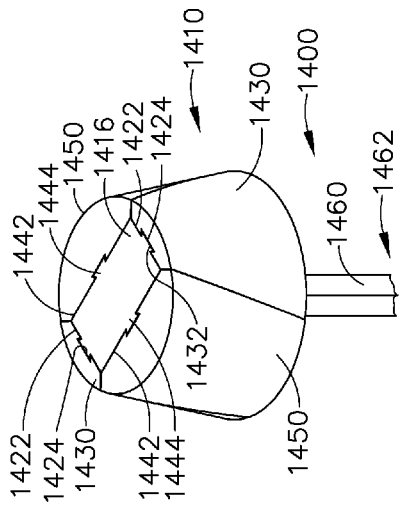
FIG. 64 is a bottom perspective view of another anvil assembly embodiment of the present invention in an expanded orientation.
Figure 65:
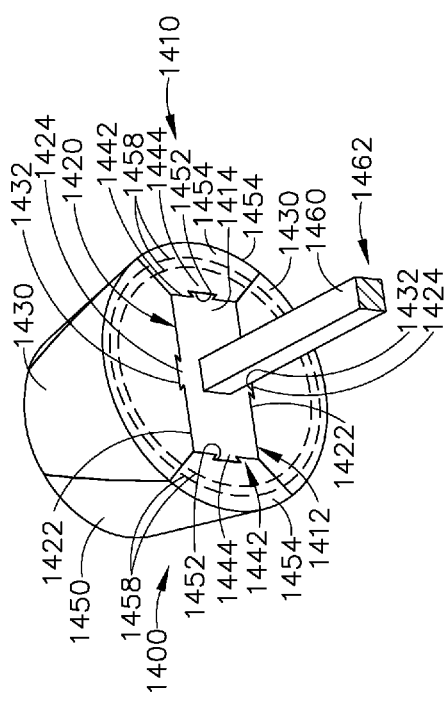
FIG. 65 is another perspective view of the anvil assembly embodiment of FIG. 64.
Figure 66:
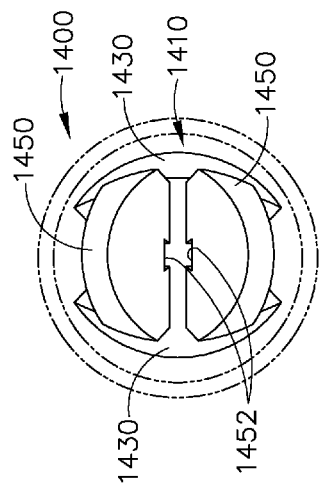
FIG. 66 is a top view of the anvil assembly embodiment of FIGS. 64 and 65.
Figure 67:
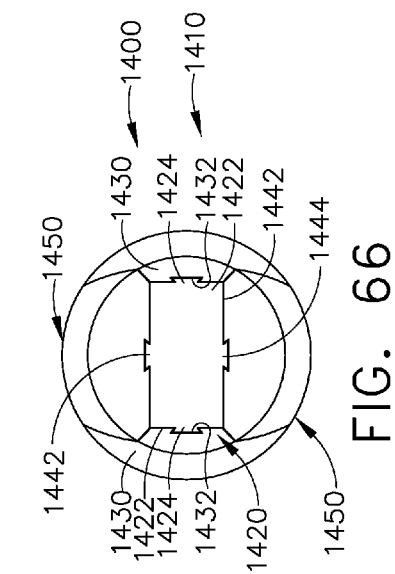
FIG. 67 is another top view of the anvil assembly embodiment of FIGS. 64-66 in a collapsed orientation.

FIGS. 64-70 illustrate another anvil assembly 1400 that is configurable between a collapsed configuration (FIGS. 67, 68, and 70) to an expanded configuration (FIGS. 64-66). The portions of the anvil assembly 1400 may be sized such that when in the collapsed configuration, the anvil assembly 1400 may pass through a particular size of trocar cannula or opening of a particular size. As can be seen in the Figures, the anvil assembly 1400 has an anvil head assembly 1410 that has an anvil shaft 1460 attached thereto. The Figures depict the proximal end 1462 of the anvil shaft with a square cross-section. The proximal end 1462 of the anvil shaft 1460 may have a circular cross-section. In either arrangement, the proximal end 1462 of the anvil shaft 1460 is configured to be attached to the trocar of a circular stapling instrument. Thus, the proximal end 1462 of the anvil shaft 1460 may be configured as shown in FIG. 14. In other embodiments, the proximal end 1462 of the anvil shaft 1460 may have a hollow portion sized to receive the tip of the trocar shaft therein. Locking tabs, detents, etc. may be employed to affix the anvil shaft 1460 to the trocar shaft. See, e.g., the arrangements depicted in FIG. 48. In addition or in the alternative, the proximal end 1462 of the anvil shaft 1460 may be keyed onto the trocar shaft to properly orient the anvil head assembly 1410 relative to the staples support in the stapling head of the stapling instrument.

As can be seen in FIGS. 64-70, the anvil head assembly 1410 includes an anvil body portion 1412 to which the anvil shaft 1430 is attached. In particular, the anvil shaft 1460 is attached to the anvil body portion 1412 such that it protrudes from a bottom surface 1414 thereof. The anvil body portion 1412 has a first pair 1420 of first sides 1422. Each first side 1422 tapers from the bottom surface 1414 to the top surface 1416 of the anvil body portion 1412 as shown. Each first side 1422 has a centrally disposed key 1424 as shown. Slidably attached to each first side 1422 is a first anvil segment 1430. Each first anvil segment 1430 may be shaped as shown in the Figures and have a keyway 1432 that is sized to receive the corresponding first key 1424 therein. Each first anvil segment 1430 has a staple-forming surface 1434 thereon that has an inner line 1435 and an outer lined 1436 of staple-forming pockets 1438. See FIG. 70. As can be seen in FIGS. 68 and 70 each of the first anvil segments 1430 are configured to slide in the proximal direction "PD" relative to the anvil body portion 1412 when the anvil assembly 1400 is in the collapsed orientation.

As can be further seen in FIGS. 64-70, the anvil body portion 1412 has a second pair 1440 of second sides 1442. Each second side 1442 tapers from the bottom surface 1414 to the top surface 1416 of the anvil body portion 1412 as shown. Each second side 1442 has a centrally disposed second key 1444 as shown. Slidably attached to each second side 1442 is a second anvil segment 1450. Each second anvil segment 1450 may be shaped as shown in the Figures and have a keyway 1452 that is sized to receive the corresponding second key 1444 therein. Each second anvil segment 1450 has a staple-forming surface 1454 thereon that has an inner line 1455 and an outer line 1456 of second staple-forming pockets 1458. See FIG. 70. As can be seen in FIGS. 68 and 70 each of the second anvil segments 1450 is configured to slide in the distal direction "DD" relative to the anvil body portion 1412 when the anvil assembly 1400 is in the collapsed orientation.

Figure 71:
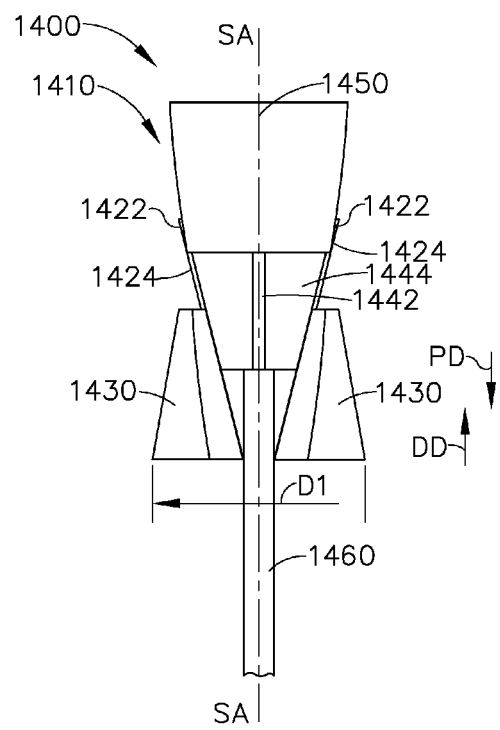
FIG. 71 is a side view of the anvil assembly of FIGS. 64-70 in the collapsed orientation.
Figure 72:
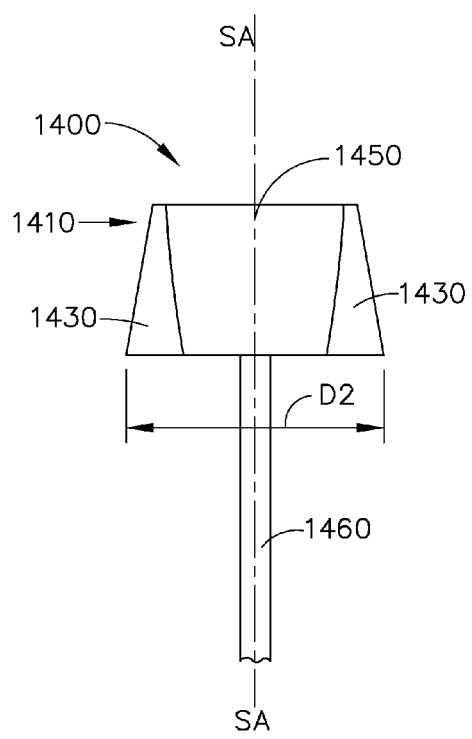
FIG. 72 is another side view of the anvil assembly of FIGS. 64-71 in the expanded orientation.

To install the anvil assembly 1400, the surgeon orients the first anvil segments 1430 in the down or proximal direction and the second anvil segments 1450 are oriented in the up or distal direction relative to the body portion 1412. Such first or collapsed orientation provides the anvil head 1410 with its smallest cross-sectional profile. That is, the anvil head assembly 1410 has an "overall width" that is measured along an axis that is substantially perpendicular to the shaft axis "SA-SA". When in the first or collapsed orientation, the overall width has a magnitude "D1" as shown in FIG. 71. When the anvil head assembly 1410 is in the second or expanded orientation, the magnitude of the overall width (designed as D2 in FIG. 72) is greater than magnitude of the overall width when the anvil head assembly is in the first or collapsed orientation. When in the collapsed orientation, the anvil head 1410 may pass through a particular size of opening or trocar cannula. The anvil shaft 1460 may be attached to the trocar shaft of the instrument prior to insertion into the patient or after the anvil assembly 1400 has been inserted into the patient. Thereafter, the surgeon then moves the second anvil segments 1450 downward or in the proximal direction "PD" and the first anvil segments 1430 are moved up or in the distal direction "DD". The motions may be staggered so that the second anvil segments 1450 are moved down in the proximal direction first and the first anvil segments 1430 are moved up in the distal direction and lock into the second anvil segments 1450. Such arrangement creates a single supported firing platform 1470 that the staples can react against. The instrument may then be fired. After the instrument has been fired, the second anvil segments 1450 may be moved up in the distal direction and the first anvil segments 1430 may be moved down in the proximal direction to return the anvil head 410 to the collapsed configuration. When in the collapsed configuration, the anvil assembly 1400 may be more easily removed from the target tissue.

The various embodiments of the present invention represent a vast improvement over prior circular staple arrangements and anvil assemblies therefor. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. An anvil plate for a surgical stapling instrument, said anvil plate comprising:
   a plurality of anvil plate segments movably interconnected and reconfigurable from a first orientation wherein said anvil plate segments may be inserted through a cannula opening as a unit and then reconfigured into a second orientation in the form of a substantially planar anvil plate assembly that has a diameter that is larger than a diameter of said cannula opening, wherein said plurality of anvil plate segments are coupled together by a plurality of hinges, wherein said plurality of anvil plate segments comprises four arcuate plate segments coupled by said hinges in end-to-end fashion such that when said four arcuate plate segments are in said first orientation, said four arcuate plate segments may be substantially stacked on top of each other; and
   a flexible tether threadably engaging each of said arcuate plate segments such that said arcuate plate segments may be inserted through said cannula opening in an end-to end fashion wherein said arcuate plate segments do not form an annular plate assembly and then drawn together to form said annular plate assembly by applying an actuation motion to said flexible tether to draw a free end of one of said arcuate plate segments into abutting contact with another free end of another of said arcuate plate segments to form said annular plate assembly.

2. An anvil plate for a surgical stapling instrument, said anvil plate comprising:
a plurality of anvil plate segments movably interconnected and reconfigurable from a first orientation wherein said anvil plate segments may be inserted through a cannula opening as a unit wherein at least one of said anvil plate segments is proximal to at least one other of said anvil plate segments and then reconfigured into a second orientation in the form of a substantially planar anvil plate assembly that has a diameter that is larger than a diameter of said cannula opening; and
a flexible tether threadably engaging each of said plurality of anvil plate segments such that said plurality of anvil plate segments may be inserted through said cannula opening in an end-to end fashion wherein said plurality of anvil plate segments do not form an annular plate assembly and then drawn together to form said annular plate assembly by applying an actuation motion to said flexible tether to draw a free end of one of said plurality of anvil plate segments into abutting contact with another free end of another of said plurality of anvil plate segments to form said annular plate assembly.

3. An anvil for a surgical stapling instrument, comprising:
a plurality of anvil plates movably coupled together for selective movement between non-planar orientations and a substantially planar orientation wherein said plurality of anvil plates form an annular anvil plate assembly, wherein said plurality of anvil plates are coupled together by a plurality of hinges, wherein said plurality of anvil plates comprises four arcuate plate segments coupled by said hinges in end-to-end fashion such that when said arcuate plate segments are in a first one of said non-planar orientations, said four arcuate plate segments may be substantially stacked on top of each other and when said arcuate plate segments are in another of said non-planar orientations, two of said arcuate plate segments are stacked on top of another two of said arcuate plate segments;
an anvil support member configured for attachment to said anvil plate assembly to retain said anvil plate assembly in said substantially planar orientation; and
a flexible tether threadably engaging each of said arcuate plate segments such that said arcuate plate segments may be inserted through an opening in an end-to end fashion wherein said arcuate plate segments do not form an annular plate assembly and then drawn together to form said annular plate assembly by applying an actuation motion to said flexible tether to draw a free end of one of said arcuate plate segments into abutting contact with another free end of another of said arcuate plate segments to form said annular plate assembly.

4. An anvil for a surgical stapling instrument, comprising:
a plurality of anvil plates movably coupled together for selective movement between non-planar orientations wherein at least one of said anvil plates is proximal to at least one other of said anvil plates and a substantially planar orientation wherein said plurality of anvil plates form an annular anvil plate assembly;
an anvil support member configured for attachment to said anvil plate assembly to retain said anvil plate assembly in said substantially planar orientation; and
a flexible tether threadably engaging each said anvil plate such that each said anvil plate may be inserted through an opening in an end-to end fashion wherein each said anvil plate does not form an annular plate assembly and then drawn together to form said annular plate assembly by applying an actuation motion to said flexible tether to draw a free end of one of said anvil plates into abutting contact with another free end of another of said anvil plates to form said annular plate assembly.

5. An anvil plate for a surgical stapling instrument, said anvil plate comprising a plurality of anvil plate segments movably interconnected and reconfigurable from a first, non-planar orientation wherein said anvil plate segments may be inserted through a cannula opening as a unit such that at least one of said anvil plate segments is proximal to at least one other of said anvil plate segments and then reconfigured into a second orientation in the form of a substantially planar anvil plate assembly that has a diameter that is larger than a diameter of said cannula opening.

6. The anvil plate of claim 1 wherein said plurality of anvil plate segments are coupled together by a plurality of hinges.

7. The anvil plate of claim 6 wherein said plurality of anvil plate segments comprises four arcuate plate segments coupled by said hinges in end-to-end fashion such that when said four arcuate plate segments are in said first orientation, said four arcuate plate segments may be substantially stacked on top of each other.

8. The anvil plate of claim 1 wherein said plurality of anvil plate segments comprises four arcuate plate segments wherein each said arcuate plate segment has an outer configuration of staple formation pockets and an inner configuration of staple formation pockets that are oriented to form an outer annular ring of staple formation pockets and an inner annular ring of staple formation pockets, respectively when said anvil plate is in said second orientation wherein said staple formation pockets in said inner annular ring of staple formation pockets are staggered from said staple pockets in said outer annular ring of staple formation pockets.

9. The anvil plate of claim 1 wherein said plurality of anvil plate segments are movably coupled together by a plurality of spring clips.

10. The anvil plate of claim 1 wherein each said anvil plate segment comprises an arcuate plate segment having two ends wherein each said end has an attachment joint configured to slidably mate with the attachment joint on an adjacent anvil plate segment when said plurality of anvil plate segments form said anvil plate assembly.

11. The anvil plate of claim 10 wherein each said anvil plate segment has a forming surface and wherein each said attachment joint has an attachment tab portion that is substantially parallel to said forming surface.

12. An anvil for a surgical stapling instrument, comprising:
a plurality of anvil plates movably coupled together for selective movement between non-planar orientations wherein at least one of said plurality of anvil plates is proximal to at least one other of said plurality of anvil plates and a substantially planar orientation wherein said plurality of anvil plates form an annular anvil plate assembly; and
an anvil support member configured for attachment to said anvil plate assembly to retain said anvil plate assembly in said substantially planar orientation.

13. The anvil of claim 12 wherein said plurality of anvil plates are coupled together by a plurality of hinges.

14. The anvil of claim 13 wherein said plurality of anvil plates comprises four arcuate plate segments coupled by said hinges in end-to-end fashion such that when said arcuate plate segments are in a first one of said non-planar orientations, said four arcuate plate segments may be substantially stacked on top of each other and when said arcuate plate segments are in another of said non-planar orientations, two of said arcuate plate segments are stacked on top of another two of said arcuate plate segments.

15. The anvil of claim 12 wherein said plurality of anvil plates comprises four arcuate plate segments wherein each said arcuate plate segment has an outer configuration of staple formation pockets and an inner configuration of staple formation pockets that are oriented to form an outer annular ring of staple formation pockets and an inner annular ring of staple formation pockets, respectively when said annular plate assembly is in said substantially planar orientation wherein said staple formation pockets in said inner annular ring of staple formation pockets are staggered from said staple pockets in said outer annular ring of staple formation pockets.

16. The anvil of claim 12 wherein said plurality of anvil plates are movably coupled together by a plurality of spring clips.

17. The anvil of claim 12 wherein each said anvil plate comprises an arcuate plate segment having two ends wherein each said end has an attachment joint configured to slidably mate with the attachment joint on an adjacent anvil plate when said plurality of anvil plates form said annular anvil plate assembly.

18. The anvil of claim 17 wherein each said anvil plate has a forming surface and wherein each said attachment joint has an attachment tab portion that is substantially parallel to said forming surface.

19. An anvil plate for a surgical stapling instrument, said anvil plate comprising a plurality of anvil plate segments movably interconnected and reconfigurable from a first orientation wherein said anvil plate segments may be inserted through a cannula opening as a unit such that at least one of said anvil plate segments is proximal to at least one other of said anvil plate segments and then reconfigured into a second orientation in the form of a substantially planar anvil plate assembly that has a diameter that is larger than a diameter of said cannula opening, and wherein said plurality of anvil plate segments are supported on a flexible ring member that is configurable between said first orientation and said second orientation.

20. The anvil plate of claim 19 wherein said flexible ring member is fabricated from an elastomeric material and said plurality of anvil plate segments are fabricated from metal material.

21. An anvil for a surgical stapling instrument, comprising:
 a plurality of anvil plates movably coupled together for selective movement between non-planar orientations wherein at least one of said anvil plates is proximal to at least one other of said anvil plates and a substantially planar orientation wherein said plurality of anvil plates form an annular anvil plate assembly; and
 an anvil support member configured for attachment to said anvil plate assembly to retain said anvil plate assembly in said substantially planar orientation;
 wherein said plurality of anvil plates are coupled to a flexible ring member that is configurable between said non-planar orientations and said substantially planar orientation.

22. The anvil of claim 21 wherein said flexible ring member is fabricated from an elastomeric material and said plurality of anvil plates are fabricated from metal material.

* * * * *